US011097002B2

(12) United States Patent
He et al.

(10) Patent No.: US 11,097,002 B2
(45) Date of Patent: Aug. 24, 2021

(54) NANOPARTICLE VACCINES WITH NOVEL STRUCTURAL COMPONENTS

(71) Applicant: The Scripps Research Institute, La Jolla, CA (US)

(72) Inventors: Linling He, San Diego, CA (US); Jiang Zhu, San Diego, CA (US)

(73) Assignee: The Scripps Research Institute, La Jolla, CA (US)

( * ) Notice: Subject to any disclaimer, the term of this patent is extended or adjusted under 35 U.S.C. 154(b) by 46 days.

(21) Appl. No.: 16/440,067

(22) Filed: Jun. 13, 2019

(65) Prior Publication Data

US 2020/0009244 A1 Jan. 9, 2020

Related U.S. Application Data

(60) Provisional application No. 62/684,229, filed on Jun. 13, 2018.

(51) Int. Cl.

| A61K 9/51 | (2006.01) |
| A61K 39/145 | (2006.01) |
| A61K 39/12 | (2006.01) |
| A61K 39/21 | (2006.01) |
| A61P 31/18 | (2006.01) |
| A61K 47/64 | (2017.01) |
| A61K 47/69 | (2017.01) |
| B82Y 5/00 | (2011.01) |

(52) U.S. Cl.
CPC .......... *A61K 39/21* (2013.01); *A61K 47/6425* (2017.08); *A61K 47/6929* (2017.08); *A61P 31/18* (2018.01); *B82Y 5/00* (2013.01)

(58) Field of Classification Search
CPC ...... A61K 9/51; A61K 39/71; A61K 47/6929; A61P 31/18
USPC ...... 424/9.1, 9.2, 184.1, 185.1, 204.1, 208.1
See application file for complete search history.

(56) References Cited

U.S. PATENT DOCUMENTS

| 5,736,142 A | 4/1998 | Sette et al. |
| 8,546,337 B2 | 10/2013 | Burkhard et al. |
| 9,932,370 B2 | 4/2018 | Barouch et al. |
| 2006/0228357 A1 | 10/2006 | Chang et al. |
| 2014/0212458 A1 | 7/2014 | Caulfield et al. |
| 2017/0233441 A1 | 8/2017 | Kwong et al. |

FOREIGN PATENT DOCUMENTS

| WO | 2008/063331 A2 | 5/2008 |
| WO | 2016/037154 A1 | 3/2016 |
| WO | 2016/138525 A1 | 9/2016 |
| WO | 2017/192434 A1 | 11/2017 |
| WO | 2018/050747 A1 | 3/2018 |
| WO | 2019/089817 A1 | 5/2019 |

OTHER PUBLICATIONS

Yang, X., et al., Characterization of stable, soluble timers containing complete ectodomains of human immunodeficiency virus type 1 envelope glycoproteins. J Virol. 74(12):5716-25 (2000).
Yang, X., et al., Modifications that stabilize human immunodeficiency virus envelope glycoprotein trimers in solution. J Virol. 74(10):4746-54 (2000).
Yang, X., et al., Highly stable trimers formed by human immunodeficiency virus type 1 envelope glycoproteins fused with the trimeric motif of T4 bacteriophage fibritin. J Virol. 76(9):4634-42 (2002).
Sanders, R.W., et al., Stabilization of the soluble, cleaved, trimeric form of the envelope glycoprotein complex of human immunodeficiency virus type 1. J Virol. 76(17):8875-89 (2002).
Sanders, R.W., et al., A next-generation cleaved, soluble HIV-1 Env trimer, BG505 SOSIP.664 gp140, expresses multiple epitopes for broadly neutralizing but not non-neutralizing antibodies. PLoS Pathog. 9(9):e1003618 (2013).
Sharma, S.K., et al., Cleavage-independent HIV-1 Env trimers engineered as soluble native spike mimetics for vaccine design. Cell Rep. 11(4):539-50 (2015).
Guenaga, J., et al., Structure-Guided Redesign Increases the Propensity of HIV Env to Generate Highly Stable Soluble Trimers. J Virol. 90(6):2806-17 (2015).
Georgiev, I.S., et al., Single-Chain Soluble BG505.SOSIP gp140 Trimers as Structural and Antigenic Mimics of Mature Closed HIV-1 Env. J Virol. 89(10):5318-29 (2015).
Jardine, J., et al., Rational HIV immunogen design to target specific germline B cell receptors. Science. 340 (6133):711-6 (2013).
Sliepen, K., et al., Presenting native-like HIV-1 envelope trimers on ferritin nanoparticles improves their immunogenicity. Retrovirology. 12:82 (2015).
Kong, L. et al., Uncleaved prefusion-optimized gp140 trimers derived from analysis of HIV-1 envelope metastability. Nat Commun. 7:12040 (2016).
He, L., et al., Presenting native-like trimeric HIV-1 antigens with self-assembling nanoparticles. Nat Commun. 7:12041 (2016).
White, et al., Crit Rev Biochem Mol Biol. 2008 ; 43(3): 189-219.
Krarup, et al., Nature Communications 6:8143, 2015.
Bissati, et al., Vaccines 32:3243-3248, 2014.
Broadhurst, et al., The Structure of Docking Domains Chemistry and Biology in Modular Polyketide Synthases, Chemistry & Biology, vol. 10, 723-731, 2003.
Alba Torrents De La Pena et al., Stabilizing HIV-1 Envelope Glycoprotein Trimers to Induce Neutralizing Antibodies, Retrovirology, 15:63, 2018.

(Continued)

*Primary Examiner* — Rodney P Swartz
(74) *Attorney, Agent, or Firm* — Hugh Wang; Thomas Fitting

(57) ABSTRACT

The present invention provides novel nanoparticle presented vaccine compositions that are stabilized with a locking domain. Various immunogens can be employed in the preparation of the vaccine compositions, including viral immunogens such as HIV-1 and Ebola viral immunogens, and non-viral immunogens such as immunogens derived from bacteria, parasites and mammalian species. The invention also provides methods of using such vaccine compositions in various therapeutic applications, e.g., for preventing or treating viral infections.

36 Claims, 14 Drawing Sheets

Specification includes a Sequence Listing.

(56) References Cited

OTHER PUBLICATIONS

He, et al., HIV-1 Vaccine Design Through Minimizing Envelope Metastability, Science Advances, 4:eaau6769, 2018.

Hsia, et al., Design of a Hyperstable-60 Subunit Protein Icosahedron, Nature, vol. 353 136-147, 2016.

Hu, et al., Murine Antibody Responses to Cleaved Soluble HIV-1 Envelope Trimers Are Highly Restricted in Specificity, Journal of Virology, vol. 89, No. 20, 2015.

Kesavardhana, et al., Stabilizing the Native Trimer of HIV-1 Env by Destabilizing the Heterodimeric Interface of the gp41 Postfusion Six-Helix Bundle, Journal of Virology, vol. 88, p. 9590-9604, 2014.

Liu, et al. Mutations That Destabilize the gp41 Core Are Determinants for Stabilizing the Simian Immunodeficiency Virus-CPmac Envelope Glycoprotein Complex, Journal of Biological Chemistry, vol. 277, p. 12891-12900, 2002.

Ringe, et al., Cleavage Strongly Influences Whether Soluble HIV-1 Envelope Glycoprotein Trimers Adopt a Native-like Conformation, PNAS, vol. 110, p. 18256-18261, 2013.

Sanders, et al., Variable-Loop-Deleted Variants of the Human Immunodeficiency Virus Type 1 Envelope Glycoprotein Can Be Stabilized by an Intermolecular Disulfide Bond between the gp120 and gp41 Subunits, Journal of Virology, vol. 74, p. 5091-5100, 2000.

Sen, et al., Alanine Scanning Mutagenesis of HIV-1 gp 41 Heptad Repeat 1: Insight into the gp-120-gp41 Interaction, Biochemistry, 49, 5057-5065, 2010.

Tran, et al., Structural Mechanism of Trimeric HIV-1 Envelope Glycoprotein Activation, PLOS Pathogens, vol. 8, Issue 7, 2012.

LASV GPC-FR    LASV GPC-E2p 26.3 nm    37.6 nm

B

LASV GPC-PPGG-G$_4$S-10GS-FR    LASV GPC-PPGG-G$_4$S-E2p-LD4-PADRE

NANOPARTICLE VACCINES WITH NOVEL STRUCTURAL COMPONENTS

CROSS-REFERENCE TO RELATED APPLICATIONS

The subject patent application claims the benefit of priority to U.S. Provisional Patent Application No. 62/684,229 (filed Jun. 13, 2018). The full disclosure of the priority application is incorporated herein by reference in its entirety and for all purposes.

STATEMENT OF GOVERNMENT SUPPORT

This invention was made with government support under grant numbers R01 AI129698-02 and R56 AI125078-01 awarded by The National Institutes of Health. The government has certain rights in the invention.

BACKGROUND OF THE INVENTION

Substantial progresses have been in the design of vaccines for countering infections of various pathogens such as viruses. The rational vaccine design strategy and the novel technologies recently established in the HIV-1 vaccine field provide a potential solution to vaccine development for other viral pathogens and for non-viral disease targets. The rational vaccine design strategy consists of identification of broadly neutralizing antibodies (bNAbs), structural analysis of bNAb-antigen complexes, and structure-based immunogen design and testing. In the context of immunogen design, significant breakthroughs have been seen in the stabilization and redesign of envelope (Env) proteins for several viruses and in the multivalent presentation of optimized Env proteins on virus-like particles (VLPs) or nanoparticles of similar geometry. VLPs can elicit strong, long-lasting immune responses due to its large size and dense display of surface antigens. VLPs have been developed as successful vaccines against cognate viruses (Gardasil® for Human Papillomavirus) or as carriers for foreign antigens. The optimal antigen spacing for B cell activation has been determined to be a minimum of 20-25 epitopes spaced by 5-10 nm. Therefore, self-assembling nanoparticles with the molecular traits of a VLP (ball shape, 10-100 nanometers, and etc.) may be reengineered to display diverse antigens for the development of effective VLP-type vaccines.

Significant advances have been made in the stabilization and redesign of Env proteins for several viruses. For example, HIV-1 vaccine research is now focused on antigen selection and evaluation due to a wealth of information accumulated on bNAbs and Env structures. Native-like trimers have emerged as a desirable vaccine platform due to the promising early data from the BG505 SOSIP.664 gp140 trimer. Other gp140 designs, such as sc-gp140 and NFL, also produced native-like trimers. However, all these designs would suffer significant loss in trimer yield, purity, and stability when they are applied to non-BG505 Envs, and require additional Env-stabilizing mutations and complicated purification methods to obtain native-like trimers. It was not until recently that the primary cause of Env metastability—an HR1 bend (aa 547-569) in gp41 ectodomain (gp41ECTO)—was identified and targeted directly by rational redesign. The resulting trimer construct is termed "uncleaved prefusion-optimized (UFO)" design. It was also recently demonstrated that gp41ECTO is the sole source of Env metastability, and that BG505 gp41ECTO of the UFO design can be used to stabilize diverse HIV-1 subtypes with substantial trimer yield, purity, and stability, providing a simple, general, and effective strategy for trimer-based HIV-1 vaccine design.

Significant advances have also been made in the use of self-assembling nanoparticles to display Env antigens as vaccine candidates, especially considering the poor immunogenicity observed for individual antigens. For example, HIV-1 trimer immunogenicity has been tested for SOSIP and NFL in wild-type (WT) mice, human Ig knock-in mice, rabbits, and non-human primates (NHPs), with autologous tier-2 NAb responses observed for rabbits and NHPs but not for WT mice. The induction of such tier-2 NAb responses often requires 6-12 months of immunizations, suggesting that soluble trimers may not be the optimal vaccine form. Consistently, more recent studies demonstrated that UFO trimers, with inherent stability and purity, can be displayed on three nanoparticles including 24-meric ferritin (FR), 60-meric E2p, and 60-meric I3-01 with high yield high purity. See, He et al., *Nat. Commun.* 7:12041, 2016. Such nanoparticles elicited, for the first time, notable tier-2 HIV-1 neutralizing antibody response in mice after 8 weeks, whereas all the soluble trimers failed. One of such nanoparticles elicited notable tier-2 HIV-1 neutralizing antibody responses in rabbits after 6 weeks, whereas the soluble trimer required another 8 weeks (at week 14) to develop such responses. See, He et al., *Sci. Adv.* 4(11): eaau6769, 2018.

In spite of the substantial progresses in vaccine design, there are still needs in the medical field for more effective and potent vaccine immunogens, e.g., for preventing infections of various viral or non-viral pathogens (e.g., HIV-1 infection). The present invention addresses unmet needs in the art.

SUMMARY OF THE INVENTION

In one aspect, the invention provides vaccine compositions containing (1) a polypeptide immunogen displayed on the surface of a self-assembling nanoparticle and (2) a locking domain that is embedded inside the nanoparticle and linked to subunit of the self-assembling nanoparticle. In these vaccine compositions, the locking domain is a protein subunit that can naturally form a dimer with another locking domain attached to a nearby nanoparticle subunit in solution through non-covalent interactions at the interface. In some embodiments, the employed locking domain is a protein domain or subunit that forms a homodimer with another identical protein domain or subunit. In some of these embodiments, the subunit of the employed locking domain has the amino acid sequence as shown in any one of SEQ ID NOs:1-9, a conservatively modified variant or a substantially identical sequence thereof.

In some vaccine compositions of the invention, the locking domain is covalently linked to subunit of the nanoparticle. In some of these embodiments, the N-terminus of the locking domain is fused to C-terminus of the nanoparticle subunit via a linker sequence. Some vaccine compositions of the invention can additionally contain a pan-reactive T-cell epitope. In some of these embodiments, the N-terminus of the T-cell epitope is fused to the C-terminus of the locking domain. Some vaccine compositions of the invention can additionally contain a neck region inserted between the immunogen and the nanoparticle subunit. In these embodiments, the neck region can be a 3-helix protein domain that elevates the immunogen further away from the surface of the nanoparticle. In addition to the locking domain which stabilizes the nanoparticles from the inside, some vaccine compositions of the invention can additionally contain a protein domain inserted between the immunogen and the nanoparticle subunit to further stabilize the immunogen polypeptide. In some preferred embodiments, the nanoparticle utilized for constructing the vaccine compositions of the invention is a ball-shaped nanoparticle with rotational symmetry. In some of these embodiments, the rotational symmetry has 3-fold axis and/or 5-fold axis. In some of these embodiments, the employed nanoparticle is of an icosahedral structure.

In some vaccine compositions of the invention, the polypeptide immunogen displayed on nanoparticle is a viral immunogen. In some of these embodiments, the displayed polypeptide immunogen is a viral immunogen from a virus utilizing class-I fusion mechanism. As exemplifications, the immunogen can be derived from HIV-1 virus, Ebola virus, Marburg virus, Arenaviruses, *respiratory syncytial viruses* (RSV), and coronaviruses. In some other embodiments, the displayed polypeptide immunogen is a viral immunogen from a virus utilizing class-II fusion mechanism. As exemplifications, the immunogen can be derived from is HCV or Zika virus. In still some other embodiments, the displayed polypeptide immunogen is a non-viral immunogen. As exemplifications, the displayed immunogen can be an antigen from *Plasmodium falciparum*, an antigen from *Mycobacterium tuberculosis* (TB), or human protein proprotein convertase subtilisin/kexin type 9 (PCSK9).

Some vaccine compositions of the invention are HIV-1 vaccines that display an HIV-1 Env-derived trimer protein. In some of these embodiments, the N-terminus of the locking domain is fused to C-terminus of the nanoparticle subunit via a linker sequence that contains one or more tandem copies of GGGGS (SEQ ID NO:17). In some embodiments, the vaccine composition can further contain a pan-reactive T-cell epitope. In some of these embodiments, the N-terminus of the T-cell epitope is fused to the C-terminus of the locking domain. In some of these embodiments, the T-cell epitope has the sequence AKFVAAWTLKAAA (SEQ ID NO:18). In some embodiments, the C-terminus of the subunit of the HIV-1 trimer protein is covalently linked to N-terminus of the subunit of the nanoparticle. In some embodiments, the HIV-1 trimer protein subunit is fused to the nanoparticle subunit via a linker sequence. In various embodiments, the employed linker sequence can have a sequence (GaSb)n, wherein a is an integer of 1 to 5, b is an integer of 1 to 2, and n is an integer of 1 to 5.

In some vaccine compositions of the invention, the self-assembling nanoparticle has a trimeric sequence that forms a trimer. In some of these embodiments, the subunit of the self-assembling nanoparticle is a polypeptide having a sequence as shown in SEQ ID NO:26 (ferritin), SEQ ID NO:21 (E2p), SEQ ID NO:22 (I3-01) or SEQ ID NO:25 (I3-01 variant), a conservatively modified variant or a substantially identical sequence thereof. In some HIV-1 vaccine compositions, the displayed HIV-1 Env-derived trimer protein is derived from gp140. In some embodiments, the HIV-1 Env-derived trimer protein is an uncleaved prefusion-optimized (UFO) gp140 trimer. In some of these embodiments, the UFO gp140 trimer is a chimeric trimer containing a modified gp41$_{ECTO}$ domain from HIV-1 strain BG505. In some embodiments, the subunit of the UFO gp140 trimer has the amino acid sequence shown in SEQ ID NO:23, a conservatively modified variant or a substantially identical sequence thereof.

Some specific HIV-1 vaccine compositions are comprised from a subunit sequence containing from the N-terminus to the C-terminus: HIV-1 Env-derived UFO gp140 trimer subunit as shown in SEQ ID NO:23, self-assembling nanoparticle subunit as shown in SEQ ID NO:21 (E2p), the locking domain as shown in SEQ ID NO:1 (LD4), and T-cell epitope AKFVAAWTLKAAA (SEQ ID NO:18). In some of these embodiments, the subunit sequence can further contain a first linker sequence (GGGGS)$_2$ (SEQ ID NO:24) between the gp140 trimer subunit and the nanoparticle subunit, and/or a second linker sequence GGGGS (SEQ ID NO:17) between the nanoparticle subunit and the locking domain. Some other specific HIV-1 vaccine compositions are comprised from a subunit sequence containing from the N-terminus to the C-terminus: HIV-1 Env-derived UFO gp140 trimer as shown in SEQ ID NO:23, self-assembling nanoparticle subunit as shown in SEQ ID NO:22 or 25 (I3-01), the locking domain as shown in SEQ ID NO:2 (LD7), and T-cell epitope AKFVAAWTLKAAA (SEQ ID NO:18). In some of these embodiments, the subunit sequence can further contain a first linker sequence (GGGGS)$_2$ (SEQ ID NO:24) between the gp140 trimer subunit and the nanoparticle subunit, and/or a second linker sequence GGGGS (SEQ ID NO:17) between the nanoparticle subunit and the locking domain.

In a related aspect, the invention provides pharmaceutical compositions that contain the vaccine compositions described herein. The pharmaceutical compositions typically also contain a pharmaceutically acceptable carrier. In some embodiments, the pharmaceutical compositions can also contain an adjuvant.

In another aspect, the invention provides polynucleotides encoding a fusion protein that contains an immunogen polypeptide at the N-terminus, a self-assembling nanoparticle subunit, and subunit of a locking domain. The locking domain in the fusion protein is a protein subunit that can naturally form a dimer with another locking domain attached to a nearby nanoparticle subunit in solution through non-covalent interactions at the interface. In some polynucleotides of the invention, the locking domain in the encoded fusion protein is a protein subunit that forms a homodimer with another identical protein subunit. In some embodiments, the immunogen polypeptide in the encoded fusion protein is fused to the N-terminus of the nanoparticle subunit. In some embodiments, the immunogen polypeptide in the encoded fusion protein is the subunit of a multimeric protein. In some embodiments, the locking domain in the encoded fusion protein is located at the C-terminus of the nanoparticle subunit. In some embodiments, the encoded fusion protein further contains a T-cell epitope at the C-terminus. In some embodiments, the immunogen polypeptide in the encoded fusion protein is subunit of an HIV-1 Env-derived trimer protein. In some of these embodiments, the encoded fusion protein can additionally contain one or more linker sequences between the different components of the protein. In some of these embodiments, the encoded fusion protein can contain a first linker sequence between the immunogen polypeptide and the nanoparticle subunit, and/or a second linker sequence between the nanoparticle subunit and the locking domain. In various embodiments, the employed linker sequences can each independently have the sequence of (GaSb)n, wherein a is an integer of 1-4, b is an integer of 1-2, and n is an integer of 1-6.

Some specific polynucleotides of the invention encode HIV-1 polypeptide vaccine compositions described herein. In some of these embodiments, the encoded fusion protein contains from the N-terminus to the C-terminus: UFO gp140 trimer subunit shown in SEQ ID NO:23, self-assembling nanoparticle subunit as shown in SEQ ID NO:21 (E2p), the locking domain as shown in SEQ ID NO:1 (LD4), and T-cell epitope AKFVAAWTLKAAA (SEQ ID NO:18). In some embodiments, the encoded fusion polypeptide can additional contain a first linker sequence (GGGGS)$_2$ (SEQ ID NO:24) between the gp140 trimer subunit and the nanoparticle subunit, and/or a second linker sequence GGGGS (SEQ ID NO:17) between the nanoparticle subunit and the locking domain. In some other embodiments, the encoded fusion protein contains from the N-terminus to the C-terminus: UFO gp140 trimer subunit shown in SEQ ID NO:23, self-assembling nanoparticle subunit as shown in SEQ ID NO:22 or 25 (I3-01), the locking domain as shown in SEQ ID NO:2 (LD7), and T-cell epitope AKFVAAWTLKAAA (SEQ ID NO:18). In some embodiments, the encoded fusion polypeptide can additional contain a first linker sequence (GGGGS)$_2$ (SEQ ID NO:24) between the gp140 trimer subunit and the nanoparticle subunit, and/or a second linker sequence GGGGS (SEQ ID NO:17) between the nanoparticle subunit and the locking domain.

In some related embodiments, the invention provides polypeptides encoded by the polynucleotides described herein. In some related embodiments, the invention provides vectors that harbor one or more of the polynucleotides described herein. In some other related embodiments, the invention provides pharmaceutical compositions that contain one or more of the polynucleotides or vectors described herein.

In another aspect, the invention provides methods for treating or preventing HIV-1 infections in a subject. These methods involve administering to the subject a pharmaceutical composition that contains a therapeutically effective amount of the HIV-1 polypeptide vaccine composition described herein. In some of these embodiments, the administered HIV-1 vaccine composition contains from the N-terminus to the C-terminus: UFO gp140 trimer subunit shown in SEQ ID NO:23, self-assembling nanoparticle subunit as shown in SEQ ID NO:21 (E2p), the locking domain as shown in SEQ ID NO:1 (LD4), and T-cell epitope AKFVAAWTLKAAA (SEQ ID NO:18). In some other embodiments, the administered HIV-1 vaccine composition contains from the N-terminus to the C-terminus: UFO gp140 trimer subunit shown in SEQ ID NO:23, self-assembling nanoparticle subunit as shown in SEQ ID NO:22 or 25 (I3-01), the locking domain as shown in SEQ ID NO:2 (LD7), #↝#]] and T-cell epitope AKFVAAWTLKAAA (SEQ ID NO:18). In some related embodiments, the invention provides methods for treating or preventing HIV-1 infection in a subject by administering to the subject a pharmaceutical composition containing a therapeutically effective amount of the polynucleotide or expression vector described herein. In some of these embodiments, the administered polynucleotide or vector encodes a fusion protein that contains from the N-terminus to the C-terminus: UFO gp140 trimer subunit shown in SEQ ID NO:23, self-assembling nanoparticle subunit as shown in SEQ ID NO:21 (E2p), the locking domain as shown in SEQ ID NO:1 (LD4), and T-cell epitope AKFVAAWTLKAAA (SEQ ID NO:18). In some other embodiments, the administered polynucleotide or vector encodes a fusion protein that contains from the N-terminus to the C-terminus: UFO gp140 trimer subunit shown in SEQ ID NO:23, self-assembling nanoparticle subunit as shown in SEQ ID NO:22 or 25 (I3-01), the locking domain as shown in SEQ ID NO:2 (LD7), and T-cell epitope AKFVAAWTLKAAA (SEQ ID NO:18).

A further understanding of the nature and advantages of the present invention may be realized by reference to the remaining portions of the specification and claims.

DESCRIPTION OF THE DRAWINGS

FIG. 9 shows molecular models of Lassa virus (LASV) GPC trimer-presenting nanoparticles as well as negative-stain EM images of GPC trimers on 24-meric ferritin nanoparticle and on 60-meric E2p nanoparticle with locking domain LD4 and T-cell epitope PADRE. (A): Two fusion constructs (GPC-10GS-FR and GPC-5GS-E2p-LD4-PADRE) leading to nanoparticles with diameters of 26.3 nm and 37.6 nm, respectively. (B): Negative-stain EM analysis of 37.7H antibody column purified proteins.

DETAILED DESCRIPTION

I Overview

Figure 1:
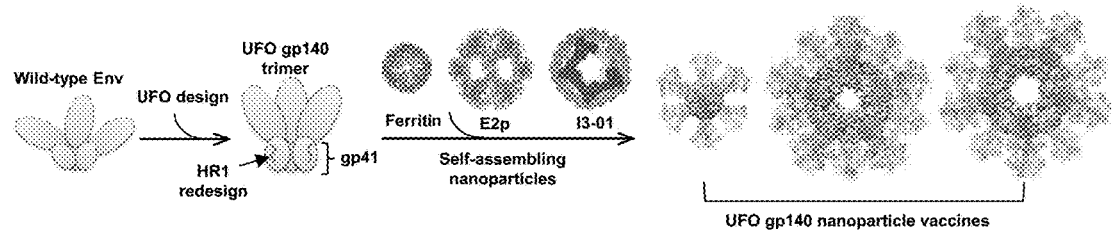
FIG. 1 shows the structure of HIV-1 UFO gp140 nanoparticle vaccine.

The present invention is predicated in part on the present inventors' development of novel vaccine immunogens against various viral or non-viral targets (e.g., HIV-1 Env, Ebola GP, HCV E2 protein or *M tuberculosis* antigens) and nanoparticle-presented immunogens (i.e., vaccine compositions) that demonstrate improved stability and activities. Typically, the vaccines or vaccine compositions of the invention contain an immunogen polypeptide or protein (e.g., an HIV-1 Env-derived trimer protein) that is presented on a self-assembling nanoparticle or a virus-like particle (VLP). The nanoparticle vaccines also contain one or more novel structural components described herein. These additional structural components function to facilitate the immunogen display on the surface of the nanoparticles, to enhance the stability of the displayed immunogens, and/or to improve yield and purity of the self-assembled protein vaccines. In some embodiments, the nanoparticle vaccines of the invention contain a locking domain that stabilizes the nanoparticle. As detailed in the Examples herein, the locking domain stabilizes the nanoparticles from the inside so that the nanoparticles presenting the immunogen polypeptide (e.g., an HIV-1 Env derived trimer protein) can remain intact during manufacture, vaccine formulation, and immunization. The novel vaccine immunogens thus constructed have significantly enhanced stability. In addition, the locking mechanism is independent of nanoparticle platforms. As exemplified herein (e.g., HIV-1 vaccine), it can be applied to different nanoparticles, e.g., 60-meric I3-01 and E2p nanoparticles, with nearly identical outcomes as indicated by SEC, BN-PAGE, DSC, negative-stain EM, and antigenic profiling.

Other than the locking domain, the constructs encoding the vaccines can additionally or alternatively contain various other structural components. For example, the coding sequence of a protein domain that serves to stabilize the immunogen polypeptide, such as the trimerization motif of T4 fibritin ("foldon"), or to elevate the immunogen polypeptide from the nanoparticle surface, such as a three-helix bundle ("neck domain"), or to facilitate immunoaffinity purification, such as a protein domain with known binding antibodies, can be added between the immunogen polypeptide sequence and the nanoparticle subunit sequence. The coding sequence of a polypeptide fragment or motif that serves as an active site for chemical conjugation can be inserted into the construct at an appropriate position. Additional structural components such as a CD4+ T-helper epitope or a CD8+ T-cell epitope can also be inserted into the construct at an appropriate position as described herein. As exemplified herein, one or more linkers (linker sequences, motifs or moieties) can be used to connect the various structural components in the constructs.

As detailed herein, the vaccine compositions of the invention are expressed and self-assembled from constructs that contain operably linked coding sequences of the structural components described herein. In the constructs, the immunogen polypeptide coding sequence is fused directly or indirectly at its C-terminus to the N-terminus of the nanoparticle subunit coding sequence. Sequences encoding the other structural components are inserted into the constructs at appropriate positions as described herein. For example, when a locking domain is used, the locking domain coding sequence can be fused directly or indirectly to the C-terminus of the nanoparticle subunit coding sequence.

The nanoparticle vaccine constructs exemplified herein demonstrated high yield, high purity, and high stability, with native-like antigen structures presented on the surface, enhanced native-like antigenic profiles, and enhanced immunogenicity in animals. For example, the HIV-1 nanoparticle vaccines elicited tier-2 autologous neutralizing antibody responses in wild-type mice and rabbits within 6-8 weeks, whereas soluble trimers along could not induce any tier-2 neutralizing antibodies in mice and need 2-3 months of minimal time for antibody elicitation. Thus, the improved HIV-1 vaccine immunogens of the invention are more suitable for vaccine production and enable better immune responses in vaccination.

Unless otherwise specified herein, the vaccine immunogens of the invention, the encoding polynucleotides, expression vectors and host cells, as well as the related therapeutic applications, can all be generated or performed in accordance with the procedures exemplified herein or routinely practiced methods well known in the art. See, e.g., Methods in Enzymology, Volume 289: Solid-Phase Peptide Synthesis, J. N. Abelson, M. I. Simon, G. B. Fields (Editors), Academic Press; 1st edition (1997) (ISBN-13: 978-0121821906); U.S. Pat. Nos. 4,965,343, and 5,849,954; Sambrook et al., Molecular Cloning: A Laboratory Manual, Cold Spring Harbor Press, N.Y., ($3^{rd}$ ed., 2000); Brent et al., Current Protocols in Molecular Biology, John Wiley & Sons, Inc. (ringbou ed., 2003); Davis et al., Basic Methods in Molecular Biology, Elsevier Science Publishing, Inc., New York, USA (1986); or Methods in Enzymology: Guide to Molecular Cloning Techniques Vol. 152, S. L. Berger and A. R. Kimmerl Eds., Academic Press Inc., San Diego, USA (1987); Current Protocols in Protein Science (CPPS) (John E. Coligan, et. al., ed., John Wiley and Sons, Inc.), Current Protocols in Cell Biology (CPCB) (Juan S. Bonifacino et. al. ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998). The following sections provide additional guidance for practicing the compositions and methods of the present invention.

II. Definitions

Unless defined otherwise, all technical and scientific terms used herein have the same meaning as commonly understood by those of ordinary skill in the art to which this invention pertains. The following references provide one of skill with a general definition of many of the terms used in this invention: *Academic Press Dictionary of Science and Technology*, Morris (Ed.), Academic Press ($1^{st}$ ed., 1992); *Oxford Dictionary of Biochemistry and Molecular Biology*, Smith et al. (Eds.), Oxford University Press (revised ed., 2000); *Encyclopaedic Dictionary of Chemistry*, Kumar (Ed.), Anmol Publications Pvt. Ltd. (2002); *Dictionary of Microbiology and Molecular Biology*, Singleton et al. (Eds.), John Wiley & Sons ($3^{rd}$ ed., 2002); *Dictionary of Chemistry*, Hunt (Ed.), Routledge ($1^{st}$ ed., 1999); *Dictionary of Pharmaceutical Medicine*, Nahler (Ed.), Springer-Verlag Telos (1994); *Dictionary of Organic Chemistry*, Kumar and Anandand (Eds.), Anmol Publications Pvt. Ltd. (2002); and *A Dictionary of Biology* (*Oxford Paperback Reference*), Martin and Hine (Eds.), Oxford University Press ($4^{th}$ ed., 2000). Further clarifications of some of these terms as they apply specifically to this invention are provided herein.

As used herein, the singular forms "a," "an," and "the," refer to both the singular as well as plural, unless the context clearly indicates otherwise. For example, "an Env-derived trimer" can refer to both single or plural Env-derived trimer molecules, and can be considered equivalent to the phrase "at least one Env-derived trimer."

As used herein, the terms "antigen" or "immunogen" are used interchangeably to refer to a substance, typically a protein, which is capable of inducing an immune response in a subject. The term also refers to proteins that are immunologically active in the sense that once administered to a subject (either directly or by administering to the subject a nucleotide sequence or vector that encodes the protein) is able to evoke an immune response of the humoral and/or cellular type directed against that protein. Unless otherwise noted, the term "vaccine immunogen" is used interchangeably with "protein antigen" or "immunogen polypeptide".

The term "conservatively modified variant" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For polypeptide sequences, "conservatively modified variants" refer to a variant which has conservative amino acid substitutions, amino acid residues replaced with other amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Epitope refers to an antigenic determinant. These are particular chemical groups or peptide sequences on a molecule that are antigenic, such that they elicit a specific immune response, for example, an epitope is the region of an antigen to which B and/or T cells respond. Epitopes can be formed both from contiguous amino acids or noncontiguous amino acids juxtaposed by tertiary folding of a protein.

Effective amount of a vaccine or other agent that is sufficient to generate a desired response, such as reduce or eliminate a sign or symptom of a condition or disease, such as AIDS. For instance, this can be the amount necessary to inhibit viral replication or to measurably alter outward symptoms of the viral infection, such as increase of T cell counts in the case of an HIV-1 infection. In general, this amount will be sufficient to measurably inhibit virus (for example, HIV) replication or infectivity. When administered to a subject, a dosage will generally be used that will achieve target tissue concentrations (for example, in lymphocytes) that has been shown to achieve in vitro inhibition of viral replication. In some embodiments, an "effective amount" is one that treats (including prophylaxis) one or more symptoms and/or underlying causes of any of a disorder or disease, for example to treat HIV-1 infection. In some embodiments, an effective amount is a therapeutically effective amount. In some embodiments, an effective amount is an amount that prevents one or more signs or symptoms of a particular disease or condition from developing, such as one or more signs or symptoms associated with AIDS.

As used herein, a fusion protein is a recombinant protein containing amino acid sequence from at least two unrelated proteins that have been joined together, via a peptide bond, to make a single protein. The unrelated amino acid sequences can be joined directly to each other or they can be joined using a linker sequence. As used herein, proteins are unrelated, if their amino acid sequences are not normally found joined together via a peptide bond in their natural environment(s) (e.g., inside a cell). For example, the amino acid sequences of bacterial enzymes such as *B. stearothermophilus* dihydrolipoyl acyltransferase (E2p) and the amino acid sequences of HIV-1 gp120 or gp41 glycoproteins are not normally found joined together via a peptide bond.

A heptad repeat (HR) refers to a structural motif that consists of a repeating pattern of seven amino acids: a b c d e f g H P H C P C. where H represents hydrophobic residues, C represents, typically, charged residues, and P represents polar (and, therefore, hydrophilic) residues.

HIV-1 envelope protein (Env) is initially synthesized as a longer precursor protein of 845-870 amino acids in size, designated gp160. gp160 forms a homotrimer and undergoes glycosylation within the Golgi apparatus. In vivo, gp160 glycoprotein is endo-proteolytically processed to the mature envelope glycoproteins gp120 and gp41, which are noncovalently associated with each other in a complex on the surface of the virus. The gp120 surface protein contains the high affinity binding site for human CD4, the primary receptor for HIV, as well as domains that interact with fusion coreceptors, such as the chemokine receptors CCR5 and CXCR4. The gp41 protein spans the viral membrane and contains at its amino-terminus a sequence of amino acids important for the fusion of viral and cellular membranes. The native, fusion-competent form of the HIV-1 envelope glycoprotein complex is a trimeric structure composed of three gp120 and three gp41 subunits. The receptor-binding (CD4 and co-receptor) sites are located in the gp120 moieties, whereas the fusion peptides are located in the gp41 components. Exemplary sequence of wildtype gp160 polypeptides are shown in GenBank, e.g., under accession numbers AAB05604 and AAD12142.

gp140 refers to an oligomeric form of HIV envelope protein, which contains all of gp120 and the entire gp41 ectodomain. As used herein, a HIV-1 gp140 trimer immunogen typically contains a gp140 domain and a modified or redesigned ectodomain of gp140 ($gp41_{ECTO}$).

gp120 is an envelope protein of the Human Immunodeficiency Virus (HIV). gp120 contains most of the external, surface-exposed, domains of the HIV envelope glycoprotein complex, and it is gp120 which binds both to cellular CD4 receptors and to cellular chemokine receptors (such as CCR5). The mature gp120 wildtype polypeptides have about 500 amino acids in the primary sequence. Gp120 is heavily N-glycosylated giving rise to an apparent molecular weight of 120 kD. The polypeptide is comprised of five conserved regions (C1-O5) and five regions of high variability (V1-V5). In its tertiary structure, the gp120 glycoprotein is comprised of three major structural domains (the outer domain, the inner domain, and the bridging sheet) plus the variable loops. See, e.g., Wyatt et al., Nature 393, 705-711, 1998; and Kwong et al., Nature 393, 649-59, 1998. The inner domain is believed to interact with the gp41 envelope glycoprotein, while the outer domain is exposed on the assembled envelope glycoprotein trimer.

Variable region 1 and Variable Region 2 (V1/V2 domain) of gp120 are comprised of about 50-90 residues which contain two of the most variable portions of HIV-1 (the V1 loop and the V2 loop), and one in ten residues of the V1N2 domain are N-glycosylated.

gp41 is a proteolytic product of the precursor HIV envelope protein. It contains an N-terminal fusion peptide (FP), a transmembrane domain, as well as an ectodomain that links the fusion peptide and a transmembrane domain. gp41 remains in a trimeric configuration and interacts with gp120 in a non-covalent manner. The amino acid sequence of an exemplary gp41 is set forth in GenBank, under Accession No. CAD20975.

BG505 SOSIP.664 gp140 is a HIV-1 Env immunogen developed with the gp140 trimer from Glade-A strain BG505. It contains a covalent linkage between the cleaved gp120 and $gp41_{ECTO}$ with an engineered disulfide bond (termed SOS). In addition, it has an I559P mutation (termed IP) to destabilize the gp41 post-fusion conformation and also a truncation of the membrane-proximal external region (MPER) at residue 664 to improve solubility. This HIV-1 immunogen has an outstanding antigenic profile and excellent structural mimicry of the native spike. Using the SOSIP trimer as a sorting probe, new bNAbs have been identified and characterized. The SOSIP design has also been extended to other HIV-1 strains and permitted the incorporation of additional stabilizing mutations. Recently, immunogenicity of SOSIP trimers in rabbits and nonhuman primates was reported, paving the way for human vaccine trials.

Immunogen is a protein or a portion thereof that is capable of inducing an immune response in a mammal, such as a mammal infected or at risk of infection with a pathogen. Administration of an immunogen can lead to protective immunity and/or proactive immunity against a pathogen of interest.

Immune response refers to a response of a cell of the immune system, such as a B cell, T cell, or monocyte, to a stimulus. In some embodiment, the response is specific for a particular antigen (an "antigen-specific response"). In some embodiments, an immune response is a T cell response, such as a CD4+ response or a CD8+ response. In some other embodiments, the response is a B cell response, and results in the production of specific antibodies.

Immunogenic composition refers to a composition comprising an immunogenic polypeptide that induces a measurable CTL response against virus expressing the immunogenic polypeptide, or induces a measurable B cell response (such as production of antibodies) against the immunogenic polypeptide.

Sequence identity or similarity between two or more nucleic acid sequences, or two or more amino acid sequences, is expressed in terms of the identity or similarity between the sequences. Sequence identity can be measured in terms of percentage identity; the higher the percentage, the more identical the sequences are. Two sequences are "substantially identical" if two sequences have a specified percentage of amino acid residues or nucleotides that are the same (i.e., 60% identity, optionally 65%, 70%, 75%, 80%, 85%, 90%, 95%, or 99% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 50 nucleotides (or 10 amino acids) in length, or more preferably over a region that is 100 to 500 or 1000 or more nucleotides (or 20, 50, 200 or more amino acids) in length.

Homologs or orthologs of nucleic acid or amino acid sequences possess a relatively high degree of sequence identity/similarity when aligned using standard methods. Methods of alignment of sequences for comparison are well known in the art. Various programs and alignment algorithms are described in: Smith & Waterman, Adv. Appl. Math. 2:482, 1981; Needleman & Wunsch, J. Mol. Biol. 48:443, 1970; Pearson & Lipman, Proc. Natl. Acad. Sci. USA 85:2444, 1988; Higgins & Sharp, Gene, 73:237-44, 1988; Higgins & Sharp, CABIOS 5:151-3, 1989; Corpet et al., Nuc. Acids Res. 16:10881-90, 1988; Huang et al. Computer Appls. in the Biosciences 8, 155-65, 1992; and Pearson et al., Meth. Mol. Bio. 24:307-31, 1994. Altschul et al., J. Mol. Biol. 215:403-10, 1990, presents a detailed consideration of sequence alignment methods and homology calculations.

The term "subject" refers to any animal classified as a mammal, e.g., human and non-human mammals. Examples of non-human animals include dogs, cats, cattle, horses, sheep, pigs, goats, rabbits, and etc. Unless otherwise noted, the terms "patient" or "subject" are used herein interchangeably. Preferably, the subject is human.

The term "treating" or "alleviating" includes the administration of compounds or agents to a subject to prevent or delay the onset of the symptoms, complications, or biochemical indicia of a disease (e.g., an HIV infection), alleviating the symptoms or arresting or inhibiting further development of the disease, condition, or disorder. Subjects in need of treatment include those already suffering from the disease or disorder as well as those being at risk of developing the disorder. Treatment may be prophylactic (to prevent or delay the onset of the disease, or to prevent the manifestation of clinical or subclinical symptoms thereof) or therapeutic suppression or alleviation of symptoms after the manifestation of the disease.

Uncleaved pre-fusion-optimized (UFO) trimers refer to HIV-1 gp140 trimeric proteins that are formed with gp120 protein and a redesigned $gp41_{ECTO}$ domain, which results in more stabilized HIV-1 gp140 trimers (FIG. 1). The redesigned $gp41_{ECTO}$ domain is based on the prototype HIV-1 strain BG505 (and the prototype gp140 trimer BG505 SOSIP.664 gp140) and contains one or more modifications relative to the wildtype BG505 $gp41_{ECTO}$ sequence. These modifications include (1) replacement of the 21 residue N-terminus of HR1 (residues 548-568) with a shorter loop sequence to stabilize the pre-fusion gp140 structure and (2) replacement of the furin cleavage site between gp120 and gp41 (residues 508-511) with a flexible linker sequence such a tandem repeat of a GGGGS (SEQ ID NO:17) motif. In some embodiments, the UFO trimer can additionally contain an engineered disulfide bond between gp120 and gp41 and/or a stabilizing mutation in gp41. For example, UFO trimers based on HIV-1 strain BG505 can contain an engineered disulfide bond between residues A501C and T605C. Detailed description of UFO trimers is provided in, e.g., Kong et al., Nat. Comm. 7:12040, 2016. In addition to UFO trimers based on the BG505 strain sequence, the engineered $gp41_{ECTO}$ domain can be used to pair with a gp120 polypeptide from many different HIV-1 strains or subtypes to form "chimeric" gp140 trimers. Such chimeric trimers are termed "UFO-BG" or "$UFO^2$-BG" as exemplified herein. Detailed description of UFO-BG and $UFO^2$-BG trimers is provided in, e.g., He et al., Sci Adv. 4(11):eaau6769, 2018.

Vaccine refers to a pharmaceutical composition that elicits a prophylactic or therapeutic immune response in a subject. In some cases, the immune response is a protective immune response. Typically, a vaccine elicits an antigen-specific immune response to an antigen of a pathogen, for example a viral pathogen, or to a cellular constituent correlated with a pathological condition. A vaccine may include a polynucleotide (such as a nucleic acid encoding a disclosed antigen), a peptide or polypeptide (such as a disclosed antigen), a virus, a cell or one or more cellular constituents. In some embodiments of the invention, vaccines or vaccine immunogens or vaccine compositions are expressed from fusion constructs and self-assemble into nanoparticles displaying an immunogen polypeptide or protein on the surface.

Virus-like particle (VLP) refers to a non-replicating, viral shell, derived from any of several viruses. VLPs are generally composed of one or more viral proteins, such as, but not limited to, those proteins referred to as capsid, coat, shell, surface and/or envelope proteins, or particle-forming polypeptides derived from these proteins. VLPs can form spontaneously upon recombinant expression of the protein in an appropriate expression system. Methods for producing particular VLPs are known in the art. The presence of VLPs following recombinant expression of viral proteins can be detected using conventional techniques known in the art, such as by electron microscopy, biophysical characterization, and the like. See, for example, Baker et al. (1991) Biophys. J. 60:1445-1456; and Hagensee et al. (1994) J. Virol. 68:4503-4505. For example, VLPs can be isolated by density gradient centrifugation and/or identified by characteristic density banding. Alternatively, cryoelectron microscopy can be performed on vitrified aqueous samples of the VLP preparation in question, and images recorded under appropriate exposure conditions.

A self-assembling nanoparticle refers to a ball-shape protein shell with a diameter of tens of nanometers and well-defined surface gemoetry that is formed by identical copies of a non-viral protein capable of automatically assembling into a nanoparticle with a similar appearance to VLPs. Known examples include ferritin (FR), which is conserved across species and forms a 24-mer, as well as *B. stearothermophilus* dihydrolipoyl acyltransferase (E2p), *Aquifex aeolicus* lumazine synthase (LS), and *Thermotoga maritima* encapsulin, which all form 60-mers. Self-assembling nanoparticles can form spontaneously upon recombinant expression of the protein in an appropriate expression system. Methods for nanoparticle production, detection, and characterization can be conducted using the same techniques developed for VLPs.

III. Immunogen Polypeptides or Proteins for Generating Vaccine Compositions

Any polypeptide immunogens or multimeric proteins can be used in the vaccine design of the invention. These include any proteins or polypeptides from pathogens against which an elicited immune response may be desired. Thus, the vaccine compositions of the invention can utilize immunogen polypeptides that are derived from any viruses, bacteria or other pathogenic organisms. Suitable immunogen polypeptides for the invention can also be derived from non-pathogenic species, including human proteins, against which an elicited immune response may have a therapeutic effect, alleviate disease symptoms, or improve general health. In general, the immunogen polypeptide can be any structural or functional polypeptide or peptide that contains at least about 10 amino acid residues. In some embodiments, the immunogen polypeptides contains between about 10 to about 10,000 amino acid residues in length. In some embodiments, the immunogen polypeptides contains between about 25 to about 2,000 amino acid residues in length. In some embodiments, the immunogen polypeptides contains about 50 to about 500 amino acid residues in length. Thus, the immunogen polypeptides or proteins suitable for the invention can have a molecular weight of from about 1 kDa to about 1,000 kDa, and preferably from about 2.5 kDa to about 250 kDa. In some more preferred embodiments, the employed immunogen polypeptide has a molecular weight of about 5 kDa to about 25 kDa or 50 kDa.

In some embodiments, the immunogen polypeptide or protein used in the vaccine compositions of the invention can be derived from a viral surface or core protein (target polypeptide). There are many known viral proteins that are important for viral infection of host cells. Examples include, but are not limited to, glycoproteins (or surface antigens, e.g., GP120 and GP41) and capsid proteins (or structural proteins, e.g., P24 protein) of HIV; surface antigens or core proteins of hepatitis A, B, C, D or E virus (e.g., small hepatitis B virus surface antigen (S-HBsAg) and the core proteins of hepatitis C virus, NS3, NS4 and NS5 antigens); glycoproteins gp350/220 of Epstein-Barr virus (EBV), glycoprotein (G-protein) or the fusion protein (F-protein) of respiratory syncytial virus (RSV); surface and core proteins of herpes simplex virus HSV-1 and HSV-2 (e.g., glycoprotein D from HSV-2), surface proteins (e.g., gB, gC, gD, gH and gL) of poliovirus, envelope glycoproteins hemagglutinin (H) and fusion protein (F) of measles virus (MV), glycoprotein G of lymphocytic choriomeningitis virus (LCMV), fiber and penton base proteins of adenoviruses, S spikes of coronaviruses, envelope (E) proteins of flaviviruses such as Dengue virus, yellow fever virus, and Zika virus, and non-enveloped capsid proteins of picornaviruses.

In some embodiments, viral immunogens suitable for the invention can be derived from viruses utilizing the class-I fusion mechanism for infection. Class-I viral fusion proteins are trimers that will undergo dramatic conformational changes during cell entry. Specific regions in the viral protein can completely refold to facilitate membrane fusion. As exemplified herein, examples of immunogens of viruses utilizing class-I fusion mechanism include structural proteins or polypeptides obtained from HIV-1, from viruses that cause hemorrhagic fevers such as Filoviruses (e.g., Ebola virus and Marburg viruses) and Arenaviruses (e.g., Lassa virus), from respiratory syncytial virus (RSV), and from coronaviruses such as MERS-CoV and SARS-CoV. As exemplified herein, suitable immunogens can be any proteins and polypeptides that are derived from HIV-1 UFO trimmer, Ebola GP ectodomain, LASV glycoprotein complex (GPC), RSV glycoprotein F, and MERS-CoV spike protein S. Any of these immunogens, or immunogens derived from structural proteins of other viruses utilizing the class-I fusion mechanism, can all be employed in the vaccine design of the invention.

In some embodiments, viral immunogens suitable for the invention can be derived from viruses utilizing the class-II fusion mechanism for infection. Class-II viral fusion proteins exist in the form of heterodimer (e.g., hepatitis C virus) or homodimer (e.g., Dengue and Zika viruses), which will refold to form a trimeric spike prior to membrane fusion. As exemplified herein, suitable immunogens can be any proteins and polypeptides that are derived from HCV envelope glycoproteins (e.g., E2), Zika virus E protein (e.g., the DIII domain) or any structural proteins of other viruses utilizing the class-II fusion mechanism. Any of these immunogens can all be readily employed in the vaccine design of the invention.

In some embodiments, the immunogen polypeptide or protein used in the vaccine compositions of the invention can be derived from a non-viral target. These include immunogens that can be obtained from any non-viral pathogens (e.g., bacterial pathogens) as well as parasitic organisms inside mammalian hosts such as human. In some embodiments, bacterial proteins that are important for bacterial infections are suitable for obtaining immunogen polypeptides in the vaccine design of the invention. Suitable immunogens can be any proteins and polypeptides that are derived from structural proteins of the bacteria, e.g., Ag85 complex and Mtb72 as exemplified herein with *Mycobacterium tuberculosis* (TB). In some embodiments, parasitic proteins that are important for parasite transmission, reproduction in the hosts, and life cycle are suitable for obtaining immunogen polypeptides in the vaccine design of the invention. Suitable immunogens can be any proteins and polypeptides that are derived from structural proteins of the parasites, e.g., Pfs25, circumsporozoite protein (CSP), and reticulocyte binding protein homolog 5 (PfRH5) of *Plasmodium Falciparum* (Malaria) as exemplified herein.

In some embodiments, the employed immunogen polypeptide can be an endogenous protein from a mammalian host (e.g., human), against which an elicited immune response is desired. These include, e.g., PCSK9 for regulating cholesterol level as exemplified herein, and ghrelin for controlling appetite. Various other mammalian proteins can also be used to obtain suitable immunogen polypeptides for constructing vaccines in accordance with the design of the invention. In some embodiments, the non-viral target for vaccine design can be other proteins implicated in human diseases. These include proteins that are involved in the development of cancers. Examples of cancer related immunogens also include non-mutated self-antigens, e.g., MAGE-A3, Melan-A/Mart1, gp100, Her2/Neu, and NY-ESO-1. In some additional embodiments, the immunogen polypeptides or proteins for use in vaccine compositions of the invention include proteins implicated in other chronic human diseases or disorders. Examples of such human target include, e.g., Ang-II for hypertension, TNF-α for inflammations, IL-9 for pathogen-induced eosinophilia, IL-5 for asthma, N-methyl-D-aspartate receptor-1 for stroke and human chorionic gonadotropin (hCG) for decreasing hormone levels.

IV. Locking Domains

As noted above, some nanoparticle vaccines or immunogens of the invention utilize a locking mechanism developed by the inventors. The locking mechanism refers to a protein domain ("locking domain") that functions to stabilize the nanoparticles from the inside in displaying the immunogen protein or polypeptide (e.g., Env-derived HIV-1 trimer protein). In general, the locking domain can be any protein capable of forming a dimer. In various embodiments, the locking domain is a protein subunit that can naturally form a dimer with another protein subunit in solution through non-covalent interactions at the interface. In some preferred embodiments, the two protein subunits can be identical in sequence and form a homodimer. In some other cases, the two protein subunits can be different proteins, or two different domains of a single protein derived through engineering, that can form a heterodimer in solution through non-covalent interactions at the interface. Typically, the locking domain is covalently fused to the nanoparticle subunit to which the immunogen polypeptide (e.g., subunit of an HIV-1 Env derived trimer protein) is linked. In some preferred embodiments, the locking domain is selected from dimeric proteins with no more than about 500 amino acids so that it can be encapsulated within a nanoparticle shell. In some embodiments, the locking domain is derived from dimeric proteins with no more than about 400, 300, 250, 200, 150 or fewer amino acids. In some embodiments, the locking domain is derived from dimeric proteins that contains from about 30 to about 100 amino acids. As described herein, the locking domain can be any dimeric protein that is capable of forming an interface through specific interactions such as hydrophobic (van der Waals) contacts, hydrogen bonds, and/or salt bridges. In some embodiments, the locking domain can be any dimeric protein that is capable of forming an interface through interactions of helices, sheets, loops, or any combinations of the abovementioned structural elements. In some embodiments, the locking domain can be any dimeric protein that is capable of forming an interface at which a covalent bond such as a disulfide bond or a specific chemical linking can be engineered. In various embodiments, the affinity between two subunits of the dimer is sufficiently strong to resist external perturbations such as heat and chemical processing that otherwise would not be tolerated by wild-type (WT) nanoparticles lacking such locking domains.

Many proteins known in the art can be employed as the locking domain in the practice of the invention. These include, e.g., the two locking domains LD4 (SEQ ID NO:1) and LD7 (SEQ ID NO:2) exemplified herein in the Examples below. Some other exemplary locking domains suitable for the invention are shown in SEQ ID NOs:3-16. As exemplified herein for HIV-1 vaccines, the HIV-1 nanoparticle UFO trimer vaccines stabilized via locking domain LD4 or LD7 demonstrated surprisingly strong immunogenic properties. In addition to locking domains with any of these exemplified sequences, conservatively modified variants or variants with substantially identical sequences can also be used.

Suitable locking domains can be readily identified from known proteins from Protein database (PDB). For example, dimeric proteins can be found from the protein data bank (PDB) (https://www.rcsb.org/) or other databases using keywords such as "homodimer" or search criteria such as "protein stoichiometry A2". These dimeric proteins can be further filtered based on their size, specifically, 30-100 amino acids. The remaining proteins can be visually inspected to identify those with a compact structural fold or other desirable properties. As exemplified herein, a number of dimeric proteins were identified, and modified as needed as detailed below, using these procedures. Among about 20 dimeric proteins thus identified, 9 were tested as locking domains to stabilize 60-meric nanoparticle E2p and I3-01. The sequences of 9 tested locking domains are listed below. Compared to their original sequences, sequences of the actually employed locking domain (SEQ ID NOs:1-9) may contain truncations of a few residues in the flexible N- and/or C-termini for the engineering purpose. In the case of engineered LD9 (SEQ ID NO:9), in addition to truncations at the N- and C-termini of the original sequence, it also contains a S->A mutation at residue 42.

```
LD1 1NI8_A:
                                          (SEQ ID NO: 3)
SEALKILNNIRTLRAQARECTLETLEEMLEKLEVVVNERR

LD2 4AYA_B:
                                          (SEQ ID NO: 4)
MNDCYSKLKELVPSIPQNKKVSKMEILQHVIDYILDLQIALDSH

LD3 1OVX_A:
                                          (SEQ ID NO: 5)
LLYCSFCGKSQHEVRKLIAGPSVYICDECVDLCNDIIREEIKEVAPHRER

LD4 2MG4_A:
                                          (SEQ ID NO: 1)
FSEEQKKALDLAFYFDRRLTPEWRRYLSQRLGLNEEQIERWFRRKEQQIG
WSHPQFEK

LD5 2JV7_A:
                                          (SEQ ID NO: 6)
DQPSVGDAFDKYNEAVRVFTQLSSAANCDWAACLSSLSASSAACIAAVGE
LGLDVPLDLACAATATSSATEACKGCLW

LD6 1JR5_A:
                                          (SEQ ID NO: 7)
KNIDTVREIITVASILIKFSREDIVENRANFIAFLNEIGVTHEGRKLNQN
SFRKIVSELTQEDKKTLIDEFNEGFEGVYRYLEMYTNK

LD7 1PZQ_A:
                                          (SEQ ID NO: 2)
SPAVDIGDRLDELEKALEALSAEDGHDDVGQRLESLLRRWNSRRAD

LD8 1R2A_A:
                                          (SEQ ID NO: 8)
PPGLTELLQGYTVEVLRQQPPDLVDFAVEYFTRLREARR

LD9 2JRX_A:
                                          (SEQ ID NO: 9)
YSDEQVEQLLAELLNVLEKHKAPTDLSLMVLGNMVTNLINTAIAPAQRQA
IANSFARALQSSINE
```

In addition to these tested LDs, other dimeric proteins with similar structural characteristics may be used to stabilize the nanoparticle surface. Examples of such additional sequences include:

```
1L6E_A:
                                          (SEQ ID NO: 10)
HMGHIQIPPGLTELLQGYTVEVLRQQPPDLVDFAVEYFTRLREARR

1PZR_A:
                                          (SEQ ID NO: 11)
ASDDELFSMLDQRFGGGEDLLMSGDNGMTEEKLRRYLKRTVTELDSVTAR
LREVEHRAGE
```

-continued

1R05_A:
(SEQ ID NO: 12)
MADKRAHHNALERKRRDHIKDSFHSLRDSVPSLQGEKASRAQILDKATEY
IQYMRRKVHTLQQDIDDLKRQNALLEQQVRALEGSGC

1TKV_A:
(SEQ ID NO: 13)
MNKNIDTVREIITVASILIKFSREDIVENRANFIAFLNEIGVTHEGRKLN
QNSFRKIVSELTQEDKKTLIDEFNEGFEGVYRYLEMYTNK

2DSM_A:
(SEQ ID NO: 14)
MVENPMVINNWHDKLTETDVQIDFYGDEVTPVDDYVIDGGEHLRENLERY
LREQLGFEFKNAQLE

2JPQ_A:
(SEQ ID NO: 15)
MPITSKYTDEQVEKILAEVALVLEKHAASPELTLMIAGNIATNVLNQRVA
ASQRKLIAEKFAQALMSSLETPKTHLE

2K01_A:
(SEQ ID NO: 16)
GMKPVSLSYRCPCRFFESHVARANVKHLKILNTPNCACQIVARLKNNNRQ
VCIDPKLKWIQEYLEKCLNK

In addition to these specific LDs and dimeric proteins, other proteins matching the criteria described above, which either already exist or can be readily derived from the protein data bank (PDB), can also be utilized as locking domains in the invention. Furthermore, the interface-forming portion or domain of a large dimeric protein can be used as a stand-alone locking domain if it matches the structural and functional requirements described above.

V. Additional Structural Components or Motifs

Other than the locking domain, the nanoparticle displayed immunogen vaccine constructs and the resulting vaccine compositions of the invention can additionally or alternatively contain other structural components or motifs. In some embodiments, the locking domain stabilized nanoparticle vaccines of the invention also contain a T-cell epitope to promote robust T-cell responses and to steer B cell development towards bNAbs. The T-cell epitope can be located at any position in relation to the other structural components so long as it does not impact presentation of the immunogen polypeptides on the nanoparticle surface. Thus, in some embodiments, the T-cell epitope is located at the C-terminus of the nanoparticle subunit, e.g., by fusing the N-terminus of the T-cell epitope to the C-terminus of the nanoparticle subunit. In some other embodiments, the T-cell epitope is located between C-terminus of the immunogen polypeptide and N-terminus of the nanoparticle subunit. Any T-cell epitope sequences or peptides known in the art may be employed in the practice of the present invention. They include any polypeptide sequence that contain MHC class-II epitopes and can effectively activate CD4+ and CD8+ T cells upon immunization, e.g., T-helper epitope that activates CD4+ T helper cells). See, e.g., Alexander et al., Immunity 1, 751-761,1994; Ahlers et al., J. Clin. Invest. 108:1677-1685, 2001; Fraser et al., Vaccine 32, 2896-2903, 2014; De Groot et al., Immunol. Cell Biol. 8:255-269, 2002; and Gene Ther. 21: 225-232, 2014. In some preferred embodiments, the employed T-helper epitope is the universal pan-reactive T-cell epitope peptide, AKFVAAWTLKAAA (SEQ ID NO:18) (Alexander et al., Immunity 1, 751-761,1994). Other examples of suitable T-cell epitopes include peptides QSIALSSLMVAQAIP (SEQ ID NO:19) and ILMQYI-KANSKFIGIPMGLPQSIALSSLMVAQ (SEQ ID NO:20), or conservatively modified variants or substantially identical (e.g., at least 90%, 95% or 99% identical) sequences of any of these exemplified T-cell epitope peptides.

Alternative or in additional to the locking domain and other structural components described herein, some nanoparticle vaccines of the invention contain a neck region or domain to facilitate display of the immunogen on the surface of nanoparticles. As exemplified herein with PCSK9 vaccine and *P. falciparum* immunogens Pfs25 for malaria vaccine, the neck region constitutes a three-helix bundle derived from a viral protein. Typically, the neck domain is inserted between the immunogen and the nanoparticle subunit, thereby elevating the immunogen polypeptide from the nanoparticle surface. Optionally, a linker sequence (e.g., a 10GS linker) can be used for insertion of the neck domain. Examples of suitable proteins for the neck domain include, helix bundles derived from the Hendra virus domain (PDB ID: 4HEO) and the Measles virus domain (PDB ID: 1OKS) as exemplified herein. As demonstrated, such a structural design can further improve yield and purity of the resulting nanoparticle vaccines.

Alternative or in addition to the locking domain and other structural components described herein, some nanoparticle vaccines of the invention can contain a protein domain that serves to stabilize the immunogen polypeptide. In some embodiments, the employed protein domain to achieve this goal can be the C-terminal trimerization motif of T4 fibritin (foldon) that is well known in the art. This foldon domain constitutes the C-terminal 30 amino acid residues of the trimeric protein fibritin from bacteriophage T4, and functions in promoting folding and trimerization of fibritin. See, e.g., Papanikolopoulou et al., J. Biol. Chem. 279: 8991-8998, 2004; and Guthe et al., J. Mol. Biol. 337: 905-915, 2004. As exemplified herein with the S spike trimer for MERS-CoV vaccine, this protein domain can be readily inserted between S spike subunit and the nanoparticle subunit. An optional linker (e.g., 10GS linker) can be used for the insertion. Unlike the locking domain which is inserted at the C-terminus of the nanoparticle subunit, this protein domain (foldon) is inserted at the N-terminus of the nanoparticle subunit. As demonstrated herein with the MERS-CoV vaccine, such a structural component (e.g., a foldon) when used alone or in combination with a locking domain, can enhance stability of the immunogen that is displayed on the surface of the nanoparticles.

In various embodiments, nanparticles displaying any of the immunogen polypeptides or proteins described herein (e.g., HIV-1 Env-derived trimer immunogens) can be constructed by fusing the immunogen polypeptide or subunit of multimeric immunogen protein (e.g., a trimer immunogen) to the subunit of the nanoparticle (e.g., E2p or I3-01 subunit) and the locking domain, as well as the other optional or alternative components described herein. To construct the nanoparticle displayed fusion vaccine immunogens of the invention, one or more linker motifs or moieties may be employed to facilitate connection and maintain structural integrity of the different components. Thus, in some embodiments, a linker motif can be employed to connect the C-terminus of the immunogen polypeptide (e.g., HIV-1 trimer protein subunit) to the N-terminus of the nanoparticle subunit. Additionally or alternatively, a second linker motif can be used to link the C-terminus of the nanoparticle subunit (or the C-terminus of the immunogen polypeptide) to the N-terminus of the locking domain. In some other embodiments, a third linker motif may be employed to connect the T-cell epitope, e.g., linking the C-terminus of the locking domain to the N-terminus of the T-cell epitope, or linking the C-terminus of the T-cell epitope to the N-terminus of the locking domain. As exemplified herein, linkers can also be used to insert a neck domain or a foldon domain into the nanoparticle vaccine constructs. Typically, the linker motifs contain short peptide sequences. In various embodiments, the linkers or linker motifs can be any flexible peptides that connect two protein domains without interfering with their functions. For example, any of these linkers used in the constructs can be GC-rich peptides with a sequence of $(G_aS_b)_n$, wherein a is an integer of about 1-5, b is an integer of about 0-2, and n is an integer of about 1-5. In some other embodiments, a T-cell epitope can be used as a linker or part of a linker between the C-terminus of the immunogen polypeptide and the N-terminus of the nanoparticle subunit.

The vaccine compositions with novel structural components as described herein (e.g., HIV-1 trimer immunogens stabilized with a locking domain) of the invention can be constructed recombinantly in accordance with the protocols described herein (e.g., Examples 1-15) and/or other methods that have been described in the art, e.g., He et al., Nat. Comm. 7, 12041, 2016; Kong et al., Nat. Comm. 7, 12040, 2016; and He et al., Sci Adv. 4(11):eaau6769, 2018. As exemplification, two specific HIV-1 nanoparticle vaccine constructs are described herein. The first construct expresses a fusion polypeptide that contains from the N-terminus to the C-terminus: HIV-1 UFO BG505.SOSIP.664 gp140 subunit, E2p subunit (e.g., SEQ ID NO:21), a linker motif $(G_aS_b)_n$ noted above (e.g., (GGGGS)$_2$ (SEQ ID NO:24)), the locking domain as shown in SEQ ID NO:1 (LD4), and T-cell epitope (e.g., the PADRE epitope shown in SEQ ID NO:18). Optionally, the immunogen polypeptide (e.g., gp140 subunit for HIV-1 vaccine) can be connected to the nanoparticle subunit (e.g., E2p) via a linker sequence, e.g., GGGGS (SEQ ID NO:17) or (GGGGS)$_2$ (e.g., SEQ ID NO:24). The second construct expresses a fusion polypeptide that contains from the N-terminus to the C-terminus: HIV-1 UFO BG505.SOSIP.664 gp140, a linker sequence (GGGGS)$_2$ (SEQ ID NO:24), I3-01 subunit (e.g., SEQ ID NO:22 or 25), a second linker $(G_aS_b)_n$ noted above (e.g., GGGGS (SEQ ID NO:17)), the locking domain as shown in SEQ ID NO:2 (LD7), and the T-cell epitope (e.g., the epitope as shown in SEQ ID NO:18). Optionally, a dipeptide linker, GS, can be inserted between the locking domain and the T-cell epitope in any of the vaccine constructs of the invention. The antigeniciy and structural integrity of the vaccine immunogens (e.g., HIV-1 nanoparticle immunogens) can be readily analyzed via standard assays, e.g., antibody binding assays and negative-stain electron microscopy (EM). As exemplified herein, the fusion molecules can all self-assemble into nanoparticles that display immunogenic epitopes of the Env-derived trimer (e.g., gp140). By eliciting robust trimer-specific bnAbs, the nanoparticle vaccines of the invention are useful for vaccinating individuals against a broad range of viruses (e.g., HIV-1, Ebola, Lassa, and HCV viruses) as exemplified herein.

VI. Presenting Scaffold

Any heterologous scaffold can be used to present the immunogen protein or polypeptide (e.g., an HIV-1 Env trimer protein) in the construction of the vaccines of the invention. This includes a virus-like particle (VLP) such as bacteriophage Q$_\beta$ VLP and nanoparticles. In some preferred embodiments, the heterologous scaffold for presenting or displaying the trimeric HIV-1 protein is a self-assembling nanoparticle. Various nanoparticle platforms can be employed in generating the vaccine compositions of the invention. In general, the nanoparticles employed in the invention need to be formed by multiple copies of a single subunit. The nanoparticles are typically ball-like shaped, and/or have rotational symetry (e.g., with 3-fold and 5-fold axis), e.g., with an icosahedral structure exemplified herein. Additionally or alternatively, the amino-terminus of the particle subunit has to be exposed and in close proximity to the 3-fold axis, and the spacing of three amino-termini has to closely match the spacing of the carboxyol-termini of various HIV-1 trimeric components. In some preferred embodiments, the immunogens comprise self-assembling naoparticles with a diameter of about 20 nm or less (usually assembled from 12, 24, or 60 sububits) and 3-fold axes on the particle surface. Such nanoparticles provide suitable particle platforms to produce multivalent vaccines, e.g., HIV-1 trimer vaccines as exemplified herein.

In some preferred embodiments, the immunogen protein or polypeptide (e.g., an HIV-1 trimer protein) is presented on self-assembling nanoparticles such as self-assembling nanoparticles derived from ferritin (FR), E2p and I3-01 as exemplified herein. E2p is a redesigned variant of dihydrolipoyl acyltransferase from *Bacillus stearothermophilus* that has been shown to self-assemble into thermostable 60-meric nanoparticle. See, e.g., He et al., *Nat. Commun.* 7:12041, 2016. Similarly, I3-01 is an engineered protein that can self-assemble into hyperstable nanoparticles. See, e.g., Hsia et al., Nature 535, 136-139, 2016. Sequences of the subunits of these proteins are known in the art. See, e.g., WO2017/192434. Amino acid sequences of E2p and I3-01 nanoparticle subunits as exemplified herein are shown in SEQ ID NOs:21 and 22, respectively. Relative to the original sequence, E2p sequence shown in SEQ ID NO:21 contains an Ala substitution at residue 92 as highlighted in the sequence below. In addition to I3-01 subunit sequence shown in SEQ ID NO:22, a redesigned I3-01 subunit sequence shown in SEQ ID NO:25 can also be employed in the practice of the invention. In various embodiments, the HIV-1 nanoparticle vaccines of the invention can employ any of these known nanoparticles, as well as their conservatively modified variants or variants with substantially identical (e.g., at least 90%, 95% or 99% identical) sequences.

E2p subunit sequence (SEQ ID NO: 21)

AAAKPATTEGEFPETREKMSGIRRAIAKAMVHSKHTAPHVTLMDEADVT

KLVAHRKKFKAIAAEKGIKLTFLPYVVKALVSALREYPVLNT<u>A</u>IDDETE

EIIQKHYYNIGIAADTDRGLLVPVIKHADRKPIFALAQEINELAEKARD

GKLTPGEMKGASCTITNIGSAGGQWFTPVINHPEVAILGIGRIAEKPIV

RDGEIVAAPMLALSLSFDHRMIDGATAQKALNHIKRLLSDPELLLM

I3-01 subunit sequence (SEQ ID NO: 22)

MKMEELFKKHKIVAVLRANSVEEAKKKALAVFLGGVHLIEITFTVPDAD

TVIKELSFLKEMGAIIGAGTVTSVEQCRKAVESGAEFIVSPHLDEEISQ

FCKEKGVFYMPGVMTPTELVKAMKLGHTILKLFPGEVVGPQFVKAMKGP

FPNVKFVPTGGVNLDNVCEWFKAGVLAVGVGSALVKGTPVEVAEKAKAF

VEKIRGCTE

-continued

I3-01-z9 variant sequence (SEQ ID NO: 25)

MKMEELFKKHKIVAVLRANSVEEAKMKALAVFVGGVHLIEITFTVPDAD

TVIKELSFLKELGAIIGAGTVTSVEQCRKAVESGAEFIVSPHLDEEISQ

FCKEKGVFYMPGVMTPTELVKAMKLGHTILKLFPGEVVGPQFVKAMKGP

FPNVKFVPTGGVNLDNVCEWFKAGVLAVGVGSALVKGTIAEVAAKAAAF

VEKIRGCTE

Ferritin sequence (SEQ ID NO: 26)

MLSKDIIKLLNEQVNKEMNSSNLYMSMSSWCYTHSLDGAGLFLFDHAAE

EYEHAKKLIIFLNENNVPVQLTSISAPEHKFEGLTQIFQKAYEHEQHIS

ESINNIVDHAIKSKDHATFNFLQWYVAEQHEEEVLFKDILDKIELIGNE

NHGLYLADQYVKGIAKSRKS

In addition to these exemplified nanoparticle sequences, many other nanoparticles or VLPs known in the art may also be used in the practice of the invention. These include, e.g., *Aquifex aeolicus* lumazine synthase, *Thermotoga Maritima* encapsulin, *Myxococcus xanthus* encapsulin, bacteriophage Qbeta virus particle, Flock House Virus (FHV) particle, ORSAY virus particle, and infectious bursal disease virus (IBDV) particle.

As described above, many vaccine immunogens can be used in the vaccine design of the invention. These include various viral immunogens and non-viral proteins. In the case of HIV-1 vaccines, any Env-derived HIV-1 trimer proteins can be used in the nanoparticle-presented vaccine compositions. The Env-derived trimer protein can be obtained from various HIV-1 strains. In some embodiments, the nanoparticles present a native trimeric form of HIV-1 Env based glycoproteins or domains, e.g., gp140, gp120 or V1V2 domains. In some embodiments, the employed HIV-1 Env-derived trimer protein is an uncleaved prefusion-optimized (UFO) gp140 trimer. In some embodiments, the Env-derived trimer is from HIV-1 strain BG505, e.g., the BG505. SOSIP.664 gp140 trimer. In some embodiments, the nanoparticles present a modified gp140 trimer immunogen, e.g., a HR1-modified gp140 trimer ("UFO trimer") described in Kong et al., Nat. Comm. 7, 12040, 2016. The amino acid sequence of subunit of this HR1-modified gp140 trimer protein is shown in SEQ ID NO:23. In some embodiments, the HIV-1 trimeric immunogen used in the invention can be a UFO²-BG trimer. UFO²-BG trimers are chimeric gp140 trimers containing (1) the BG505 gp41 domain with a redesigned HR1 N-terminal bend and a cleavage-site linker (as described in Kong et al., Nat. Comm. 7, 12040, 2016) and (2) the gp120 protein from one of other diverse HIV-1 strains or subtypes. In addition to the redesigned gp41$_{ECTO}$ domain from the BG505 strain, the gp41 domain in the chimeric gp140 trimers suitable for the invention can also be a consensus gp41$_{ECTO}$ domain derived from the HIV-1 sequence database. Also can be used in constructing HIV-1 nanoparticle vaccines of the invention are conservatively modified variants of the various HIV-1 trimer proteins described herein, or variants with substantially identical sequences thereof.

Sequence of HR1-modified gp140 trimer (SEQ ID NO: 23)

AENLWVTVYYGVPVWKDAETTLFCASDAKAYETEKHNVWATHACVPTDPN

PQEIHLENVTEEFNMWKNNMVEQMHTDIISLWDQSLKPCVKLTPLCVTLQ

CTNVTNNITDDMRGELKNCSFNMTTELRDKKQKVYSLFYRLDVVQINENQ

GNRSNNSNKEYRLINCNTSAITQACPKVSFEPIPIHYCAPAGFAILKCKD

KKFNGTGPCPSVSTVQCTHGIKPVVSTQLLLNGSLAEEEVMIRSENITNN

AKNILVQFNTPVQINCTRPNNNTRKSIRIGPGQAFYATGDIIGDIRQAHC

NVSKATWNETLGKVVKQLRKHFGNNTIIRFANSSGGDLEVTTHSFNCGGE

FFYCNTSGLFNSTWISNTSVQGSNSTGSNDSITLPCRIKQIINMWQRIGQ

AMYAPPIQGVIRCVSNITGLILTRDGGSTNSTTETFRPGGGDMRDNWRSE

LYKYKVVKIEPLGVAPTRCKRRVVGGGGGSGGGGSAVGIGAVFLGFLGAA

GSTMGAASMTLTVQARNLLSGNPDWLPDMTVWGIKQLQARVLAVERYLRD

QQLLGIWGCSGKLIC**CTNVPWNSSWSNRNLSEIWDNMTWLQWDKEISNYT

QIIYGLLEESQNQQEKNEQDLLALD

VII. Polynucleotides and Expression Constructs

The vaccine compositions of the invention are typically produced by first generating expression constructs (i.e., expression vectors) that contain operably linked coding sequences of the various structural components described herein. Accordingly, in some related aspects, the invention provides substantially purified polynucleotides (DNA or RNA) that encode the nanoparticle displayed immunogens with novel structural components as described herein (e.g., HIV-1 Env trimer displaying nanoparticles stabilized with locking domain), as well as expression vectors that harbor such polynucleotides (e.g., CMV vectors exemplified herein) and host cells for producing the vaccine immunogens (e.g., ExpiCHO cells exemplified herein). The fusion polypeptides encoded by the polynucleotides or expressed from the vectors are also included in the invention. As described herein, such polypeptides will self-assemble into nanoparticle vaccines that display the immunogen polypeptides or proteins on its surface.

The polynucleotides and related vectors can be readily generated with standard molecular biology techniques or the protocols exemplified herein. For example, general protocols for cloning, transfecting, transient gene expression and obtaining stable transfected cell lines are described in the art, e.g., Sambrook et al., Molecular Cloning: A Laboratory Manual, Cold Spring Harbor Press, N.Y., (3$^{rd}$ ed., 2000); and Brent et al., Current Protocols in Molecular Biology, John Wiley & Sons, Inc. (ringbou ed., 2003). Introducing mutations to a polynucleotide sequence by PCR can be performed as described in, e.g., *PCR Technology: Principles and Applications for DNA Amplification*, H. A. Erlich (Ed.), Freeman Press, NY, N.Y., 1992; *PCR Protocols: A Guide to Methods and Applications*, Innis et al. (Ed.), Academic Press, San Diego, Calif., 1990; Manila et al., Nucleic Acids Res. 19:967, 1991; and Eckert et al., PCR Methods and Applications 1:17, 1991.

The selection of a particular vector depends upon the intended use of the fusion polypeptides. For example, the selected vector must be capable of driving expression of the fusion polypeptide in the desired cell type, whether that cell type be prokaryotic or eukaryotic. Many vectors contain sequences allowing both prokaryotic vector replication and eukaryotic expression of operably linked gene sequences.

Vectors useful for the invention may be autonomously replicating, that is, the vector exists extrachromosomally and its replication is not necessarily directly linked to the replication of the host cell's genome. Alternatively, the replication of the vector may be linked to the replication of the host's chromosomal DNA, for example, the vector may be integrated into the chromosome of the host cell as achieved by retroviral vectors and in stably transfected cell lines. Both viral-based and nonviral expression vectors can be used to produce the immunogens in a mammalian host cell. Nonviral vectors and systems include plasmids, episomal vectors, typically with an expression cassette for expressing a protein or RNA, and human artificial chromosomes (see, e.g., Harrington et al., Nat. Genet. 15:345, 1997). Useful viral vectors include vectors based on lentiviruses or other retroviruses, adenoviruses, adenoassociated viruses, Cytomegalovirus, herpes viruses, vectors based on SV40, papilloma virus, HBP Epstein Barr virus, vaccinia virus vectors and Semliki Forest virus (SFV). See, Brent et al., supra; Smith, Annu. Rev. Microbiol. 49:807, 1995; and Rosenfeld et al., Cell 68:143, 1992.

Depending on the specific vector used for expressing the fusion polypeptide, various known cells or cell lines can be employed in the practice of the invention. The host cell can be any cell into which recombinant vectors carrying a fusion of the invention may be introduced and wherein the vectors are permitted to drive the expression of the fusion polypeptide is useful for the invention. It may be prokaryotic, such as any of a number of bacterial strains, or may be eukaryotic, such as yeast or other fungal cells, insect or amphibian cells, or mammalian cells including, for example, rodent, simian or human cells. Cells expressing the fusion polypeptides of the invention may be primary cultured cells or may be an established cell line. Thus, in addition to the cell lines exemplified herein (e.g., CHO cells), a number of other host cell lines capable well known in the art may also be used in the practice of the invention. These include, e.g., various Cos cell lines, HeLa cells, HEK293, AtT20, BV2, and N18 cells, myeloma cell lines, transformed B-cells and hybridomas.

The use of mammalian tissue cell culture to express polypeptides is discussed generally in, e.g., Winnacker, *From Genes to Clones*, VCH Publishers, N.Y., N.Y., 1987. The fusion polypeptide-expressing vectors may be introduced to the selected host cells by any of a number of suitable methods known to those skilled in the art. For the introduction of fusion polypeptide-encoding vectors to mammalian cells, the method used will depend upon the form of the vector. For plasmid vectors, DNA encoding the fusion polypeptide sequences may be introduced by any of a number of transfection methods, including, for example, lipid-mediated transfection ("lipofection"), DEAE-dextran-mediated transfection, electroporation or calcium phosphate precipitation. These methods are detailed, for example, in Brent et al., supra. Lipofection reagents and methods suitable for transient transfection of a wide variety of transformed and non-transformed or primary cells are widely available, making lipofection an attractive method of introducing constructs to eukaryotic, and particularly mammalian cells in culture. For example, LipofectAMINE™ (Life Technologies) or LipoTaxi™ (Stratagene) kits are available. Other companies offering reagents and methods for lipofection include Bio-Rad Laboratories, CLONTECH, Glen Research, Life Technologies, JBL Scientific, MBI Fermentas, PanVera, Promega, Quantum Biotechnologies, Sigma-Aldrich, and Wako Chemicals USA.

For long-term, high-yield production of recombinant fusion polypeptides, stable expression is preferred. Rather than using expression vectors which contain viral origins of replication, host cells can be transformed with the fusion polypeptide-encoding sequences controlled by appropriate expression control elements (e.g., promoter, enhancer, sequences, transcription terminators, polyadenylation sites, etc.), and selectable markers. The selectable marker in the recombinant vector confers resistance to the selection and allows cells to stably integrate the vector into their chromosomes. Commonly used selectable markers include neo, which confers resistance to the aminoglycoside G-418 (Colberre-Garapin, et al., J. Mol. Biol., 150:1, 1981); and hygro, which confers resistance to hygromycin (Santerre et al., Gene, 30: 147, 1984). Through appropriate selections, the transfected cells can contain integrated copies of the fusion polypeptide encoding sequence.

VIII. Pharmaceutical Compositions and Therapeutic Applications

In another aspect, the invention provides pharmaceutical compositions and related therapeutic methods of using the nanoparticle vaccine compositions with novel structural components (e.g., locking domain) as described herein. In some embodiments, the HIV-1 Env trimer vaccine compositions can be used for preventing and treating HIV-1 infections. In various other embodiments, the nanoparticle vaccines containing different viral or non-viral immunogens described herein can be employed to prevent or treat the corresponding diseases, e.g., infections caused by the various pathogens. Some embodiments of the invention relate to use of the EBOV vaccines for preventing or treating Ebola viral infections. Some embodiments of the invention relate to use of the LASV vaccines for preventing or treating Lassa viral infections. Some other embodiments of the invention are directed to using the RSV vaccines described herein for preventing or treating RSV infections. Some other embodiments of the invention are directed to using the HCV vaccines described herein for preventing or treating HCV infections. Still some other embodiments of the invention are directed to using the CoV vaccines described herein for preventing or treating MERS-CoV infections. In some other embodiments, the invention provides methods of using the ZIKV vaccines for preventing or treating Zika viral infections. In some other embodiments, the invention provides methods of using the *P. falciparum* immunogen (e.g., Pfs25) derived vaccines for preventing or treating malaria. In some other embodiments, the invention provides methods of using the vaccines derived from *M. tuberculosis* immunogen Ag85A or Mtb72 for preventing or treating tuberculosis. In still some other embodiments, the invention provides methods of using the PCSK9 vaccine to lower LDL cholesterol in human subjects.

In the practice of the various therapeutic methods of the invention, the subjects in need of prevention or treatment of a disease or condition (e.g., HIV-1 infection or malaria) is administered with the corresponding nanoparticle vaccine, the immunogen polypeptide or an encoding polynucleotide described herein. Typically, the nanoparticle vaccine, the immunogen polypeptide or the encoding polynucleotide disclosed herein is included in a pharmaceutical composition. The pharmaceutical composition can be either a therapeutic formulation or a prophylactic formulation. Typically, the composition additionally includes one or more pharmaceutically acceptable vehicles and, optionally, other therapeutic ingredients (for example, antibiotics or antiviral drugs). Various pharmaceutically acceptable additives can also be used in the compositions.

Thus, some of the pharmaceutical compositions of the invention are vaccine compositions. For vaccine compositions, appropriate adjuvants can be additionally included. Examples of suitable adjuvants include, e.g., aluminum hydroxide, lecithin, Freund's adjuvant, MPL™ and IL-12. In some embodiments, the vaccine compositions or nanoparticle immunogens disclosed herein (e.g., HIV-1 vaccine or malaria vaccine composition) can be formulated as a controlled-release or time-release formulation. This can be achieved in a composition that contains a slow release polymer or via a microencapsulated delivery system or bioadhesive gel. The various pharmaceutical compositions can be prepared in accordance with standard procedures well known in the art. See, e.g., Remington's Pharmaceutical Sciences, 19$^{th}$ Ed., Mack Publishing Company, Easton, Pa., 1995; Sustained and Controlled Release Drug Delivery Systems, J. R. Robinson, ed., Marcel Dekker, Inc., New York, 1978); U.S. Pat. Nos. 4,652,441 and 4,917,893; U.S. Pat. Nos. 4,677,191 and 4,728,721; and U.S. Pat. No. 4,675,189.

The pharmaceutical compositions of the invention can be readily employed in a variety of therapeutic or prophylactic applications, e.g., for treating HIV-1 infection or malaria, or eliciting an immune response to HIV-1 or *P. falciparum* in a subject. In various embodiments, the vaccine compositions can be used for treating or preventing infections caused by a pathogen from which the displayed immunogen polypeptide in the nanoparticle vaccine is derived. Thus, the vaccine compositions of the invention can be used in diverse clinical settings for treating or preventing infections caused by various viruses (e.g., HIV-1, Ebola virus, Marburg virus, Lassa virus, RSV, MERS-CoV, SARS-CoV, HCV, Dengue virus, or Zika virus) or other pathogens (e.g., bacteria such as *Mycobacterium tuberculosis* and parasitic organisms such as *Plasmodium falciparum*). They can also be used for inducing a desired immune response against endogenous targets in mammalian subjects (e.g., human), e.g., eliciting antibody responses against PCSK9 or ghrelin. Unless otherwise noted, the disclosure provided herein to exemplify therapeutic applications of HIV-1 vaccine compositions can be similarly applied to nanoparticle vaccines displaying any other viral or non-viral immunogens.

As exemplification, an HIV-1 nanoparticle vaccine composition can be administered to a subject to induce an immune response to HIV-1, e.g., to induce production of broadly neutralizing antibodies to HIV-1. For subjects at risk of developing an HIV infection, a vaccine composition of the invention can be administered to provide prophylactic protection against viral infection. Therapeutic and prophylactic applications of vaccines derived from the other immunogens described herein can be similarly performed. Depending on the specific subject and conditions, pharmaceutical compositions of the invention can be administered to subjects by a variety of administration modes known to the person of ordinary skill in the art, for example, intramuscular, subcutaneous, intravenous, intra-arterial, intra-articular, intraperitoneal, or parenteral routes. In general, the pharmaceutical composition is administered to a subject in need of such treatment for a time and under conditions sufficient to prevent, inhibit, and/or ameliorate a selected disease or condition or one or more symptom(s) thereof. The immunogenic composition is administered in an amount sufficient to induce an immune response against HIV-1. For therapeutic applications, the compositions should contain a therapeutically effective amount of the HIV-1 nanoparticle immunogen described herein. For prophylactic applications, the compositions should contain a prophylactically effective amount of the HIV-1 nanoparticle immunogen described herein. The appropriate amount of the immunogen can be determined based on the specific disease or condition to be treated or prevented, severity, age of the subject, and other personal attributes of the specific subject (e.g., the general state of the subject's health and the robustness of the subject's immune system). Determination of effective dosages is additionally guided with animal model studies followed up by human clinical trials and is guided by administration protocols that significantly reduce the occurrence or severity of targeted disease symptoms or conditions in the subject.

For prophylactic applications, the immunogenic composition is provided in advance of any symptom, for example in advance of infection. The prophylactic administration of the immunogenic compositions serves to prevent or ameliorate any subsequent infection. Thus, in some embodiments, a subject to be treated is one who has, or is at risk for developing, an infection (e.g., HIV infection), for example because of exposure or the possibility of exposure to the virus (e.g., HIV infection). Following administration of a therapeutically effective amount of the disclosed therapeutic compositions, the subject can be monitored for an infection (e.g., HIV-1 infection), symptoms associated with an infection (e.g., HIV-1 infection), or both.

For therapeutic applications, the immunogenic composition is provided at or after the onset of a symptom of disease or infection, for example after development of a symptom of infection (e.g., HIV-1 infection), or after diagnosis of the infection. The immunogenic composition can thus be provided prior to the anticipated exposure to HIV virus so as to attenuate the anticipated severity, duration or extent of an infection and/or associated disease symptoms, after exposure or suspected exposure to the virus, or after the actual initiation of an infection.

The pharmaceutical composition of the invention can be combined with other agents known in the art for treating or preventing infections by a relevant pathogen (e.g., HIV infection). Again, using HIV-1 infection as exemplification, these known agents include, e.g., antibodies or other antiviral agents such as nucleoside reverse transcriptase inhibitors, such as abacavir, AZT, didanosine, emtricitabine, lamivudine, stavudine, tenofovir, zalcitabine, zidovudine, and the like, non-nucleoside reverse transcriptase inhibitors, such as delavirdine, efavirenz, nevirapine, protease inhibitors such as amprenavir, atazanavir, indinavir, lopinavir, nelfinavir, osamprenavir, ritonavir, saquinavir, tipranavir, and the like, and fusion protein inhibitors such as enfuvirtide and the like. Administration of the pharmaceutical composition and the known anti-HIV agents can be either concurrently or sequentially.

The nanoparticle vaccine compositions containing novel structural components as described in the invention (e.g., HIV-1 vaccine stabilized with locking domain) or pharmaceutical compositions of the invention can be provided as components of a kit. Optionally, such a kit includes additional components including packaging, instructions and various other reagents, such as buffers, substrates, antibodies or ligands, such as control antibodies or ligands, and detection reagents. An optional instruction sheet can be additionally provided in the kits.

EXAMPLES

The following examples are offered to illustrate, but not to limit the present invention.

Example 1

Yield and Purity of BG505 gp140 Nanoparticles with Various LDs

Figure 6:
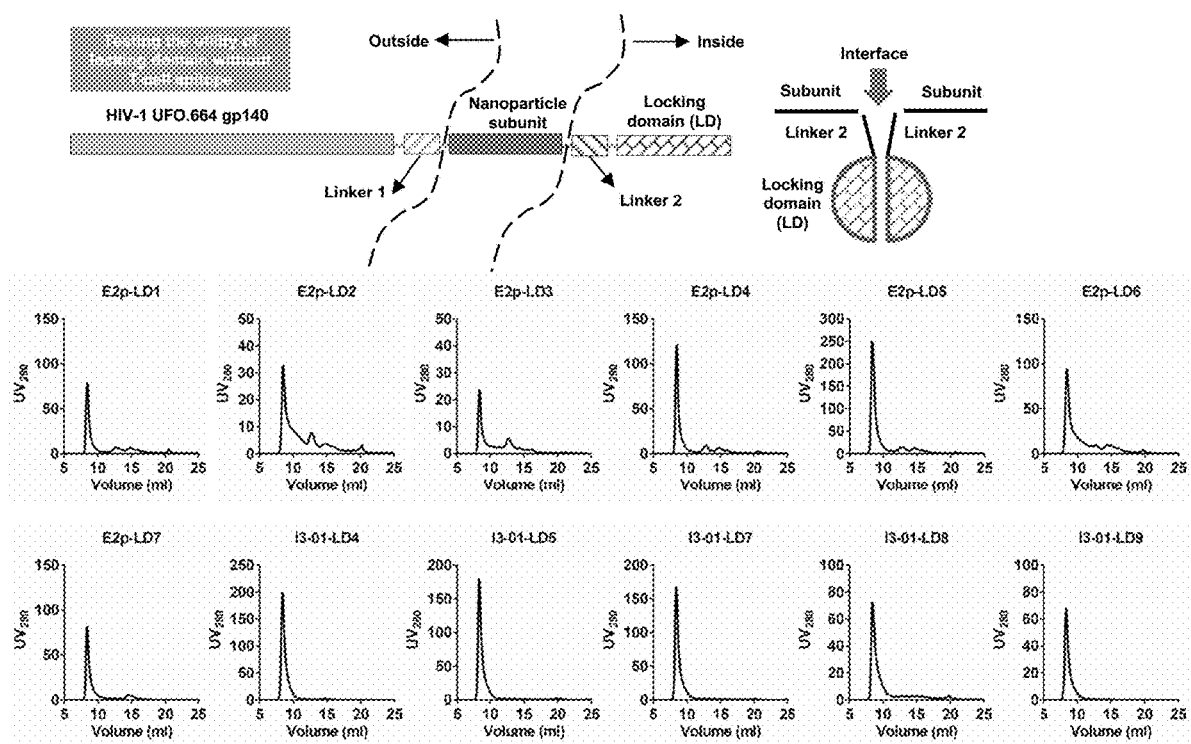
FIG. 6 shows schematically the construct design of HIV-1 nanoparticle immunogens stabilized with different locking domains, as well as size exclusion chromatography (SEC) profiles showing yield and purity of the vaccine immunogens transiently expressed in ExpiCHO cells.

The utility of different locking domains (LDs) was validated for 60-meric E2p and I3-01 nanoparticles, with the HIV-1 BG505 UFO trimers displayed on the surface. The construct design is depicted schematically in FIG. 6. The LD-containing nanoparticles were expressed transiently in 100 mL ExpiCHO cells followed by purification using a 2G12 or a PGT145 antibody column. The nanoparticle samples were then characterized by size exclusion chromatography (SEC) on a Superose 6 10/300 GL column for their yield and purity. The SEC profiles indicated that most LDs can stabilize HIV-1 BG505 UFO gp140 nanoparticles, with varying degrees of yield and purity. For E2p, LD4 and LD5 produced greater yield of high-quality BG505 UFO gp140 nanoparticles than other LDs, while for I3-01, LD4, LD5 and LD7 outperformed other LDs in terms of nanoparticle yield and purity. Of note, E2p-$LD_x$ nanoparticles were purified by a 2G12 antibody column, which also extracted partially assembled nanoparticles and single trimers from the supernatant, whereas I3-01-$LD_x$ nanoparticles were purified by a PGT145 antibody column, which is highly specific to fully assembled nanoparticles. Thus, the difference in purity between E2p-$LD_x$ and I3-01-$LD_x$ was caused by the antibody column used in purification, not by the nanoparticle platform or the LD design.

Example 2

Structural Assembly of BG505 gp140 Nanoparticles with Various LDs

Figure 7:
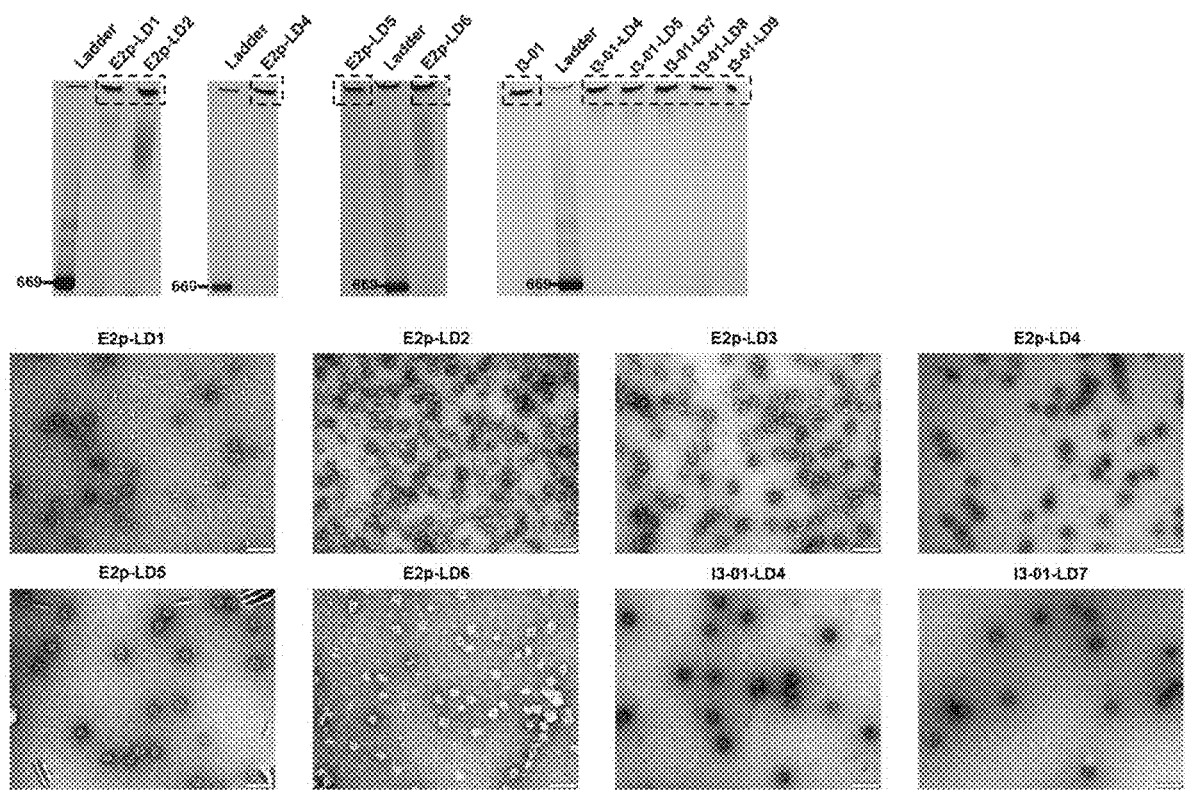
FIG. 7 shows blue native polyacrylamide gel electrophoresis (BN-PAGE) analysis of HIV-1 nanoparticle immunogens stabilized with different locking domains, and negative-stain electron microscopy (EM) images of some well-formed nanoparticles.

To further validate the assembly of LD-containing HIV-1 BG505 gp140 nanoparticles, we first analyzed E2p-$LD_x$ and I3-01-$LD_x$ nanoparticles by blue native polyacrylamide gel electrophoresis (BN-PAGE). The results are shown in FIG. 7. As expected, BN-PAGE did not show any low-molecular-weight bands and confirmed that all samples were trapped in the well at the top of a lane due to the large size and high molecular weight of nanoparticles. Selected E2p-$LD_x$ and I3-01-$LD_x$ constructs were analyzed by negative-stain electron microscopy (EM), which showed well-formed nanoparticles. In the raw EM images, E2p-$LD_x$ nanoparticles were sometimes mixed with single trimers or partially assembled nanoparticles, due to the use of a less stringent antibody column. Nonetheless, BN-PAGE and negative-stain EM analyses demonstrated that locking domains can effectively stabilize two large nanoparticle platforms for displaying native-like HIV-1 gp140 trimers.

Example 3

Design of HIV-1 Nanoparticle Vaccine with Lock Mechanism

Figure 2:
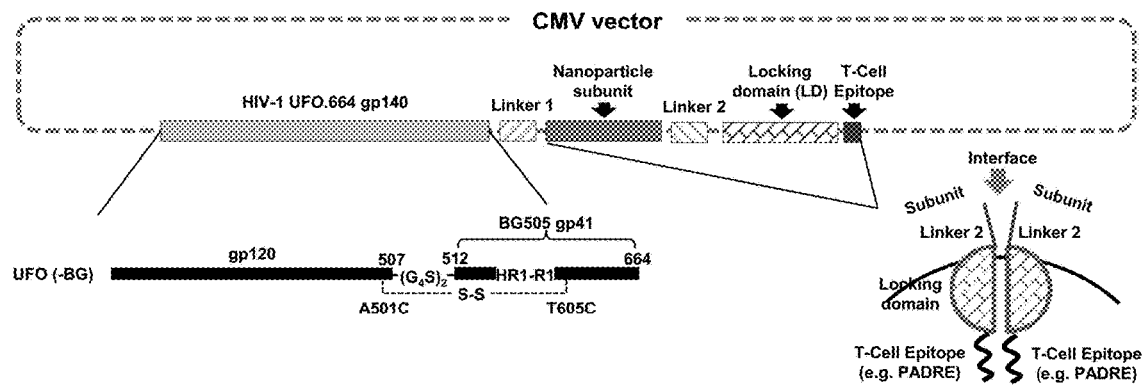
FIG. 2 shows schematically the structure of a CMV vector expressing an example of the locking domain stabilized HIV-1 nanoparticle immunogens described herein.

Two constructs were selected as the $1^{st}$-generation vaccine constructs, each encoding a BG505 UFO.664 gp140, a 10-aa GS linker (for I3-01 only), a nanoparticle subunit (either E2p or I3-01), a 5-aa GS linker, a locking domain (LD) that stabilizes nanoparticle backbone upon self-assembly, and a pan-reactive T-cell epitope (PADRE epitope) that induces a strong T-follicular helper (Tfh) response to guide B cell development toward bNAbs. The DNA plasmids were designed based on a CMV vector commonly used for mammalian expression, with the "antigen" gene inserted into the vector (FIG. 2). These two nanoparticle constructs are named "UFO-E2p-LD4-PADRE" and "UFO-10GS-I3-01-LD7-PADRE". The locking mechanism is depicted schematically in the right corner of FIG. 2. Briefly, the N-terminus of a dimeric LD protein is fused to the C-terminus of a nanoparticle subunit. During self-assembly, when two nanoparticle subunits come together to form a dimeric interface, they will bring their attached LDs to a close vicinity to form a second and much stronger interface just beneath the nanoparticle shell, which significantly enhances its stability.

Example 4

Production of Nanoparticle Vaccines with the Locking Mechanism

The vaccines are purified nanoparticle proteins, which are mixed with adjuvant in a solution phase. The protein material can be produced in either transient ExpiCHO cells or stabilized CHO-S cells in a GMP facility. The manufacturing processes involves three steps: expression in CHO cells, purification by a PGT145 affinity column, and quality control (QC).

In a laboratory-scale production, UFO gp140 nanoparticles are transiently expressed in ExpiCHO cells (Thermo Fisher). Briefly, ExpiCHO cells are thawed and incubated with ExpiCHO™ Expression Medium (Thermo Fisher) in a shaker incubator at 37° C., with 135 rpm and 8% $CO_2$. When the cells reach a density of $10 \times 10^6$ $ml^{-1}$, ExpiCHO™ Expression Medium is added to reduce cell density to $6 \times 10^6$ $ml^{-1}$ for transfection. The ExpiFectamine™ CHO/plasmid DNA complexes are prepared for 100 ml transfection in ExpiCHO cells following the manufacturer's instructions. A total of 100 µg of plasmid and 320 µl of ExpiFectamine™ CHO reagent are mixed in 7.7 ml of cold OptiPRO™ medium (Thermo Fisher). After the first feed on day 1, ExpiCHO cells are cultured in a shaker incubator at 32° C., with 120 rpm and 8% $CO_2$ following the Max Titer protocol with an additional feed on day 5 (Thermo Fisher). Culture supernatants are harvested 13 to 14 days after transfection, clarified by centrifugation at 4000 rpm for 20 min, and filtered using a 0.45 µm filter (Thermo Fisher). Nanoparticles can be extracted from the culture supernatants using a PGT145 antibody affinity column. The plasmid DNA seeds can be prepared by our lab and provided to Contractor for large-scale production in the Contractor's GMP production facility.

Example 5

Quality Control of Nanoparticle Vaccines with the Locking Mechanism

The quality of CHO/ExpiCHO-produced nanoparticle protein can be assessed by (1) a Superose 6 10/300 GL column and blue native polyacrylamide gel electrophoresis (BN-PAGE) for yield and purity; (2) differential scanning calorimetry (DSC) on a MicroCal VP-Capillary calorimeter (Malvern) for thermal stability; (3) bio-layer interferometry (BLI) using Octet RED96, quantitation biosensors, and a panel of bNAbs and non-NAbs for antigenicity; and (4) negative-stain electron microscopy (EM) for nanoparticle assembly and structural integrity. The QC process has been validated in our lab for selected nanoparticle constructs (see below). Of note, QC steps (1)-(2) can be readily performed on site in any GMP facility following protein expression, production, and purification.

Figure 3:
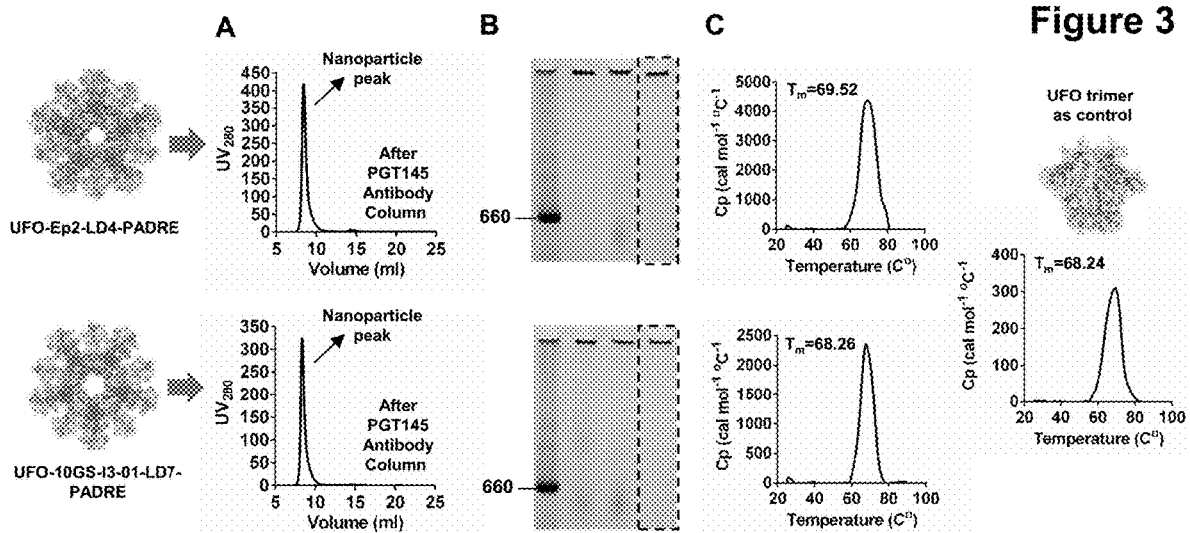
FIG. 3 shows results of quality assessment of CHO/ExpiCHO-produced nanoparticle proteins via several assays. (A): Analysis by size-exclusion chromatography (SEC) on a Superose 6 10/300 GL column. (B): Analysis by BN-PAGE. (C): Assessment by DSC to measure thermal stability.

After transient expression in 100 ml ExpiCHO cells and purification from the cell supernatants using a PGT145 antibody affinity column, nanoparticles were analyzed by size-exclusion chromatography (SEC) on a Superose 6 10/300 GL column (FIG. 3A). A single sharp peak at 8 ml was observed in SEC profiles, indicating a high purity for both constructs. Furthermore, the $UV_{280}$ value reached ~450 and ~350 for E2p- and I3-01-based constructs, respectively, indicating a high yield for both constructs, estimated to be 15-20 mg/L. Of particular note, the locking mechanism could improve not only the stability but also the yield of pure nanoparticles, by 2~3-fold for I3-01 and E2p. The pre-SEC nanoparticle samples were also analyzed by BN-PAGE, which showed no bands corresponding to low-molecular-weight species on the gel, with all samples trapped in the well at the top of a lane due to the large size and high molecular weight of nanoparticles (FIG. 3B). BN-PAGE thus confirmed the high purity observed in SEC analysis.

Purified nanoparticles were then assessed by DSC to measure thermal stability, which yielded melting temperatures ($T_m$) of 69.52 and 68.26° C. for E2p- and I3-01-based constructs, respectively, indicating a high degree of thermal stability comparable to that of the BG505 UFO trimer, $T_m$=68.24° C. (FIG. 3C). Thus, with the locking mechanism, $T_m$ is independent of the nanoparticle platform and is only determined by the thermal stability of displayed antigens, in this case, UFO gp140 trimers. The two selected nanoparticle constructs have also been found resistant to chemicals and stable in a wide temperature range of –80° C. to 4° C. For example, when the frozen-then-thawed samples or samples stored at 4° C. for weeks were analyzed by negative-stain EM, no disintegration due to temperature change was observed.

The structure and antigenicity of GMP-produced nanoparticles were further characterized as described below.

Example 6

Evaluation of Antigenicity and Immunogenicity

In addition to a simple, robust manufacturing process and superb biochemical and biophysical properties, further in-vitro and in-vivo evaluation indicated that these UFO gp140 nanoparticles with the locking mechanism may provide by far the most promising HIV-1 vaccine candidates.

Figure 4:
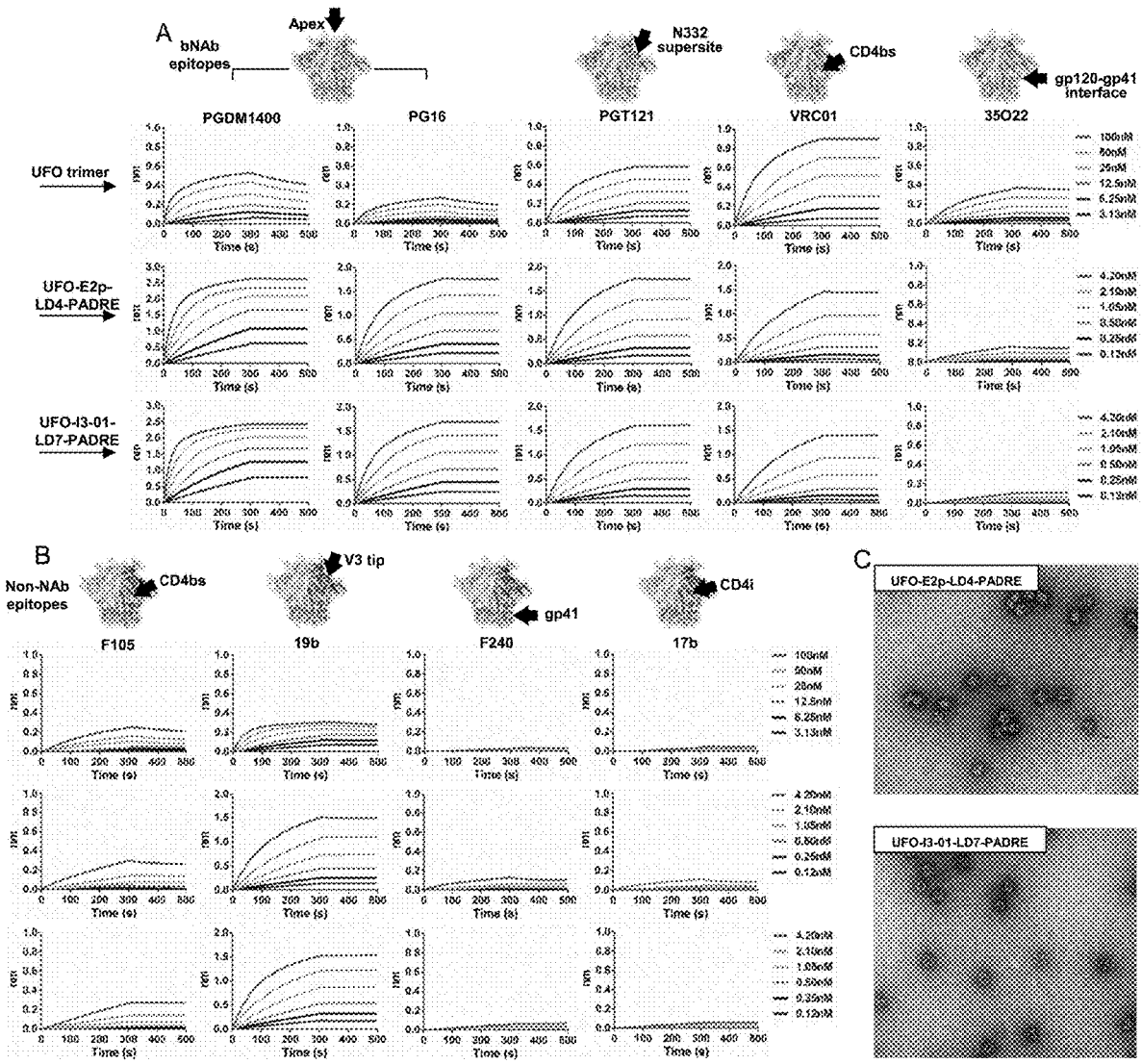
FIG. 4 shows in vitro evaluation of antigenic and structural analyses of two locking domain stabilized HIV-1 nanoparticle immunogens. (A) and (B): Assessment for antibody binding using BLI and a panel of 5 bNAbs (A) and 4 non-NAbs (B). (C): Structural analysis by negative-stain EM (C).

In-vitro evaluation—antigenic and structural analyses (or QC steps 3 and 4): The two selected nanoparticles were assessed for antibody binding using BLI and a panel of 5 bNAbs (FIG. 4A) and 4 non-NAbs (FIG. 4B). The UFO trimer was included as a control. Overall, both nanoparticles showed significantly enhanced binding (by 3-4-fold) to bNAbs recognizing the V2 apex, the N332 supersite, and the CD4bs, but reduced binding to the gp120-gp41 interface by 35O22, which is likely due to the occluded access to this site on the nanoparticle surface. It is also worth noting that nanoparticle display does not increase non-NAb binding to the CD4bs, the CD4i site, and the immunodominant gp41 epitope except for the V3 tip, which showed moderately increased 19b binding.

The two selected nanoparticles were also analyzed structurally by negative-stain EM, which showed well-formed, homogeneous nanoparticles with a dense layer of native-like UFO gp140 trimers protruding from the surface (FIG. 4C). Of note, in most of the cases the locking domains (LDs) within the nanoparticle shell were not visible at this low resolution. However, occasionally once could recognize structures protruding inwardly from the nanoparticle surface, which correspond to the LD proteins.

Figure 5:
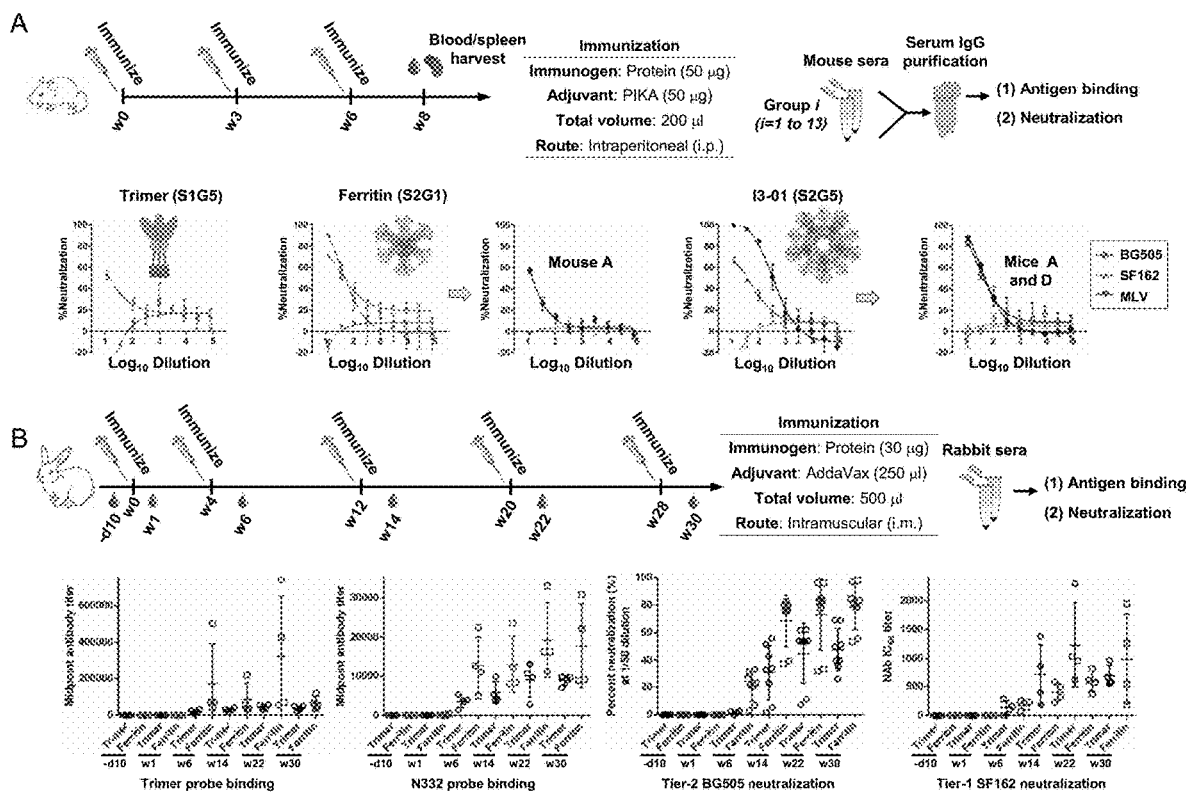
FIG. 5 shows in vivo study of immunogenic activities of two exemplified locking domain stabilized HIV-1 nanoparticle immunogens in mice and rabbits. (A): Induction of autologous tier-2 NAbs in mice by a ferritin nanoparticle and an I3-01 nanoparticle at week 8. (B): Evaluation of immunogenicity of UFO trimer and ferritin nanoparticle in rabbits.

In-vivo evaluation in small animal models: We have assessed a subset of UFO trimers and nanoparticles in mice and rabbits. In mice, all trimers (except for a scaffolded gp140.681 construct) failed to elicit autologous tier-2 NAbs. A ferritin nanoparticle and an early version of the I3-01 nanoparticle design (termed "UFO-PADRE-I3-01") induced autologous tier-2 NAbs at week 8, with a stronger response observed for I3-01 (FIG. 5A). The TZM-b1 HIV neutralization assays were performed using purified IgGs to eliminate non-specific antiviral activity in mouse sera. Of note, this is the first observation of Env-induced tier-2 NAb responses in WT mice, whereas in a previous study BG505 SOSIP trimer failed to elicit any autologous tier-2 NAb response in WT mice after 16 weeks of immunization. The immunogenicity of UFO trimer and ferritin nanoparticle was also evaluated in rabbits, with antibody responses measured longitudinally. The results indicated that ferritin nanoparticle induced autologous tier-2 NAbs at week 8, whereas BG505 UFO trimer needed another 2 months to induce such tier-2 NAb responses (FIG. 5B). In a recent study, the Zhu lab immunized WT mice with one of the final nanoparticle constructs, UFO-E2p-LD4-PADRE. Of the 8 mice tested, one showed a much stronger tier-2 NAb response than others, while all animals exhibited tier-2 NAb responses with 50-95% neutralization at an IgG concentration of 1 mg/ml at week 11 (data not shown). Therefore, the in-vivo data has unambitiously demonstrated the vaccine potential of our UFO gp140 nanoparticles, even though the final nanoparticle vaccine constructs with the locking mechanism have yet to be assessed in vivo. We anticipate that these two nanoparticle constructs will induce a more broad and potent neutralizing antibody response to those tier-2 isolates.

Example 7

Vaccines for Other Viruses Utilizing Class-I Fusion—Filoviruses

We developed nanoparticle vaccines for Filoviruses. Filoviruses such as Ebola viruses (EBOV) and Marburg viruses can cause lethal hemorrhagic fever in humans and nonhuman primates (NHPs). While filoviruses have caused past outbreaks of human disease, Ebola virus was solely responsible for the largest outbreak in history during 2013-2016, which spread across nine African countries with 28,600 cases and 11,325 deaths. Currently, there is an ongoing Ebola outbreak in the Democratic Republic of The Congo (DRC) that has claimed over six hundred lives. Filovirus glycoprotein (GP) mediates cell entry by initiating attachment and membrane fusion and is the main target for vaccine design. GP can be recognized by neutralizing antibodies isolated from human survivors and immunized animals (see Saphire et al., Cell 174(4):938-952, 2018).

Figure 8:
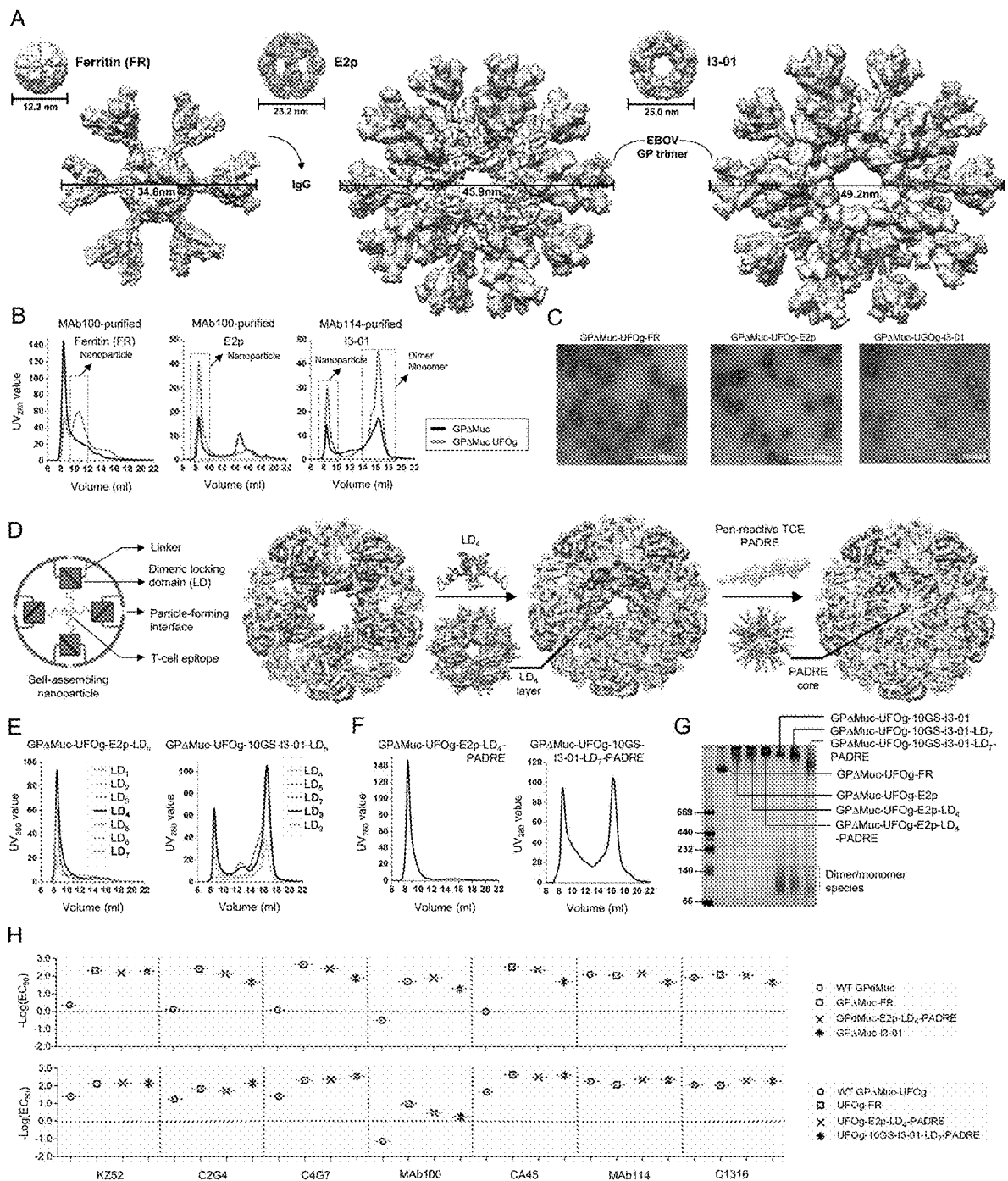
FIG. 8 shows molecular models, size exclusion chromatography (SEC), and negative-stain EM images of Ebola GPΔMuc trimer-presenting nanoparticles, followed by the design concept and molecular models, biochemical and biophysical analyses such as SEC and blue native polyacrylamide gel electrophoresis (BN-PAGE), and antigenic characterization such as ELISA for Ebola GPΔMuc trimer-presenting nanoparticles with various locking domains. SEC profiles are shown for LD1-LD7 in combination with E2p and for LD4-LD9 in combination with I3-01, all presenting Ebola GPΔMuc-UFOg trimers. (A): Display of wild-type (WT) GPΔMuc and a generic UFO (UFOg) form of GPΔMuc on ferritin, E2p, and I3-01 nanoparticle platforms. (B): SEC profiles showing greater yield and purity for the nanoparticles presenting GPΔMuc-UFOg than those presenting WT GPΔMuc. (C): Negative-stain EM of ferritin, E2p, and I3-01 nanoparticles presenting WT GPΔMuc trimers and GPΔMuc-UFOg trimers. (D): Atomic model for E2p nanoparticle incorporating a locking domain (LD4) and a T-cell epitope (PADRE) in a step-wise manner. (E): Yield and purity of seven GPΔMuc-UFOg-E2p-LDn constructs and five GPΔMuc-UFOg-10GS-I3-01-LDn constructs. (F): Improved yield and purity of GPΔMuc-UFOg nanoparticles with a T-cell epitope added to the C-terminus of the locking domain. (G): BN-PAGE confirmation of nanoparticle assembly. (H): Comparison of antigenic profiles of WT GPΔMuc nanoparticles and GPΔMuc-UFOg nanoparticles to their respective GPΔMuc trimers in ELISA.

In our study, we used the amino acid sequence of a Zaire strain (GenBank: NP_066246) of Ebola virus to design various GP fusion constructs, which contain the ectodomain of GP (amino acids 33-632) but delete the unstructured mucin-like domain (MLD, amino acids 313-463), therefore termed GPΔMuc. Since the GPΔMuc form of GP has been widely used in structural studies (see Lee et al., Nature 454(7201):177-182, 2008), it provides a rational basis for filovirus vaccine design. We have displayed wild-type (WT) GPΔMuc and a generic UFO (UFOg) form of GPΔMuc on ferritin, E2p, and I3-01 nanoparticle platforms (FIG. 8A). After transient expression in ExpiCHO cells, the fusion proteins were extracted from the supernatants using an MAb100 antibody column (for ferritin and E2p) or an MAb114 antibody column (for I3-01) prior to purification on a Superose 6 10/300 column. Overall, we observed greater yield and purity for the nanoparticles presenting GPΔMuc-UFOg than those presenting WT GPΔMuc, as indicated by the SEC profiles (FIG. 8B). For ferritin, GPΔMuc-UFOg-ferritin showed a more pronounced peak of nanoparticles than WT GPΔMuc-ferritin. For E2p, WT GPΔMuc-E2p showed peaks of nanoparticles and unassembled proteins, while GPΔMuc-UFOg-E2p showed primarily a high peak of nanoparticles. For I3-01, both fusion constructs appeared to have difficulties in nanoparticle assembly, with high peaks of unassembled fusion proteins at 15-16 ml in the SEC profiles. Nonetheless, negative-stain EM demonstrated well-formed ferritin, E2p, and I3-01 nanoparticles presenting WT GPΔMuc trimers and GPΔMuc-UFOg trimers (FIG. 8C).

Previously, we have systematically screened locking domains for HIV-1 UFO trimer-presenting E2p and I3-01 nanoparticles. In this study, we systematically screened locking domains for Ebola GPΔMuc-UFOg trimer-presenting E2p and I3-01 nanoparticles. The locking mechanism can be illustrated in a schematic drawing (FIG. 8D, left). To visualize the structure of a 60-meric nanoparticle with locking domains, we constructed an atomic model for the E2p nanoparticle and incorporated a locking domain (LD4) and a T-cell epitope (PADRE) into the model in a step-wise manner (FIG. 8D, right). In our study, seven GPΔMuc-UFOg-E2p-LDn constructs (n=1 to 7) and five GPΔMuc-UFOg-10GS-I3-01-LDn constructs (n=4/5/7/8/9) were transiently expressed in ExpiCHO cells. The GPΔMuc fusion proteins were extracted from the supernatants using either an Mab100 antibody column (for ferritin and E2p) or an Mab114 antibody column (for I3-01) prior to purification on a Superose 6 10/300 column. Among all E2p-based constructs, $LD_4$ and $LD_7$ showed the highest yield and purity, while among all I3-01-based constructs, LD7 and LD8 gave the best results (FIG. 8E). This was largely consistent with our previous findings for HIV-1 UFO gp140 nanoparticles, where LD4 and LD7 appeared to be most compatible with E2p and I3-01, respectively. Therefore, E2p in combination with LD4 and I3-01 with LD7 can be used as two general nanoparticle platforms for vaccine development, irrespective of the immunogens displayed.

Another finding consistent with our previous observation for HIV-1 gp140 nanoparticles was that adding a T-cell epitope to the C-terminus of the locking domain notably improved the yield and purity of the resulting nanoparticles, in this case, the GPΔMuc-UFOg nanoparticles (FIG. 8F). This could be explained by the formation of a hydrophobic T-cell epitope cluster at the center of a hollow nanoparticle (FIG. 8D, right). BN-PAGE further confirmed nanoparticle assembly by showing high-molecular-weight bands on the gel (FIG. 8G). However, all GPΔMuc-I3-01 fusion constructs showed unassembled dimer and monomer species. Finally, the antigenic profiles of three WT GPΔMuc nanoparticles and three GPΔMuc-UFOg nanoparticles were compared to their respective GPΔMuc trimers in ELISA (FIG. 8H). Overall, GPΔMuc nanoparticles showed much stronger binding to neutralizing antibodies than GPΔMuc trimers.

Example 8

Vaccines for Other Viruses Utilizing Class-I Fusion—Arenaviruses

Based on the same design strategy, we developed nanoparticle vaccines for arenaviruses. Arenaviruses are also known to cause severe hemorrhagic fever in humans. Lassa mammarenavirus (LASV) is the etiologic agent of Lassa fever and a major public health burden in West Africa. The LASV glycoprotein complex (GPC) is a trimer of heterodimers, each containing the receptor-binding subunit GP1 and the transmembrane, fusion-mediating subunit GP2. Similar to other class-I fusion proteins such as HIV-1 gp160 and Ebola GP, LASV GPC is responsible for cell entry and presents a main target for neutralizing antibody response. Currently, there is no vaccine available to prevent LASV infection. Recently, a crystal structure of LASV GPC in complex with a human neutralizing antibody was reported (see Hastie et al., 356 (6341):923-928, 2017).

In our study, we designed GPC fusion constructs based on the amino acid sequence of the ectodomain of a LASV strain (GenBank: NP_694870). We packed an antibody column based on the neutralizing antibody 37.7H (see Hastie et al., Science 356(6341):923-928, 2017) for the tag-free purification of LASV GPC and nanoparticles. Two fusion constructs (GPC-10GS-FR and GPC-SGS-E2p-LD4-PADRE) were designed to test the LASV nanoparticle vaccine concept, which would lead to nanoparticles with diameters of 26.3 nm and 37.6 nm, respectively (FIG. 9A). These two fusion constructs were transiently expressed in ExpiCHO cells and purified using a 37.7H antibody column. Since 37.7H binds to GP2 of the LASV GPC trimer at the base, it may not be optimal for purification of GPC nanoparticles due to the restricted access to GP2 on the nanoparticle surface. This explains the low yield observed for both constructs. Nonetheless, the 37.7H-purified proteins were analyzed by negative-stain EM, which showed well-formed nanoparticles mixed with unassembled proteins (FIG. 9B). Due to the long flexible linker between GPC and ferritin nanoparticle, GPC spikes could not be recognized on the ferritin nanoparticle surface (FIG. 9B, left). In contrast, a close-up-view of EM images for GPC-SGS-E2p-LD4-PADRE revealed a layer of GPC trimers on the E2p nanoparticle surface (FIG. 9B, right). Taken together, our study confirmed that LASV GPC can be displayed on 60-meric nanoparticles with locking domains, although a more effective antibody column may further improve the purity of GPC nanoparticles.

Example 9

Vaccines for Other Viruses Utilizing Class-I Fusion Mechanism—RSV

We additionally developed nanoparticle vaccines for respiratory syncytial virus (RSV). Human respiratory syncytial virus (hRSV) infection is a leading cause of bronchiolitis and hospitalization in infants, young children, and elderly. The fusion glycoprotein (F) mediates cell entry and is the major target for vaccine design. F can be recognized by neutralizing antibodies isolated from infected donors. Just like HIV-1 gp160, Ebola GP and Lassa GPC, hRSV F is a class-I transmembrane surface protein that has a signal peptide at the N-terminus (amino acids 1-25) and a membrane anchor near the C-terminus. F is first synthesized as an inactive precursor protein, F0, which assembles into a homotrimer upon the activation by cleavage in the trans-Golgi complex by furin or a furin-like cellular endoprotease. The cleavage leads to two disulfide-linked subunits in the form of NH2-F2-F1-COOH. The N-terminus of F1, as a result of the cleavage, contains the fusion peptide (amino acids 137-154), which is a hydrophobic peptide that inserts directly into the host cell membrane to trigger the fusion. The F1 subunit also contains two areas of heptad repeats (HRs) that associate during fusion and bring the viral and cellular membranes into proximity. Crystal structures of pre-fusion F in complex with neutralizing antibodies have been determined to atomic resolution (see McLellan et al., 340 (6136):1113-1117, 2013).

Figure 10:
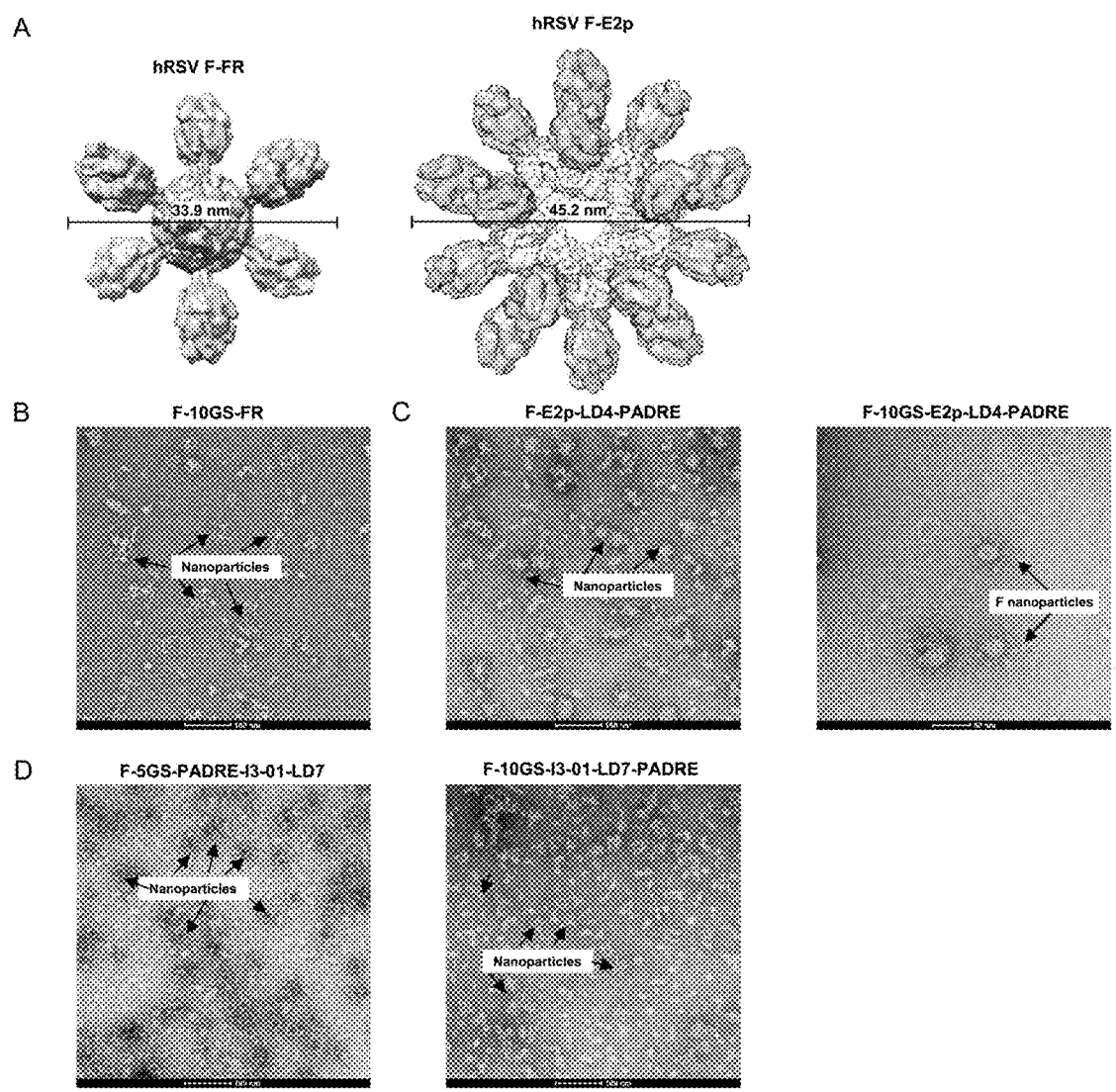
FIG. 10 shows molecular models of human respiratory syncytial virus (hRSV) F trimer-presenting nanoparticles, as well as negative-stain EM images of hRSV F trimers on 24-meric ferritin nanoparticle, on 60-meric E2p nanoparticle with locking domain LD4 and T-cell epitope PADRE, and on 60-meric I3-01 nanoparticle with locking domain LD7 and PADRE. (A): Molecular models showing hRSV F FR nanoparticle and hRSV F E2p nanoparticle. (B): Negative-stain EM analysis of the F-10GS-FR nanoparticle. (C): Negative-stain EM analysis of two F E2p-LD4-PADRE nanoparticles, with and without a 10 aa GS linker between the C-terminus of F and the N-terminus of E2p subunit. (D): Negative-stain EM analysis of two F-I3-01 nanoparticles containing a locking domain (LD7) and PADRE.

In our study, we displayed pre-fusion hRSV F on ferritin, E2p, and I3-01 nanoparticles with various locking domains and linkers tested with E2p and I3-01 60-mers. Molecular modeling indicated that hRSV F FR nanoparticle would have a size of 33.9 nm or larger and hRSV F E2p (or I3-01) would have a diameter of at least 45.2 nm (FIG. 10A). We packed an antibody column for the tag-free purification of hRSV F and F-presenting nanoparticles using a pre-fusion F-specific human neutralizng antibody D25 (see McLellan et al., 340 (6136):1113-1117, 2013). All hSV F fusion constructs were expressed transiently in ExpiCHO cells. The F fusion proteins were extracted from the supernatants using a D25 antibody column and analzyed by negative-stain EM. The F-10GS-FR construct, which contained a 10-amino-acid (G4S)2 linker between the C-terminus of F and the N-terminus of ferritin, formed nanoparticles with visiable "thumb-like" pre-fusion F trimers on the ferritin surface (FIG. 10B), consistent with molecualr modeling (FIG. 10A). Pre-fusion F was then displayed on the E2p nanoaprticle that contains a locking domain (LD4) and a T-cell eptipe (PADRE). Two cosntructs, with and without a 10-amino-acid (G4S)2 linker between the C-terminus of F and the N-terminus of E2p subunit, were tested. Without long linkers, the pre-fusion F trimers appeared as granular protrutions on the E2p nanoparticle surface (FIG. 10C, left), whereas with long linkers an array of "thumb-like" pre-fusion F trimers could be recognized on the E2p nanoparticle surface (FIG. 10C, right). Lastly, Pre-fusion F was displayed on the I3-01 nanoaprticle that contains a locking domain (LD7) and PADRE. Two constructs, with the T-cell epitope (PADRE) inserted between F and E2p (outside) and attached to the C-terminus of LD7 (inside), were created to examine the effect of T-cell epitope location on nanopartilce assembly in the presence of a locking domain. For for the former (F-SGS-PADRE-I3-01-LD7), we observed wellf-formed nanoparticles but could not recognize the pre-fusion F spikes on the nanoparticle surface (FIG. 10D, left). For the latter (F-10GS-I3-01-LD7-PADRE), we observed well-formed nanoparticles decorated with a layer of "thumb-like" pre-fusion F trimers, despite the presence of unassembled F trimers (FIG. 10D, right).

Taken together, our results demonstrated that hRSV F can be displayed on E2p and I3-01 nanoparticles with locking domains, and provided examples for using linkers of different lengths and placing a T-cell epitope in different positions.

Example 10

Vaccines for Other Viruses Utilizing Class-I Fusion Mechanism—CoVs

We also developed nanoparticle vaccines for coronaviruses (CoVs). CoVs are enveloped viruses with a positive-stranded RNA genome. In 2002, an outbreak of severe acute respiratory syndrome (SARS) in Asia led to the discovery of a novel coronavirus that was subsequently named SARS-CoV. During the outbreak, SARS-CoV infected over 8000 people with ~10% fatality rate. In 2012, a new species of coronavirus, Middle East respiratory syndrome coronavirus (MERS-CoV), was identified and has since infected over 2000 people in 27 countries with ~35% fatality rate. For both coronaviruses, the viral genome encodes spike (S), envelope (E), membrane (M), and nucleocapsid (N) structural proteins, among which S protein is responsible for binding to the host receptor via the receptor-binding domain (RBD) in Si subunit, and subsequent membrane fusion and viral entry. RBD contains a core subdomain and a receptor-binding motif (RBM). While the core subdomains are highly similar between the two coronaviruses, their RBMs show different receptor specificities: SARS-CoV recognizes angiotensin-converting enzyme 2 (ACE2), whereas MERS-CoV binds dipeptidyl peptidase 4 (DPP4). For both coronaviruses, the S protein is responsible for infection and thus presents a main target for vaccine design.

Figure 11:
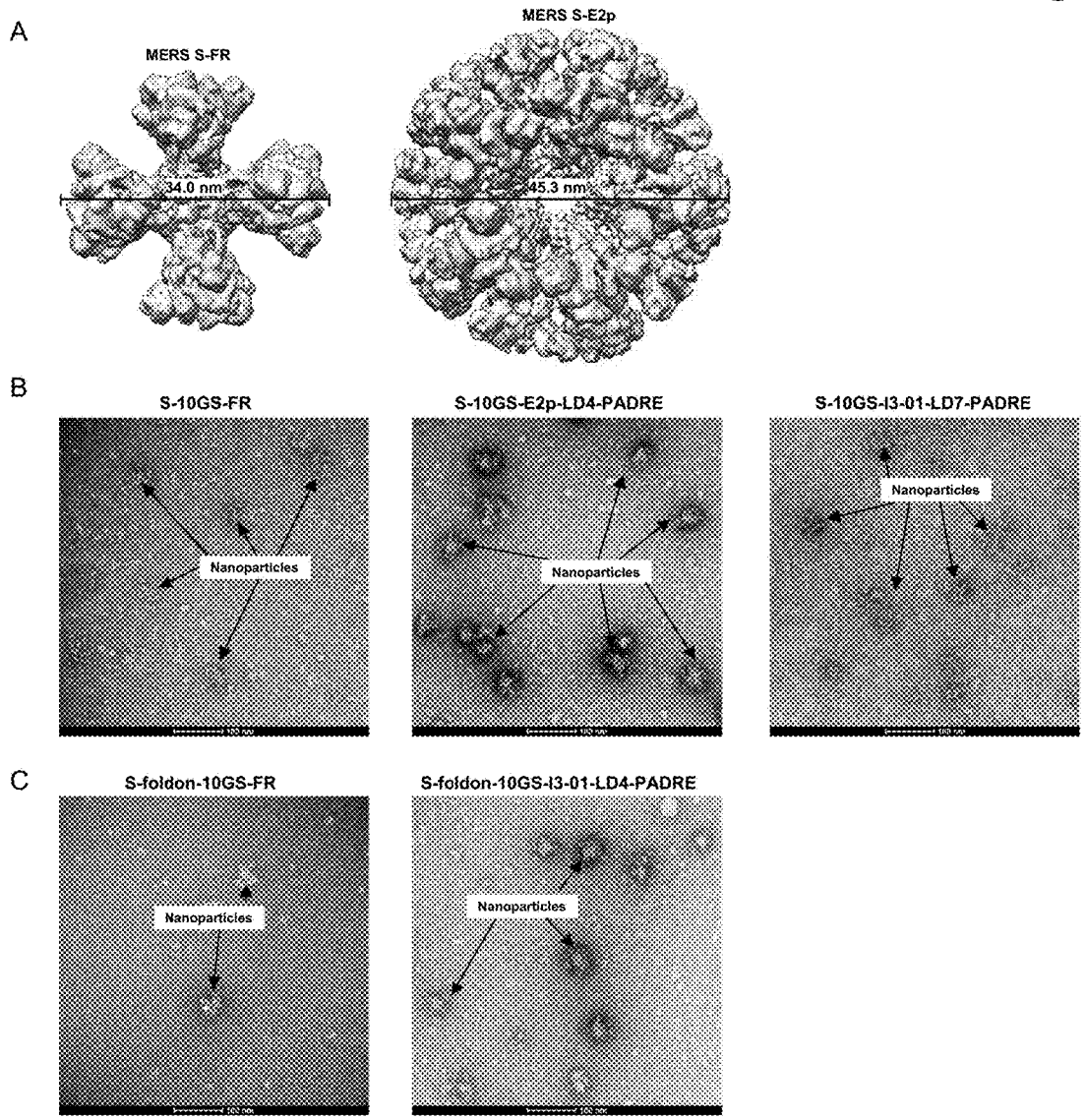
FIG. 11 shows molecular models of MERS coronavirus S trimer-presenting nanoparticles as well as negative-stain EM images of MERS coronavirus S trimeric pikes on 24-meric ferritin nanoparticle, on 60-meric E2p nanoparticle with locking domain LD4 and T-cell epitope PADRE, and on 60-meric I3-01 nanoparticle with locking domain LD7 and PADRE. (A): Molecular models of MERS S FR nanoparticle and MERS S E2p nanoparticle. (B): Negative-stain EM analysis of MERS S fusion proteins, S-10GS-FR, S-10GS-E2p-LD4-PADRE and S-10GS-I3-01-LD7-PADRE. (C): Negative-stain EM analysis of MERS S nanoparticles containing a C-terminal trimerization motif foldon.

In our study, we displayed the MERS-CoV S trimer (see Pallesen et al., PNAS, 114: E7348-E7357 and PDB ID: 5W9K) on ferritin, E2p, and I3-01 nanoparticles, with locking domains incorporated in the E2p and I3-01 constructs. The S construct was derived from a specific MERS-CoV strain (GenBank: JX869059). Molecular modeling indicated that MERS S FR nanoparticle would have a size of 34.0 nm or larger and MERS S E2p (or I3-01) nanoparticle would have a diameter of at least 45.2 nm (FIG. 11A). We developed an antibody column for the tag-gree purification of MERS-CoV S and S nanoparticles using an RBD-directed neutralizng antibody, MCA1. After transient expression in ExpiCHO cells, the S fusion proteins were extracted from the supernatants using a MCA1 antibody column and directly analzyed by negative-stain EM. MERS S-10GS-FR, which contained a 10-aa GS linker (SEQ ID NO:24) between the C-terminus of S and the N-terminus of the ferritin subunit, formed nanoparticles with large S spikes visible on the surface (FIG. 11B, left). MERS S-10GS-E2p-LD4-PADRE (FIG. 11B, middle) and S-10GS-I3-01-LD7-PADRE (FIG. 11B, right) formed larger nanoparticles with twenty S spikes displayed on the surface. However, the EM images also showed unassembled S fusion proteins.

To improve the stability of S protein on nanoparticles, we inserted a "C-terminal trimerization motif of T4 fibritin", or foldon, between S and the nanoparticle subunit. On the nanoparticles formed by S-foldon-10GS-FR (FIG. 11C, left) and S-foldon-10GS-I3-01-LD4-PADRE (FIG. 11C, right), the S spikes could be clearly recognized in EM images, confirming that additional structural components can be incorporated into the nanoparticles with locking domains.

Example 11

Vaccine for Viruses Utilizing Class-II Fusion Mechanism-HCV

We further applied the same vaccine design strategy in the development of HCV E2 core nanoparticle vaccines. Hepatitis C virus (HCV) is a small, enveloped, single-stranded, positive-sense RNA virus of the genus *Hepacivirus* in the family of Flaviviridae. Infecting 1-2% of the world population, HCV is a major health burden that leads to approximately 500,000 deaths annually and an estimated 1.5-2 million new infections each year. HCV has a high genetic diversity and can be classified into seven major genotypes and 86 subtypes. HCV can undergo rapid mutation that gives rise to viral quasispecies within infected individuals to escape the host immune system. However, spontaneous viral clearance in 20-30% of acutely infected patients suggests that HCV infection is preventable with an effective immune response induced by vaccination. The E1 and E2 envelope glycoproteins form a heterodimer on the HCV envelope that mediates viral entry into host hepatocytes. As the receptor binding protein, E2 directly interacts with host cellular receptors CD81 and SR-B1 and is a primary target for neutralizing antibodies which neutralize HCV mainly by blocking CD81 interactions. E2 constructs with truncations at highly variable region 1 (HVR1) and variable regions 2 and 3 (VR2/3), termed E2 cores, were developed to facilitate the structural analysis. Crystal structures of an E2 core derived from isolate H77 (genotype 1a) in complex with broadly neutralizing antibody AR3C (see Kong et al., Science 342(6162):1090-1094, 2013) and of a truncated E2 derived from isolate J6 (genotype 2a) bound to neutralizing antibody 2A12 (Khan et al., Nature, 509(7500):381-384, 2014) provided the first insight into immune recognition of HCV envelope glycoproteins. However, currently there is no licensed vaccine available to prevent HCV infection.

Figure 12:
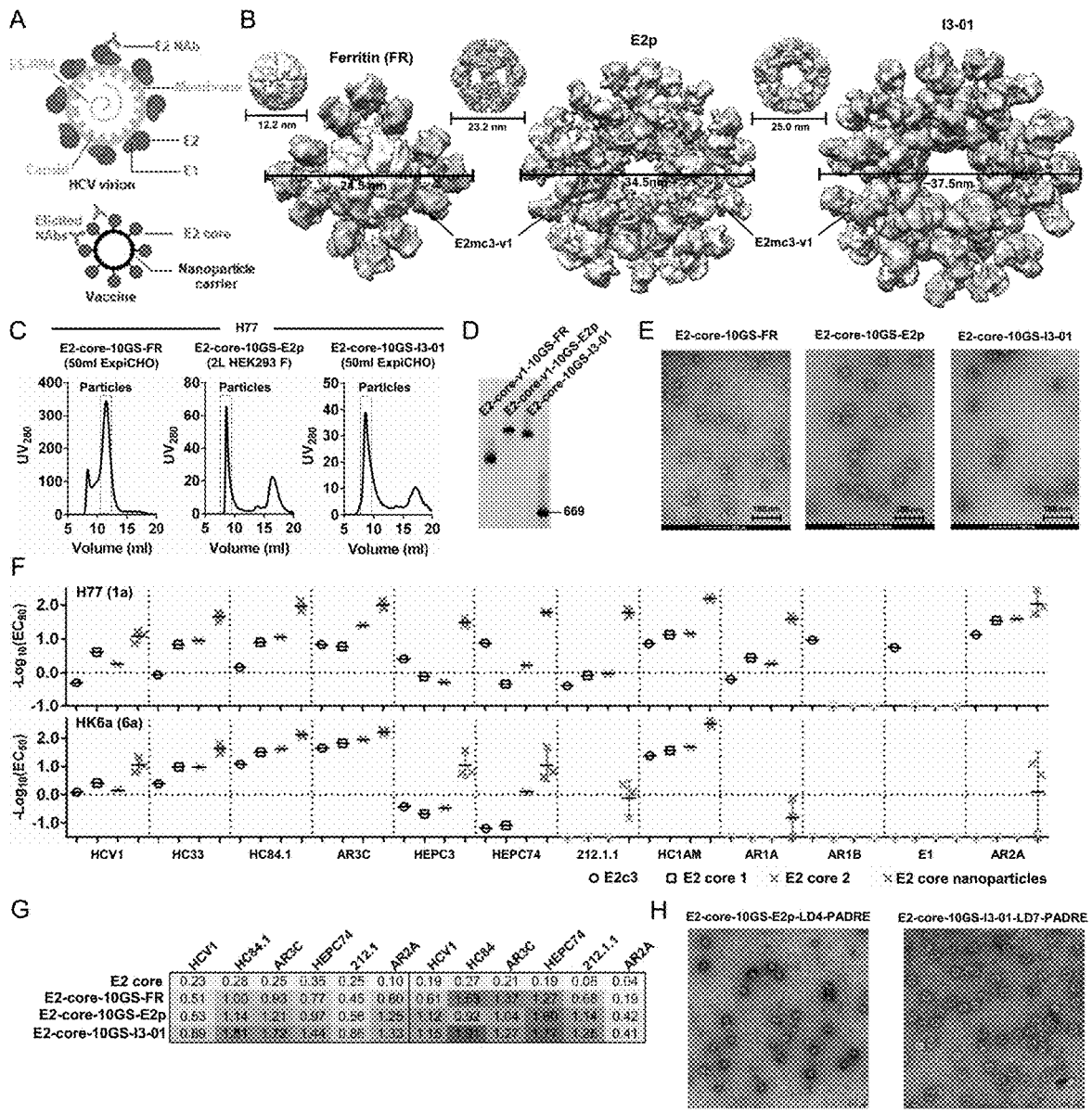
FIG. 12 shows the vaccine concept, molecular models, biochemical and biophysical analyses such as size exclusion chromatography (SEC), blue native polyacrylamide gel electrophoresis (BN-PAGE) and negative-stain EM images, and antigenic characterization such as ELISA binding for hepatitis C virus (HCV) glycoprotein E2 core-presenting nanoparticles with and without locking domains. (A): Illustration of nanoparticles displaying E2 cores on the surface for eliciting neutralizing antibody responses. (B): Molecular models three E2 core nanoparticle platforms. (C): SEC analysis of expressed and purified E2 core fusion proteins. (D) and (E): BN-PAGE and negative-stain EM analysis of SEC-purified E2 core fusion proteins. (F): Binding of E2 core nanoparticles to various broadly neutralizing antibodies as measured by EC5o. (G): Analysis of antibody binding of E2 core nanoparticles against their respective E2 cores using Octet. (H): Negative-stain EM analysis of E2 core nanoparticles containing locking domains.

In our study, we designed E2 core nanoparticles as HCV vaccines. We hypothesized that nanoparticles each displaying 24 to 60 E2 cores on the surface can elicit effective neutralizing antibody responses to the conserved E2 epitopes and therefore present promising HCV vaccine candidates (FIG. 12A). To validate this hypothesis, we tested three nanoparticle platforms, 24-meric ferritin (FR) and 60-meric E2p and I3-01, which would lead to E2 core nanoparticles of 24.5 to 37.5 nm (FIG. 12B). The E2 core constructs used in our study were derived from the amino acid sequences of E2 of two isolates, H77 (genotype 1a) and HK6a (genotype 6a). In our design, the C-terminus of E2 core was genetically fused to the N-terminus of a nanoparticle subunit via a 10-GS linker (SEQ ID NO:24). The E2 core fusion constructs were transiently expressed in ExpiCHO or 293 F cells and purified by an AR3C antibody column followed by SEC using a Superose 6 10/300 GL column (FIG. 12C). For H77 isolate derived construct, the SEC profiles demonstrated high yield and high purity for all E2 core nanoparticles, with different patterns observed for 24- and 60-mers. While E2-core-10GS-FR produced a peak at 8-9 ml corresponding to aggregates, both E2-core-10GS-E2p and I3-01 constructs showed a peak at 15-20 ml tailing the nanoparticle peak (FIG. 12C). For HK6a isolate derived construct, a reduction in particle yield and purity was accompanied by an increase in lower-molecular-weight species. The SEC-purified E2 core fusion protein was analyzed by BN-PAGE and negative-stain EM, which showed high-molecular-weight bands and homogeneous nanoparticles, respectively (FIGS. 12D and 12E). We observed enhanced antibody binding for E2 core nanoparticles, as indicated by an up to 100-fold change in $EC_{50}$ for most broadly neutralizing antibodies (FIG. 12F). To further investigate the effect of multivalent display on antigenicity, we tested H77- and HK6a-derived E2 core nanoparticles against their respective E2 cores using Octet and a small panel of antibodies (FIG. 12G). A correlation between the peak antibody binding signal and the antigen valency was observed for both H77 and HK6a derived nanoparticles: 60-mer>24-mer>monomer.

Lastly, we examined the use of locking domains in E2 core nanoparticles. To this end, we tested constructs E2-core-10GS-E2p-LD4-PADRE and E2-core-10GS-I3-01-LD7-PADRE derived from HCV H77 isolate. Negative-stain EM showed clean, homogenous nanoparticles for both constructs (FIG. 12H). Of note, E2-core-10GS-E2p-LD4-PADRE showed a solid surface in EM images due to the dense inner shell formed by LD4 and PADRE, whereas its counterpart without LD4 and PADRE appeared hollow. Nonetheless, our results confirmed that HCV E2 cores can be displayed on nanoparticles with locking domains.

Example 12

Vaccine for Viruses Utilizing Class-II Fusion Mechanism-ZIKV

We also applied the vaccine design strategy described herein towards the development of Zika virus (ZIKV) DIII nanoparticle vaccines. ZIKV is a positive-strand RNA virus of *Flaviviridae*, which also includes Dengue (DENV), West Nile (WNV), Japanese encephalitis (JEV), and yellow fever (YFV) viruses. The ZIKV genome encodes three structural proteins (capsid, prM, and envelope) and seven non-structural proteins (NS1, NS2a/b, NS3, NS4a/b, and NS5). The ZIKV outbreak in 2015 and 2016 has caused a worldwide public health crisis. Transmitted primarily by *Aedes* species mosquitos, ZIKV can cause Guillain-Barré syndrome (GBS) in adults and microcephaly in newborns. Several envelope (E)-based vaccine candidates have been reported to prevent ZIKV infection in mice and NHPs. However, the antibody-dependent enhancement (ADE) of ZIKV infection and pathogenesis due to preexisting anti-flavivirus immunity raised safety concerns about current vaccine strategies. No other safer and more effective vaccines are available to prevent ZIKV infection.

ZIKV E protein consists of three structural domains, DI, DII, and DIII. Of the three domains, the elongated finger-like DII is responsible for E dimerization and contains a conserved fusion loop (FL) that triggers pH-dependent entry by fusion of viral and host cell membranes. DIII forms a C-terminal immunoglobulin (Ig)-like domain that contributes to viral attachment. Many neutralizing and non-neutralizing antibodies have been identified from ZIKV-infected donors with and without prior exposure to DENV. In general, DIII-directed antibodies tend to be ZIKV-specific and more potently neutralizing than DI/II-directed antibodies. The latter are often cross-reactive with DENV, poorly neutralizing, and in some cases, markedly enhance the viral infection in vivo.

Figure 13:
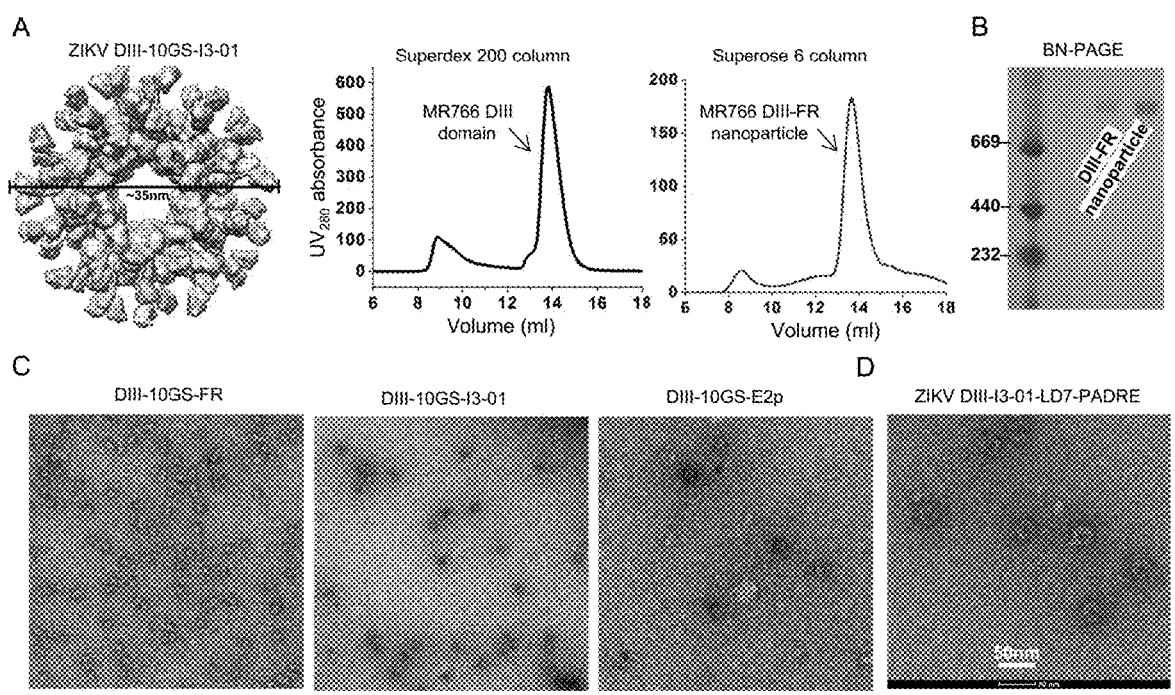
FIG. 13 shows the molecular model of Zika virus (ZIKV) DIII-10GS-I3-01 nanoparticle, followed by biochemical and biophysical characterization such as size exclusion chromatography (SEC), blue native polyacrylamide gel electrophoresis (BN-PAGE) and negative-stain EM analysis for DIII domain displayed on 24-meric ferritin nanoparticle, on 60-meric E2p nanoparticle, and on 60-meric I3-01 nanoparticle with locking domain LD7 and T-cell epitope PADRE. (A): Molecular model and SEC profile of DIII-FR nanoparticles. (B): BN-PAGE analysis of SEC purified fusion proteins. (C): Negative-stain EM analysis of DIII nanoparticles. (D): Negative-stain EM analysis of DIII I3-01 nanoparticle containing a locking domain LD7.

In our study, we designed DIII nanoparticles based on 24-meric ferritin (FR) and 60-meric E2p and I3-01 as potential ZIKV vaccine candidates. The DIII fusion constructs were based on the amino acid sequence of DIII derived from E proteins of African strain MR766 (GenBank: MK105975) and Asian strain BeH818995 (GenBank: KU365777). We also developed an antibody column for the tag-free purification of DIII nanoparticles using a DIII-directed neutralizing antibody ZK2B10 (see Yu et al., JCI Insight 2(12): 93042, 2017). All the DIII-FR fusion constructs were transiently expressed in ExpiCHO cells and purified by a ZK2B10 antibody column. Molecular modeling indicates that the 60-meric I3-01 with a layer of DIIIs on the surface will render a nanoparticle of ~35 nm (FIG. 13A, left). In the SEC profile, we observed a high peak corresponding to well-formed DIII-ferritin nanoparticles (FIG. 13A, right). The SEC fraction eluted at 14 ml on a Superose 6 10/300 GL column was analyzed by BN-PAGE, which showed high-molecular-weight bands characteristic of FR nanoparticles (FIG. 13B). Negative-stain EM showed well-formed DIII nanoparticles (FIG. 13C, left). However, due to the small size of DIII and the use of a flexible 10GS linker, we could not recognize DIII on the nanoparticle surface. Following the same protocol, we produced I3-01 and E2p fusion proteins and assessed their nanoparticle assembly by negative-stain EM (FIG. 13C, middle and right). While DIII-10GS-I3-01 nanoparticles could be readily seen in the EM images, E2p appeared to have difficulties with nanoparticle assembly, resulting in a low yield.

Lastly, we examined whether the locking mechanism can further improve DIII display on the I3-01 nanoparticle. Indeed, negative-stain EM showed homogeneous DIII-10GS-I3-01-LD7-PADRE nanoparticles that were produced in ExpiCHO cells with high yield and high purity (FIG. 13D). In summary, we have successfully displayed ZIKV DIII on various nanoparticle platforms with the optimal properties observed for an I3-01 nanoparticle construct containing locking domain LD7 and T-cell epitope PADRE.

Example 13

Vaccine Development for Non-Viral Targets—Malaria Vaccine

We have further extended our vaccine research to intracellular pathogens such as *Plasmodium falciparum* (malaria) and *Mycobacterium tuberculosis* (TB) and human proteins such as proprotein convertase subtilisin/kexin type 9 (PCSK9). Our main hypothesis is that nanoparticle display will enhance the immune response to intracellular pathogens and break immune tolerance for human proteins. Antibody and T cell responses will be measured as key immunologic readouts.

Malaria vaccine. *Plasmodium (P.) falciparum* is a unicellular protozoan parasite that causes malaria, a life-threatening disease, in humans. *P. falciparum* can be transmitted to people through the bites of infected female *Anopheles* mosquitoes. In 2017, *P. falciparum* infected an estimate of 219 million people in 87 countries, with approximately 435,000 malaria-related deaths. Currently, there is no licensed vaccine to prevent *P. falciparum* infection although malaria can be treated. In our studies, we have developed malaria nanoparticle vaccines based on three antigens important to the life cycle of this parasite: Pfs25, circumsporozoite protein (CSP), and reticulocyte binding protein homolog 5 (PfRHS).

The first antigen, Pfs25, is a 25-kDa sexual stage antigen expressed on the surface of zygote and ookinete forms of the parasite. Anti-Pfs25 antibodies can block the development of *P. falciparum* oocysts in the midgut of the mosquito vector.

Figure 14:
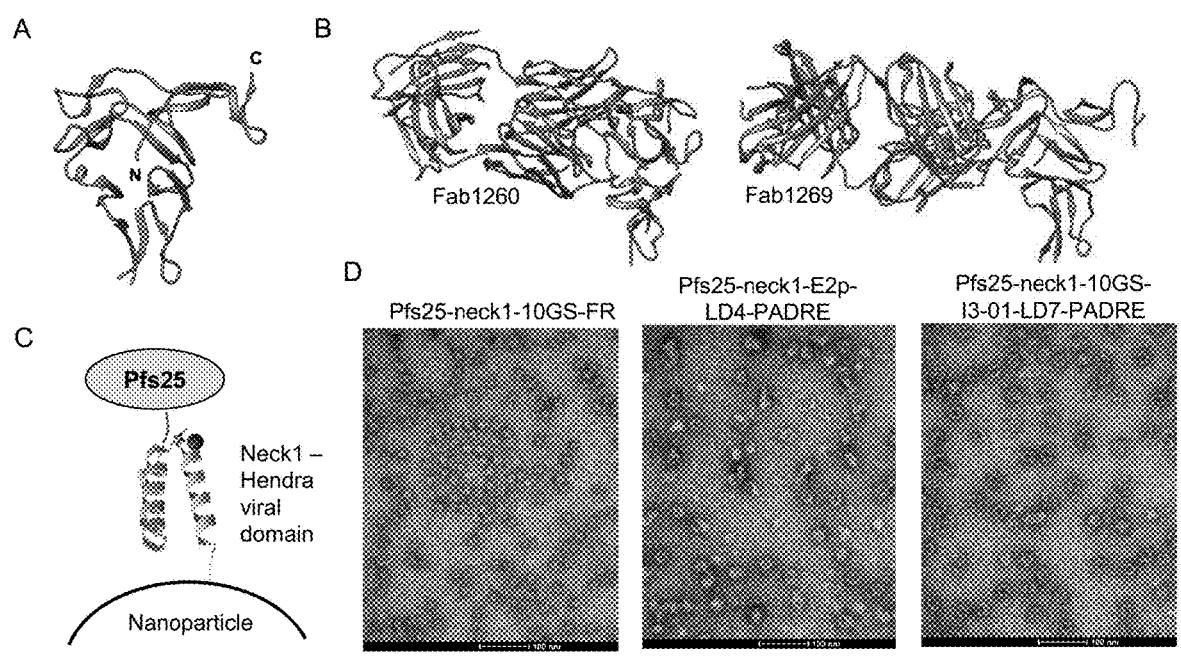
FIG. 14 shows structures of the *P. falciparum* (malaria) antigen Pfs25 and its complex with known neutralizing antibodies, the design concept of Pfs25 nanoparticle with a neck domain, and negative-stain EM images of Pfs25 on 24-meric ferritin nanoparticle, on 60-meric E2p nanoparticle with locking domain LD4 and T-cell epitope PADRE, and on 60-meric I3-01 with locking domain LD7 and PADRE, all with a neck domain inserted between Pfs25 and the nanoparticle. (A): Structures of Pfs25 in complex with monoclonal antibodies. (B): Structures showing binding of two anti-Pfs25 antibodies to Pfs25. (C): Structure showing a "neck" region to Pfs25 nanoparticle. (D): Negative-stain EM analysis showing neck1-containing Pfs25 nanoparticles.

Currently, Pfs25 is the most developed transmission-blocking vaccine (TBV) candidate and has been tested in human clinical trials. Anti-Pfs25 antibodies induced by human vaccination with soluble Pfs25 in adjuvant Montanide ISA 51 are functional in the standard membrane feeding assay (SMFA) and block the development of both laboratory and field isolates of *P. falciparum*. Structures of Pfs25 in complex with monoclonal antibodies isolated from humanized mice have been determined (see Scally et al., Nat Commun, 8:1568, 2017), providing a basis for rational vaccine design (FIG. 14A).

We have tested two anti-Pfs25 antibodies, Fab1260 and Fab1269 (FIG. 14B), for their ability to purify Pfs25 from the cell supernatants. Based on ELISA data, Fab1260 was selected to pack an antibody column for the tag-free purification of Pfs25 nanoparticles. We also designed a "neck" region to facilitate the multivalent display of Pfs25, which has a flat L-shape structure, on nanoparticle surface (FIG. 14C). To be more specific, a three-helix bundle derived from a viral protein was inserted between Pfs25 and the nanoparticle subunit, with or without a linker (FIG. 14C). Two helix bundles derived from the Hendra virus domain (PDB ID: 4HEO) and the Measles virus domain (PDB ID: 1OKS), termed neck1 and neck2, were tested in conjunction with various nanoparticle platforms. All fusion constructs were expressed in ExpiCHO cells followed by purification using an Fab1260 antibody column. The Fab1260-purified fusion proteins were characterized by negative-stain EM, which showed nanoparticles for only the neck1-containing constructs (FIG. 14D). Specifically, Pfs25-neck1-10GS-FR nanoparticles showed the highest yield and purity, as indicated by EM (FIG. 14D, left). The Pfs25-neck1-E2p-LD4-PADRE construct appeared to have generated a mixture of well-formed nanoparticles and aggregates (FIG. 14D, middle). The Pfs25-neck1-10GS-I3-01-LD7-PADRE construct produced nanoparticles with similar high purity to the ferritin construct but slightly lower yield (FIG. 14D, right). This result was consistent with the fact that the N-termini of I3-01 surrounding each 3-fold axis have a large spacing of 5 nm, which is suitable for displaying large proteins of irregular shape, e.g. Pfs25. In summary, Pfs25 can be displayed on 60-meric nanoparticles with locking domains and T-cell epitopes.

Figure 15:
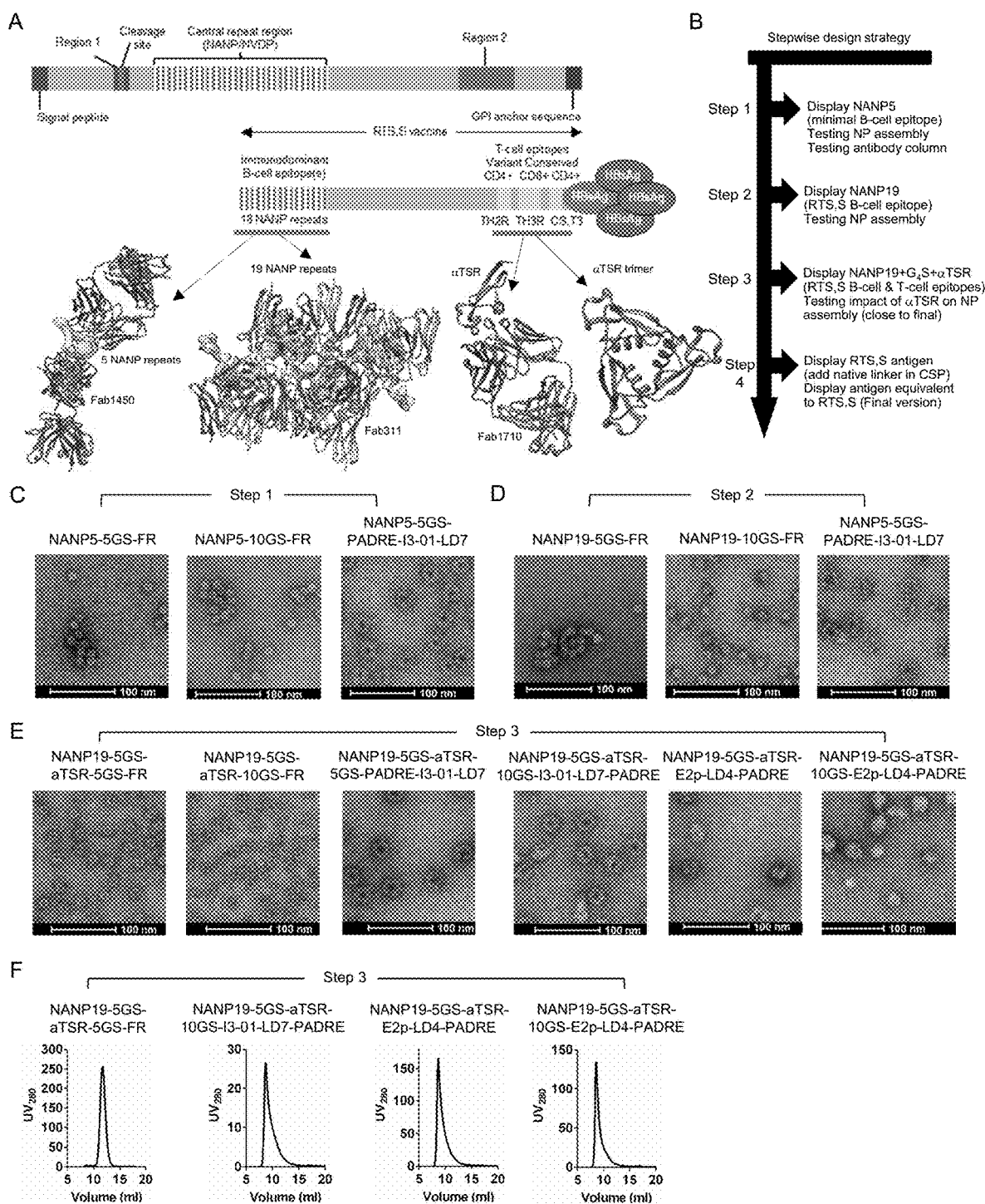
FIG. 15 shows the schematic composition of the *Plasmodium Falciparum* (malaria) antigen circumsporozoite protein (CSP), the schematic composition of GSK RTS,S vaccine, the flowchart of a stepwise strategy to design CSP-based nanoparticle vaccine, negative-stain EM images of various components of antigen CSP on 60-meric ferritin and on 60-meric I3-01 nanoparticle with locking domain LD7 and T-cell epitope PADRE, and size exclusion chromatography (SEC) profiles. (A): Schematic composition of CSP and RTS,S vaccine. (B): Stepwise design of CSP-based nanoparticle vaccine. (C)-(E): Negative-stain EM analysis of CSP nanoparticles with different components. (F): SEC profiles of CSP nanoparticles.

The second antigen, circumsporozoite protein (CSP), is a secreted protein of the sporozoite stage of the plasmodium parasite and is critical for sporozoite function and invasion of hepatocytes. CSP is the antigen used in the RTS,S vaccine (Mosquirix™), which is currently in human clinical trials. As the most clinically advanced vaccine candidate, RTS,S/AS01 (RTS,S) has been shown to provide partial protection against malaria in children. CSP comprises an N-terminal region containing a signal peptide sequence and Region I that binds heparin sulfate proteoglycans and has a conserved proteolytic cleavage site; a central region containing many repeats of a four-amino-acid motif, NANP or NVDP; and a C-terminal region containing Region II [a thrombospondin (TSP)-like domain] and a canonical glycosylphosphatidylinositol (GPI) anchor addition sequence (FIG. 15A, top). The RTS,S vaccine contains 189 amino acids from CSP (amino acids 199-387), including the last 18 NANP repeats and C-terminus exclusive of the GPI anchor addition sequence, attached to a hepatitis B virus surface antigen (HBsAg) (FIG. 15A, bottom).

In our study, we have taken a stepwise strategy to design CSP nanoparticle vaccines with locking domains (FIG. 15B), namely, we displayed the minimal B-cell epitope (step 1), the full-length B-cell epitope (step 2), the full-length B-cell epitope plus the C-terminal T-cell epitope (step 3), and the RTS,S antigen (step 4) of the CSP protein on nanoparticles. To enable the tag-free purification, we packed an antibody column using Fab1450, for which a complex structure with NANP (SEQ ID NO:27) repeats has been determined (FIG. 15A, bottom left). All CSP fusion constructs were transiently expressed in 25 ml ExpiCHO cells followed by Fab1450 purification and negative-stain EM analysis. In step 1, we displayed the minimal B-cell epitope, 5 NANP repeats (NANP5), on two nanoparticles. We observed extremely high yields for all constructs tested. Negative-stain EM showed high-purity NANP5-SGS-FR and NANP5-10GS-FR nanoparticles without any other protein species (FIG. 15C, left and middle). We also expressed the NANP5-SGS-PADRE-I3-01-LD7 construct, which formed homogeneous nanoparticles with high yield and high purity (FIG. 15C, right). Our results thus confirmed the utility of Fab1450 antibody column and the NANP5 nanoparticle assembly with and without locking domains. In step 2, we displayed the full-length B-cell epitope in the RTS,S vaccine antigen, NANP19, on the three nanoparticle platforms for negative-stain EM analysis (FIG. 15D). Despite the significant increase in the number of NANP repeats, all constructs formed homogeneous nanoparticles with high yield and high purity. Our results thus confirmed NANP19 nanoparticle assembly with and without locking domains.

In step 3, we designed and characterized six fusion constructs all containing the full-length B-cell epitope NANP19 and the C-terminal T-cell epitope αTSR domain with a 5GS linker (SEQ ID NO:17) in between. Negative-stain EM confirmed that NANP19-5GS-αTSR can be successfully displayed on all three nanoparticle platforms, with and without locking domains (FIG. 15E). Since NANP19-5GS-αTSR contains all the structurally and functionally defined components in the RTS,S antigen and only differs in the linker, the two antigens should share the same characteristics.

We further assed the yield and purity of these NANP19-5GS-αTSR nanoparticles produced in 25 ml ExpiCHO cells with SEC (FIG. 15F). Consistent with the EM data, NANP19-5GS-αTSR nanoparticles showed high purity, as indicated by a single peak in the SEC profiles. In terms of yield, we observed a nanoparticle-specific pattern: FR>E2p>I3-01. Taken together, we have developed a series of malaria vaccine candidates based on various combinations of structural and antigenic components of CSP, all of which can be displayed on 60-meric nanoparticles with locking domains.

The third antigen, *P. falciparum* reticulocyte binding protein homolog 5 (PfRHS), is a merozoite adhesin required for erythrocyte invasion. PfRHS is the only member demonstrated to be necessary for erythrocyte invasion in all tested strains, through its interaction with the erythrocyte surface protein basigin (also known as CD147 and EMM-PRIN) (see Wong et al., Nature 565:118-121, 2019). The crystal structure of PfRHS has been determined (see Wright et al., Nature 515:427-430, 2014). We have developed antibody columns for the tag-free purification of PfRHS and PfRHS nanoparticles based on antibodies 9AD4 and QA1. We have designed fusion constructs to display PfRHS on nanoparticles with and without locking domains.

Example 14

Vaccine Development for Non-Viral Targets—Tuberculosis Vaccine

Tuberculosis (TB) is a potentially serious infectious disease caused by *Mycobacterium tuberculosis* bacteria, which mainly infect the lungs. Infecting 25% of the world's population, TB caused up to 10 million disease cases in 2017, resulting in 1.3 million deaths. Although the Bacille Calmette-Guérin (BCG) vaccine has been widely used in countries where TB is common, it does not confer complete protection against TB. A number of novel TB vaccine candidates have been developed against *M. tuberculosis* that are currently in human clinical trials (see Khoshnood et al. *Int. J. Biol. Macromol.* 120:180-188, 2018).

In our study, we displayed two TB antigens on nanoparticles. The first antigen, Ag85 complex, maintains the integrity of the cell wall by catalyzing the transfer of mycolic acids to the cell wall arabinogalactan and through the synthesis of trehalose dimycolate (cord factor). Ag85 is highly immunogenic and can induce potent T-cell and antibody responses. A recent vaccine trial reported rising antibody titers to Ag85A in infants after BCG vaccination, and more importantly, Ag85A-specific IgG was associated with decreased risk of TB. We have expressed Ag85A, B, and C individually in HEK293 F cells and observed well-folded monomers for Ag85A and B, but trimeric proteins for Ag85C. We have designed fusion constructs to display Ag85A, B, and C on nanoparticles with and without locking domains. Since antibodies against Ag85 have not been reported, we utilized the phage display technology to identify Ag85-binding antibodies for the tag-free purification of Ag85A, B, and C nanoparticles.

The second antigen, Mtb72, is a fusion protein composed of Mtb32 and

Mtb39. Mtb72 has been used in combination with the GSK adjuvant ASO1 and demonstrated an efficacy of 54.0% in a clinical trial (see Meeren et al., N. Engl. J. Med., 379:1621-1634, 2018). We have expressed Mtb32 and Mtb39 as separate antigens in HEK293 F cells and observed relatively low yield. We have designed fusion constructs with Mtb32 and Mtb39 displayed on nanoparticles with and without locking domains. We have performed phage library screening to select antibodies for packing antibody columns. Since these TB antigens are either monomers (Ag85A, Ag85B, and Mtb32), similar to HCV E2 and ZIKV DIII, or trimers (Ag85C and Mtb39), similar to HIV-1 Env and Ebola GP, the resulting TB nanoparticles showed broadly similar properties.

Example 15

Vaccine Development for Non-Viral Targets—PCSK9 Vaccine

Figure 16:
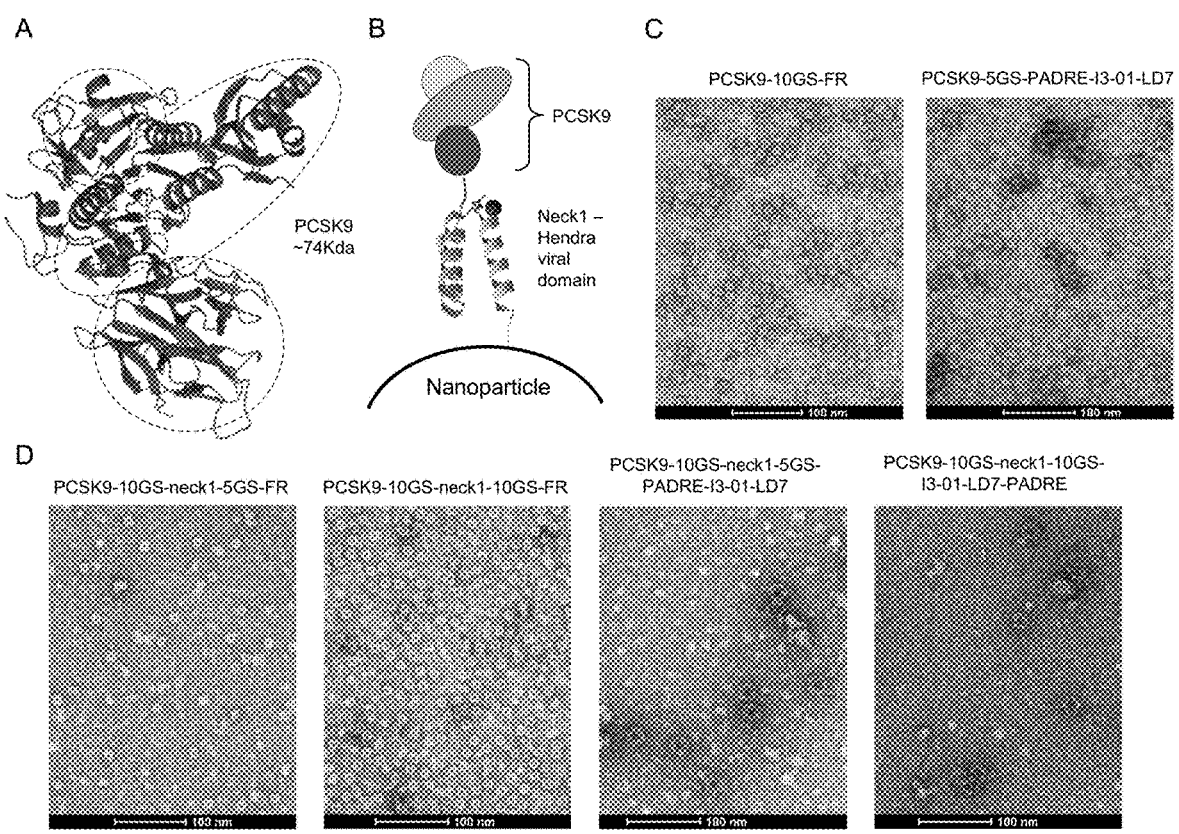
FIG. 16 shows the structure of proprotein convertase subtilisin/kexin type 9 (PCSK9), design concept of PCSK9 nanoparticle with a neck domain, and negative-stain EM images of PCSK9 on 24-meric ferritin nanoparticle and on 60-meric I3-01 nanoparticle with locking domain LD7 and T-cell epitope PADRE, all with a neck domain inserted between PCSK9 and nanoparticle. (A): Structure of PCSK9. (B): Design of PCSK9 nanoparticle containing a neck domain. (C): Negative-stain EM analysis of PCSK9 nanoparticles without a neck domain. (D): Negative-stain EM analysis of PCSK9 nanoparticles containing a neck domain.

Two types lipoproteins carry cholesterol to and from cells, the low-density lipoprotein (or LDL) and the high-density lipoprotein (or HDL). Because LDL contributes to the fatty buildups in arteries, LDL cholesterol is considered "bad" cholesterol. Elevated levels of LDL cholesterol in blood have been associated with an increased risk of cardiovascular disease, a common cause of premature death in the Western countries. Proprotein convertase subtilisin kexin type 9 (PCSK9) regulates serum LDL cholesterol (LDL-C) by controlling the degradation of LDL receptor (LDL-R). PCSK9 is a 74 kDa serine protease that contains three domains: An N-terminal prodomain, a subtilisin-like catalytic domain, and a C-terminal cysteine/histidine-rich domain (CTD) (FIG. 16A). PCSK9 undergoes autocatalytic cleavage, but the 14 kDa prodomain remains noncovalently attached to the catalytic domain and renders the protease inactive. Loss-of-function PCSK9 mutations have been found to be associated with lower concentrations of LDL cholesterol and reduced risk of heart disease. Since these loss-of-function mutations do not cause deleterious side effects, PCSK9 inhibition by vaccine-induced antibodies presents an attractive therapeutic strategy for lowering LDL cholesterol concentration. Crystal structures of full-length and truncated PCSK9 in complex with various ligands have been solved, providing a rational basis for vaccine design (FIG. 16A).

In our study, we have displayed PCSK9 on all three nanoparticle platforms with or without locking domains. Due to the large size and irregular shape of PCSK9, we adopted the "neck" design similar to that used in the Pfs25 nanoparticles (FIG. 16B). Briefly, a three-helix bundle of viral origin (Hendra viral domain) was inserted in the construct between PCSK9 and the nanoparticle subunit. We have packed an antibody column using J16, a potent anti-PCSK9 antibody developed by Pfizer (see Liang et al., J Pharm Exp Ther, 340(2):228-236, 2012), for the tag-free purification of PCSK9 and PCSK9 nanoparticles. After transient expression in ExpiCHO cells, the fusion proteins were extracted from the supernatants by a J16 antibody column and analyzed by negative-stain EM. We first tested two fusion constructs without the neck design (FIG. 16C). While PCSK9-10GS-FR formed homogeneous nanoparticles (FIG. 16C, left), PCSK9-5GS-PADRE-I3-01-LD7 failed to assemble likely due to the large size and irregular shape of PCSK9 (FIG. 16C, right). We then expressed the nanoparticle constructs containing neck1 (FIG. 16D). While both ferritin constructs formed nanoparticles, the one with longer linker between neck1 and ferritin, PCSK9-10GS-neck1-10GS-FR, produced nanoparticles with greater yield and purity (FIG. 16D, panels 1 and 2). The two I3-01 constructs, with PADRE displayed outside and fused to the C-terminus of a locking domain (LD7), formed nanoparticles of slightly different morphologies although unassembled fusion proteins were observed both EM images (FIG. 16D, panels 3 and 4).

In summary, PCSK9 can be displayed on 24-meric ferritin as well as 60-meric I3-01 with the neck domain, the locking domain, and the T-cell epitope PADRE, offering more effective vaccine candidates than PCSK9 as nanoparticle is capable of breaking self-tolerance and inducing higher titers of antibody response.

The invention thus has been disclosed broadly and illustrated in reference to representative embodiments described above. It is understood that various modifications can be made to the present invention without departing from the spirit and scope thereof.

It is further noted that all publications, sequence accession numbers, patents and patent applications cited herein are hereby expressly incorporated by reference in their entirety and for all purposes as if each is individually so denoted. Definitions that are contained in text incorporated by reference are excluded to the extent that they contradict definitions in this disclosure.

What is claimed is:

1. A vaccine composition, comprising a polypeptide immunogen that is displayed on the surface of a self-assembling nanoparticle, wherein a locking domain is embedded inside the self-assembling nanoparticle and is linked to a subunit of the self-assembling nanoparticle, and wherein the locking domain comprises the amino acid sequence selected from SEQ ID NOs:1-9, or a conservatively modified variant thereof.

2. The vaccine composition of claim 1, wherein the locking domain is covalently linked to a subunit of the self-assembling nanoparticle.

3. The vaccine composition of claim 2, wherein N-terminus of the locking domain is fused to C-terminus of the self-assembling nanoparticle subunit via a linker sequence.

4. The vaccine composition of claim 1, further comprising a pan-reactive T-cell epitope.

5. The vaccine composition of claim 4, wherein N-terminus of the pan-reactive T-cell epitope is fused to the C-terminus of the locking domain.

6. The vaccine composition of claim 1, further comprising a neck region inserted between the immunogen and the self-assembling nanoparticle subunit, wherein the neck region comprises a 3-helix protein domain that elevates the immunogen further away from the surface of the self-assembling nanoparticle.

7. The vaccine composition of claim 1, further comprising a protein domain inserted between the immunogen and the self-assembling nanoparticle subunit, wherein the protein domain stabilizes the immunogen polypeptide.

8. The vaccine composition of claim 1, wherein the self-assembling nanoparticle is a ball-shaped nanoparticle with rotational symmetry.

9. The vaccine composition of claim 8, wherein the rotational symmetry has 3-fold axis and/or 5-fold axis.

10. The vaccine composition of claim 9, wherein the nanoparticle is of an icosahedral structure.

11. The vaccine composition of claim 1, wherein the polypeptide immunogen is a viral immunogen.

12. The vaccine composition of claim 11, wherein the polypeptide immunogen is a viral immunogen from a virus utilizing class-I fusion mechanism.

13. The vaccine composition of claim 12, wherein the virus is selected from the group consisting of HIV-1 virus, Ebola virus, Marburg virus, Arenaviruses, *respiratory syncytial viruses*(RSV), and coronaviruses.

14. The vaccine composition of claim 11, wherein the polypeptide immunogen is a viral immunogen from a virus utilizing class-II fusion mechanism.

15. The vaccine composition of claim 14, wherein the virus utilizing class-II fusion mechanism is HCV or Zika virus.

16. The vaccine composition of claim 11, wherein the polypeptide immunogen is a non-viral immunogen.

17. The vaccine composition of claim 16, wherein the polypeptide immunogen is an antigen from *Plasmodium falciparum*, an antigen from *Mycobacterium tuberculosis* (TB), or human protein proprotein convertase subtilisin/kexin type 9 (PCSK9).

18. The vaccine composition of claim 1, wherein the polypeptide immunogen is an HIV-1 Env trimer protein.

19. The vaccine composition of claim 18, wherein N-terminus of the locking domain is fused to C-terminus of the nanoparticle subunit via a linker sequence that comprises one or more tandem copies of GGGGS (SEQ ID NO:17).

20. The vaccine composition of claim 18, further comprising a pan-reactive T-cell epitope.

21. The vaccine composition of claim 20, wherein N-terminus of the pan-reactive T-cell epitope is fused to the C-terminus of the locking domain.

22. The vaccine composition of claim 20, wherein the pan-reactive T-cell epitope comprises the sequence AKFVAAWTLKAAA (SEQ ID NO:18).

23. The vaccine composition of claim 18, wherein C-terminus of subunit of the HIV-1 trimer protein is covalently linked to N-terminus of subunit of the self-assembling nanoparticle.

24. The vaccine composition of claim 18, wherein the HIV-1 trimer protein subunit is fused to the self-assembling nanoparticle subunit via a linker sequence.

25. The vaccine composition of claim 24, wherein the linker sequence comprises the sequence (GaSb)n, wherein a is an integer of 1 to 5, b is an integer of 1 to 2, and n is an integer of 1 to 5.

26. The vaccine composition of claim 18, wherein the self-assembling nanoparticle comprises a trimeric sequence.

27. The vaccine composition of claim 18, wherein the subunit of the self-assembling nanoparticle comprises the polypeptide selected from SEQ ID NO:21, SEQ ID NO:22, SEQ ID NO:25 or SEQ ID NO:26, or a conservatively modified variant thereof.

28. The vaccine composition of claim 18, wherein the HIV-1 Env trimer protein is a gp140 trimer.

29. The vaccine composition of claim 18, wherein the HIV-1 Env trimer protein is an uncleaved prefusion-optimized (UFO) gp140 trimer.

30. The vaccine composition of claim 29, wherein the UFO gp140 trimer is a chimeric trimer comprising a modified gp41EcTo domain from HIV-1 strain BG505.

31. The vaccine composition of claim 29, wherein subunit of the UFO gp140 trimer comprises the sequence SEQ ID NO:23, or a conservatively modified variant thereof.

32. The vaccine composition of claim 29, having a subunit sequence that comprises from the N-terminus to the C-terminus: HIV-1 uncleaved prefusion-optimized (UFO) gp140 trimer subunit comprising SEQ ID NO:23, self-assembling nanoparticle subunit comprising SEQ ID NO:21 (E2p), the locking domain comprising SEQ ID NO:1 (LD4), and T-cell epitope AKFVAAWTLKAAA (SEQ ID NO:18).

33. The vaccine composition of claim 32, further comprising a first linker sequence (GGGGS)2 (SEQ ID NO:24) between the HIV-1 uncleaved prefusion-optimized (UFO) gp140 trimer subunit and the self-assembling nanoparticle subunit, and/or a second linker sequence GGGGS (SEQ ID NO:17) between the self-assembling nanoparticle subunit and the locking domain.

34. The vaccine composition of claim 29, having a subunit sequence that comprises from the N-terminus to the C-terminus: HIV-1 uncleaved prefusion-optimized (UFO) gp140 trimer comprising SEQ ID NO:23, self-assembling nanoparticle subunit comprising SEQ ID NO:22 or 25 (13-01), the locking domain comprising SEQ ID NO:2 (LD7), and T-cell epitope AKFVAAWTLKAAA (SEQ ID NO:18).

35. The vaccine composition of claim 34, further comprising a first linker sequence (GGGGS)2 (SEQ ID NO:24) between the HIV-1 uncleaved prefusion-optimized (UFO) gp140 trimer subunit and the self-assembling nanoparticle subunit, and/or a second linker sequence GGGGS (SEQ ID NO:17) between the self-assembling nanoparticle subunit and the locking domain.

36. A pharmaceutical composition, comprising the vaccine composition of claim 1, and a pharmaceutically acceptable carrier.

\* \* \* \* \*

```
                          SEQUENCE LISTING

<160> NUMBER OF SEQ ID NOS: 27

<210> SEQ ID NO 1
<211> LENGTH: 58
<212> TYPE: PRT
<213> ORGANISM: Artificial sequence
<220> FEATURE:
<223> OTHER INFORMATION: Synthetic sequence

<400> SEQUENCE: 1

Phe Ser Glu Glu Gln Lys Lys Ala Leu Asp Leu Ala Phe Tyr Phe Asp
1               5                   10                  15

Arg Arg Leu Thr Pro Glu Trp Arg Arg Tyr Leu Ser Gln Arg Leu Gly
            20                  25                  30

Leu Asn Glu Glu Gln Ile Glu Arg Trp Phe Arg Arg Lys Glu Gln Gln
        35                  40                  45

Ile Gly Trp Ser His Pro Gln Phe Glu Lys
    50                  55

<210> SEQ ID NO 2
<211> LENGTH: 46
<212> TYPE: PRT
<213> ORGANISM: Artificial sequence
<220> FEATURE:
<223> OTHER INFORMATION: Synthetic sequence

<400> SEQUENCE: 2

Ser Pro Ala Val Asp Ile Gly Asp Arg Leu Asp Glu Leu Glu Lys Ala
1               5                   10                  15

Leu Glu Ala Leu Ser Ala Glu Asp Gly His Asp Asp Val Gly Gln Arg
            20                  25                  30

Leu Glu Ser Leu Leu Arg Arg Trp Asn Ser Arg Arg Ala Asp
        35                  40                  45

<210> SEQ ID NO 3
<211> LENGTH: 40
<212> TYPE: PRT
<213> ORGANISM: Artificial sequence
<220> FEATURE:
<223> OTHER INFORMATION: Synthetic sequence

<400> SEQUENCE: 3
```

```
Ser Glu Ala Leu Lys Ile Leu Asn Asn Ile Arg Thr Leu Arg Ala Gln
1               5                   10                  15

Ala Arg Glu Cys Thr Leu Glu Thr Leu Glu Glu Met Leu Glu Lys Leu
            20                  25                  30

Glu Val Val Val Asn Glu Arg Arg
        35                  40

<210> SEQ ID NO 4
<211> LENGTH: 44
<212> TYPE: PRT
<213> ORGANISM: Artificial sequence
<220> FEATURE:
<223> OTHER INFORMATION: Synthetic sequence

<400> SEQUENCE: 4

Met Asn Asp Cys Tyr Ser Lys Leu Lys Glu Leu Val Pro Ser Ile Pro
1               5                   10                  15

Gln Asn Lys Lys Val Ser Lys Met Glu Ile Leu Gln His Val Ile Asp
            20                  25                  30

Tyr Ile Leu Asp Leu Gln Ile Ala Leu Asp Ser His
        35                  40

<210> SEQ ID NO 5
<211> LENGTH: 50
<212> TYPE: PRT
<213> ORGANISM: Artificial sequence
<220> FEATURE:
<223> OTHER INFORMATION: Synthetic sequence

<400> SEQUENCE: 5

Leu Leu Tyr Cys Ser Phe Cys Gly Lys Ser Gln His Glu Val Arg Lys
1               5                   10                  15

Leu Ile Ala Gly Pro Ser Val Tyr Ile Cys Asp Glu Cys Val Asp Leu
            20                  25                  30

Cys Asn Asp Ile Ile Arg Glu Glu Ile Lys Glu Val Ala Pro His Arg
        35                  40                  45

Glu Arg
    50

<210> SEQ ID NO 6
<211> LENGTH: 78
<212> TYPE: PRT
<213> ORGANISM: Artificial sequence
<220> FEATURE:
<223> OTHER INFORMATION: Synthetic sequence

<400> SEQUENCE: 6

Asp Gln Pro Ser Val Gly Asp Ala Phe Asp Lys Tyr Asn Glu Ala Val
1               5                   10                  15

Arg Val Phe Thr Gln Leu Ser Ser Ala Ala Asn Cys Asp Trp Ala Ala
            20                  25                  30

Cys Leu Ser Ser Leu Ser Ala Ser Ala Ala Cys Ile Ala Ala Val
        35                  40                  45

Gly Glu Leu Gly Leu Asp Val Pro Leu Asp Leu Ala Cys Ala Ala Thr
    50                  55                  60

Ala Thr Ser Ser Ala Thr Glu Ala Cys Lys Gly Cys Leu Trp
65                  70                  75

<210> SEQ ID NO 7
<211> LENGTH: 88
```

```
<212> TYPE: PRT
<213> ORGANISM: Artificial sequence
<220> FEATURE:
<223> OTHER INFORMATION: Synthetic sequence

<400> SEQUENCE: 7

Lys Asn Ile Asp Thr Val Arg Glu Ile Ile Thr Val Ala Ser Ile Leu
1               5                   10                  15

Ile Lys Phe Ser Arg Glu Asp Ile Val Glu Asn Arg Ala Asn Phe Ile
            20                  25                  30

Ala Phe Leu Asn Glu Ile Gly Val Thr His Glu Gly Arg Lys Leu Asn
        35                  40                  45

Gln Asn Ser Phe Arg Lys Ile Val Ser Glu Leu Thr Gln Glu Asp Lys
    50                  55                  60

Lys Thr Leu Ile Asp Glu Phe Asn Glu Gly Phe Glu Gly Val Tyr Arg
65                  70                  75                  80

Tyr Leu Glu Met Tyr Thr Asn Lys
                85

<210> SEQ ID NO 8
<211> LENGTH: 39
<212> TYPE: PRT
<213> ORGANISM: Artificial sequence
<220> FEATURE:
<223> OTHER INFORMATION: Synthetic sequence

<400> SEQUENCE: 8

Pro Pro Gly Leu Thr Glu Leu Leu Gln Gly Tyr Thr Val Glu Val Leu
1               5                   10                  15

Arg Gln Gln Pro Pro Asp Leu Val Asp Phe Ala Val Glu Tyr Phe Thr
            20                  25                  30

Arg Leu Arg Glu Ala Arg Arg
        35

<210> SEQ ID NO 9
<211> LENGTH: 65
<212> TYPE: PRT
<213> ORGANISM: Artificial sequence
<220> FEATURE:
<223> OTHER INFORMATION: Synthetic sequence

<400> SEQUENCE: 9

Tyr Ser Asp Glu Gln Val Glu Gln Leu Leu Ala Glu Leu Leu Asn Val
1               5                   10                  15

Leu Glu Lys His Lys Ala Pro Thr Asp Leu Ser Leu Met Val Leu Gly
            20                  25                  30

Asn Met Val Thr Asn Leu Ile Asn Thr Ala Ile Ala Pro Ala Gln Arg
        35                  40                  45

Gln Ala Ile Ala Asn Ser Phe Ala Arg Ala Leu Gln Ser Ser Ile Asn
    50                  55                  60

Glu
65

<210> SEQ ID NO 10
<211> LENGTH: 46
<212> TYPE: PRT
<213> ORGANISM: Artificial sequence
<220> FEATURE:
<223> OTHER INFORMATION: Synthetic sequence

<400> SEQUENCE: 10
```

His Met Gly His Ile Gln Ile Pro Pro Gly Leu Thr Glu Leu Leu Gln
1               5                   10                  15

Gly Tyr Thr Val Glu Val Leu Arg Gln Gln Pro Pro Asp Leu Val Asp
                20                  25                  30

Phe Ala Val Glu Tyr Phe Thr Arg Leu Arg Glu Ala Arg Arg
            35                  40                  45

<210> SEQ ID NO 11
<211> LENGTH: 60
<212> TYPE: PRT
<213> ORGANISM: Artificial sequence
<220> FEATURE:
<223> OTHER INFORMATION: Synthetic sequence

<400> SEQUENCE: 11

Ala Ser Asp Asp Glu Leu Phe Ser Met Leu Asp Gln Arg Phe Gly Gly
1               5                   10                  15

Gly Glu Asp Leu Leu Met Ser Gly Asp Asn Gly Met Thr Glu Glu Lys
                20                  25                  30

Leu Arg Arg Tyr Leu Lys Arg Thr Val Thr Glu Leu Asp Ser Val Thr
            35                  40                  45

Ala Arg Leu Arg Glu Val Glu His Arg Ala Gly Glu
        50                  55                  60

<210> SEQ ID NO 12
<211> LENGTH: 87
<212> TYPE: PRT
<213> ORGANISM: Artificial sequence
<220> FEATURE:
<223> OTHER INFORMATION: Synthetic sequence

<400> SEQUENCE: 12

Met Ala Asp Lys Arg Ala His His Asn Ala Leu Glu Arg Lys Arg Arg
1               5                   10                  15

Asp His Ile Lys Asp Ser Phe His Ser Leu Arg Asp Ser Val Pro Ser
                20                  25                  30

Leu Gln Gly Glu Lys Ala Ser Arg Ala Gln Ile Leu Asp Lys Ala Thr
            35                  40                  45

Glu Tyr Ile Gln Tyr Met Arg Arg Lys Val His Thr Leu Gln Gln Asp
        50                  55                  60

Ile Asp Asp Leu Lys Arg Gln Asn Ala Leu Leu Glu Gln Gln Val Arg
65                  70                  75                  80

Ala Leu Glu Gly Ser Gly Cys
                85

<210> SEQ ID NO 13
<211> LENGTH: 90
<212> TYPE: PRT
<213> ORGANISM: Artificial sequence
<220> FEATURE:
<223> OTHER INFORMATION: Synthetic sequence

<400> SEQUENCE: 13

Met Asn Lys Asn Ile Asp Thr Val Arg Glu Ile Ile Thr Val Ala Ser
1               5                   10                  15

Ile Leu Ile Lys Phe Ser Arg Glu Asp Ile Val Glu Asn Arg Ala Asn
                20                  25                  30

Phe Ile Ala Phe Leu Asn Glu Ile Gly Val Thr His Glu Gly Arg Lys
            35                  40                  45

Leu Asn Gln Asn Ser Phe Arg Lys Ile Val Ser Glu Leu Thr Gln Glu

```
                    50                  55                  60

Asp Lys Lys Thr Leu Ile Asp Glu Phe Asn Glu Gly Phe Glu Gly Val
 65                  70                  75                  80

Tyr Arg Tyr Leu Glu Met Tyr Thr Asn Lys
                 85                  90

<210> SEQ ID NO 14
<211> LENGTH: 66
<212> TYPE: PRT
<213> ORGANISM: Artificial sequence
<220> FEATURE:
<223> OTHER INFORMATION: Synthetic sequence

<400> SEQUENCE: 14

Met Val Glu Asn Pro Met Val Ile Asn Asn Trp His Asp Lys Leu Thr
  1               5                  10                  15

Glu Thr Asp Val Gln Ile Asp Phe Tyr Gly Asp Glu Val Thr Pro Val
                 20                  25                  30

Asp Asp Tyr Val Ile Asp Gly Gly Glu Ile Ile Leu Arg Glu Asn Leu
             35                  40                  45

Glu Arg Tyr Leu Arg Glu Gln Leu Gly Phe Glu Phe Lys Asn Ala Gln
         50                  55                  60

Leu Glu
 65

<210> SEQ ID NO 15
<211> LENGTH: 77
<212> TYPE: PRT
<213> ORGANISM: Artificial sequence
<220> FEATURE:
<223> OTHER INFORMATION: Synthetic sequence

<400> SEQUENCE: 15

Met Pro Ile Thr Ser Lys Tyr Thr Asp Glu Gln Val Glu Lys Ile Leu
  1               5                  10                  15

Ala Glu Val Ala Leu Val Leu Glu Lys His Ala Ala Ser Pro Glu Leu
                 20                  25                  30

Thr Leu Met Ile Ala Gly Asn Ile Ala Thr Asn Val Leu Asn Gln Arg
             35                  40                  45

Val Ala Ala Ser Gln Arg Lys Leu Ile Ala Lys Phe Ala Gln Ala
         50                  55                  60

Leu Met Ser Ser Leu Glu Thr Pro Lys Thr His Leu Glu
 65                  70                  75

<210> SEQ ID NO 16
<211> LENGTH: 70
<212> TYPE: PRT
<213> ORGANISM: Artificial sequence
<220> FEATURE:
<223> OTHER INFORMATION: Synthetic sequence

<400> SEQUENCE: 16

Gly Met Lys Pro Val Ser Leu Ser Tyr Arg Cys Pro Cys Arg Phe Phe
  1               5                  10                  15

Glu Ser His Val Ala Arg Ala Asn Val Lys His Leu Lys Ile Leu Asn
                 20                  25                  30

Thr Pro Asn Cys Ala Cys Gln Ile Val Ala Arg Leu Lys Asn Asn Asn
             35                  40                  45

Arg Gln Val Cys Ile Asp Pro Lys Leu Lys Trp Ile Gln Glu Tyr Leu
         50                  55                  60
```

Glu Lys Cys Leu Asn Lys
65                  70

<210> SEQ ID NO 17
<211> LENGTH: 5
<212> TYPE: PRT
<213> ORGANISM: Artificial sequence
<220> FEATURE:
<223> OTHER INFORMATION: Synthetic sequence

<400> SEQUENCE: 17

Gly Gly Gly Gly Ser
1               5

<210> SEQ ID NO 18
<211> LENGTH: 13
<212> TYPE: PRT
<213> ORGANISM: Artificial sequence
<220> FEATURE:
<223> OTHER INFORMATION: Synthetic sequence

<400> SEQUENCE: 18

Ala Lys Phe Val Ala Ala Trp Thr Leu Lys Ala Ala Ala
1               5                  10

<210> SEQ ID NO 19
<211> LENGTH: 15
<212> TYPE: PRT
<213> ORGANISM: Artificial sequence
<220> FEATURE:
<223> OTHER INFORMATION: Synthetic sequence

<400> SEQUENCE: 19

Gln Ser Ile Ala Leu Ser Ser Leu Met Val Ala Gln Ala Ile Pro
1               5                  10                  15

<210> SEQ ID NO 20
<211> LENGTH: 32
<212> TYPE: PRT
<213> ORGANISM: Artificial sequence
<220> FEATURE:
<223> OTHER INFORMATION: Synthetic sequence

<400> SEQUENCE: 20

Ile Leu Met Gln Tyr Ile Lys Ala Asn Ser Lys Phe Ile Gly Ile Pro
1               5                  10                  15

Met Gly Leu Pro Gln Ser Ile Ala Leu Ser Ser Leu Met Val Ala Gln
            20                  25                  30

<210> SEQ ID NO 21
<211> LENGTH: 242
<212> TYPE: PRT
<213> ORGANISM: Artificial sequence
<220> FEATURE:
<223> OTHER INFORMATION: Synthetic sequence

<400> SEQUENCE: 21

Ala Ala Ala Lys Pro Ala Thr Thr Glu Gly Glu Phe Pro Glu Thr Arg
1               5                  10                  15

Glu Lys Met Ser Gly Ile Arg Arg Ala Ile Ala Lys Ala Met Val His
            20                  25                  30

Ser Lys His Thr Ala Pro His Val Thr Leu Met Asp Glu Ala Asp Val
        35                  40                  45

Thr Lys Leu Val Ala His Arg Lys Lys Phe Lys Ala Ile Ala Ala Glu

```
            50                  55                  60
Lys Gly Ile Lys Leu Thr Phe Leu Pro Tyr Val Val Lys Ala Leu Val
 65                  70                  75                  80

Ser Ala Leu Arg Glu Tyr Pro Val Leu Asn Thr Ala Ile Asp Asp Glu
                 85                  90                  95

Thr Glu Glu Ile Ile Gln Lys His Tyr Tyr Asn Ile Gly Ile Ala Ala
            100                 105                 110

Asp Thr Asp Arg Gly Leu Leu Val Pro Val Ile Lys His Ala Asp Arg
            115                 120                 125

Lys Pro Ile Phe Ala Leu Ala Gln Glu Ile Asn Glu Leu Ala Glu Lys
            130                 135                 140

Ala Arg Asp Gly Lys Leu Thr Pro Gly Glu Met Lys Gly Ala Ser Cys
145                 150                 155                 160

Thr Ile Thr Asn Ile Gly Ser Ala Gly Gly Gln Trp Phe Thr Pro Val
                165                 170                 175

Ile Asn His Pro Glu Val Ala Ile Leu Gly Ile Gly Arg Ile Ala Glu
                180                 185                 190

Lys Pro Ile Val Arg Asp Gly Glu Ile Val Ala Ala Pro Met Leu Ala
            195                 200                 205

Leu Ser Leu Ser Phe Asp His Arg Met Ile Asp Gly Ala Thr Ala Gln
            210                 215                 220

Lys Ala Leu Asn His Ile Lys Arg Leu Leu Ser Asp Pro Glu Leu Leu
225                 230                 235                 240

Leu Met

<210> SEQ ID NO 22
<211> LENGTH: 205
<212> TYPE: PRT
<213> ORGANISM: Artificial sequence
<220> FEATURE:
<223> OTHER INFORMATION: Synthetic sequence

<400> SEQUENCE: 22

Met Lys Met Glu Glu Leu Phe Lys Lys His Lys Ile Val Ala Val Leu
 1               5                  10                  15

Arg Ala Asn Ser Val Glu Glu Ala Lys Lys Ala Leu Ala Val Phe
                 20                  25                  30

Leu Gly Gly Val His Leu Ile Glu Ile Thr Phe Thr Val Pro Asp Ala
             35                  40                  45

Asp Thr Val Ile Lys Glu Leu Ser Phe Leu Lys Glu Met Gly Ala Ile
             50                  55                  60

Ile Gly Ala Gly Thr Val Thr Ser Val Glu Gln Cys Arg Lys Ala Val
 65                  70                  75                  80

Glu Ser Gly Ala Glu Phe Ile Val Ser Pro His Leu Asp Glu Glu Ile
                 85                  90                  95

Ser Gln Phe Cys Lys Glu Lys Gly Val Phe Tyr Met Pro Gly Val Met
            100                 105                 110

Thr Pro Thr Glu Leu Val Lys Ala Met Lys Leu Gly His Thr Ile Leu
            115                 120                 125

Lys Leu Phe Pro Gly Glu Val Val Gly Pro Gln Phe Val Lys Ala Met
            130                 135                 140

Lys Gly Pro Phe Pro Asn Val Lys Phe Val Pro Thr Gly Gly Val Asn
145                 150                 155                 160

Leu Asp Asn Val Cys Glu Trp Phe Lys Ala Gly Val Leu Ala Val Gly
                165                 170                 175
```

-continued

Val Gly Ser Ala Leu Val Lys Gly Thr Pro Val Glu Val Ala Glu Lys
            180                 185                 190

Ala Lys Ala Phe Val Glu Lys Ile Arg Gly Cys Thr Glu
        195                 200                 205

<210> SEQ ID NO 23
<211> LENGTH: 625
<212> TYPE: PRT
<213> ORGANISM: Artificial sequence
<220> FEATURE:
<223> OTHER INFORMATION: Synthetic sequence

<400> SEQUENCE: 23

Ala Glu Asn Leu Trp Val Thr Val Tyr Tyr Gly Val Pro Val Trp Lys
1               5                   10                  15

Asp Ala Glu Thr Thr Leu Phe Cys Ala Ser Asp Ala Lys Ala Tyr Glu
            20                  25                  30

Thr Glu Lys His Asn Val Trp Ala Thr His Ala Cys Val Pro Thr Asp
        35                  40                  45

Pro Asn Pro Gln Glu Ile His Leu Glu Asn Val Thr Glu Glu Phe Asn
    50                  55                  60

Met Trp Lys Asn Asn Met Val Glu Gln Met His Thr Asp Ile Ile Ser
65                  70                  75                  80

Leu Trp Asp Gln Ser Leu Lys Pro Cys Val Lys Leu Thr Pro Leu Cys
                85                  90                  95

Val Thr Leu Gln Cys Thr Asn Val Thr Asn Asn Ile Thr Asp Asp Met
            100                 105                 110

Arg Gly Glu Leu Lys Asn Cys Ser Phe Asn Met Thr Thr Glu Leu Arg
        115                 120                 125

Asp Lys Lys Gln Lys Val Tyr Ser Leu Phe Tyr Arg Leu Asp Val Val
    130                 135                 140

Gln Ile Asn Glu Asn Gln Gly Asn Arg Ser Asn Asn Ser Asn Lys Glu
145                 150                 155                 160

Tyr Arg Leu Ile Asn Cys Asn Thr Ser Ala Ile Thr Gln Ala Cys Pro
                165                 170                 175

Lys Val Ser Phe Glu Pro Ile Pro Ile His Tyr Cys Ala Pro Ala Gly
            180                 185                 190

Phe Ala Ile Leu Lys Cys Lys Asp Lys Lys Phe Asn Gly Thr Gly Pro
        195                 200                 205

Cys Pro Ser Val Ser Thr Val Gln Cys Thr His Gly Ile Lys Pro Val
    210                 215                 220

Val Ser Thr Gln Leu Leu Leu Asn Gly Ser Leu Ala Glu Glu Glu Val
225                 230                 235                 240

Met Ile Arg Ser Glu Asn Ile Thr Asn Asn Ala Lys Asn Ile Leu Val
                245                 250                 255

Gln Phe Asn Thr Pro Val Gln Ile Asn Cys Thr Arg Pro Asn Asn Asn
            260                 265                 270

Thr Arg Lys Ser Ile Arg Ile Gly Pro Gly Gln Ala Phe Tyr Ala Thr
        275                 280                 285

Gly Asp Ile Ile Gly Asp Ile Arg Gln Ala His Cys Asn Val Ser Lys
    290                 295                 300

Ala Thr Trp Asn Glu Thr Leu Gly Lys Val Val Lys Gln Leu Arg Lys
305                 310                 315                 320

His Phe Gly Asn Asn Thr Ile Ile Arg Phe Ala Asn Ser Ser Gly Gly
                325                 330                 335

```
Asp Leu Glu Val Thr Thr His Ser Phe Asn Cys Gly Glu Phe
            340                 345                 350

Tyr Cys Asn Thr Ser Gly Leu Phe Asn Ser Thr Trp Ile Ser Asn Thr
            355                 360                 365

Ser Val Gln Gly Ser Asn Ser Thr Gly Ser Asn Asp Ser Ile Thr Leu
        370                 375                 380

Pro Cys Arg Ile Lys Gln Ile Ile Asn Met Trp Gln Arg Ile Gly Gln
385                 390                 395                 400

Ala Met Tyr Ala Pro Pro Ile Gln Gly Val Ile Arg Cys Val Ser Asn
                405                 410                 415

Ile Thr Gly Leu Ile Leu Thr Arg Asp Gly Gly Ser Thr Asn Ser Thr
            420                 425                 430

Thr Glu Thr Phe Arg Pro Gly Gly Gly Asp Met Arg Asp Asn Trp Arg
            435                 440                 445

Ser Glu Leu Tyr Lys Tyr Lys Val Val Lys Ile Glu Pro Leu Gly Val
        450                 455                 460

Ala Pro Thr Arg Cys Lys Arg Arg Val Val Gly Gly Gly Gly Gly Ser
465                 470                 475                 480

Gly Gly Gly Gly Ser Ala Val Gly Ile Gly Ala Val Phe Leu Gly Phe
                485                 490                 495

Leu Gly Ala Ala Gly Ser Thr Met Gly Ala Ala Ser Met Thr Leu Thr
            500                 505                 510

Val Gln Ala Arg Asn Leu Leu Ser Gly Asn Pro Asp Trp Leu Pro Asp
        515                 520                 525

Met Thr Val Trp Gly Ile Lys Gln Leu Gln Ala Arg Val Leu Ala Val
        530                 535                 540

Glu Arg Tyr Leu Arg Asp Gln Gln Leu Leu Gly Ile Trp Gly Cys Ser
545                 550                 555                 560

Gly Lys Leu Ile Cys Cys Thr Asn Val Pro Trp Asn Ser Ser Trp Ser
                565                 570                 575

Asn Arg Asn Leu Ser Glu Ile Trp Asp Asn Met Thr Trp Leu Gln Trp
            580                 585                 590

Asp Lys Glu Ile Ser Asn Tyr Thr Gln Ile Ile Tyr Gly Leu Leu Glu
        595                 600                 605

Glu Ser Gln Asn Gln Gln Glu Lys Asn Glu Gln Asp Leu Leu Ala Leu
    610                 615                 620

Asp
625

<210> SEQ ID NO 24
<211> LENGTH: 10
<212> TYPE: PRT
<213> ORGANISM: Artificial sequence
<220> FEATURE:
<223> OTHER INFORMATION: Synthetic sequence

<400> SEQUENCE: 24

Gly Gly Gly Gly Ser Gly Gly Gly Gly Ser
1               5                   10

<210> SEQ ID NO 25
<211> LENGTH: 205
<212> TYPE: PRT
<213> ORGANISM: Artificial sequence
<220> FEATURE:
<223> OTHER INFORMATION: Synthetic sequence
```

<400> SEQUENCE: 25

Met Lys Met Glu Glu Leu Phe Lys Lys His Lys Ile Val Ala Val Leu
1               5                   10                  15

Arg Ala Asn Ser Val Glu Glu Ala Lys Met Lys Ala Leu Ala Val Phe
                20                  25                  30

Val Gly Gly Val His Leu Ile Glu Ile Thr Phe Thr Val Pro Asp Ala
            35                  40                  45

Asp Thr Val Ile Lys Glu Leu Ser Phe Leu Lys Glu Leu Gly Ala Ile
        50                  55                  60

Ile Gly Ala Gly Thr Val Thr Ser Val Glu Gln Cys Arg Lys Ala Val
65                  70                  75                  80

Glu Ser Gly Ala Glu Phe Ile Val Ser Pro His Leu Asp Glu Glu Ile
                85                  90                  95

Ser Gln Phe Cys Lys Glu Lys Gly Val Phe Tyr Met Pro Gly Val Met
                100                 105                 110

Thr Pro Thr Glu Leu Val Lys Ala Met Lys Leu Gly His Thr Ile Leu
            115                 120                 125

Lys Leu Phe Pro Gly Glu Val Val Gly Pro Gln Phe Val Lys Ala Met
130                 135                 140

Lys Gly Pro Phe Pro Asn Val Lys Phe Val Pro Thr Gly Gly Val Asn
145                 150                 155                 160

Leu Asp Asn Val Cys Glu Trp Phe Lys Ala Gly Val Leu Ala Val Gly
                165                 170                 175

Val Gly Ser Ala Leu Val Lys Gly Thr Ile Ala Glu Val Ala Ala Lys
            180                 185                 190

Ala Ala Ala Phe Val Glu Lys Ile Arg Gly Cys Thr Glu
            195                 200                 205

<210> SEQ ID NO 26
<211> LENGTH: 167
<212> TYPE: PRT
<213> ORGANISM: Artificial sequence
<220> FEATURE:
<223> OTHER INFORMATION: Synthetic sequence

<400> SEQUENCE: 26

Met Leu Ser Lys Asp Ile Ile Lys Leu Leu Asn Glu Gln Val Asn Lys
1               5                   10                  15

Glu Met Asn Ser Ser Asn Leu Tyr Met Ser Met Ser Ser Trp Cys Tyr
                20                  25                  30

Thr His Ser Leu Asp Gly Ala Gly Leu Phe Leu Phe Asp His Ala Ala
            35                  40                  45

Glu Glu Tyr Glu His Ala Lys Lys Leu Ile Ile Phe Leu Asn Glu Asn
        50                  55                  60

Asn Val Pro Val Gln Leu Thr Ser Ile Ser Ala Pro Glu His Lys Phe
65                  70                  75                  80

Glu Gly Leu Thr Gln Ile Phe Gln Lys Ala Tyr Glu His Glu Gln His
                85                  90                  95

Ile Ser Glu Ser Ile Asn Asn Ile Val Asp His Ala Ile Lys Ser Lys
            100                 105                 110

Asp His Ala Thr Phe Asn Phe Leu Gln Trp Tyr Val Ala Glu Gln His
        115                 120                 125

Glu Glu Glu Val Leu Phe Lys Asp Ile Leu Asp Lys Ile Glu Leu Ile
130                 135                 140

Gly Asn Glu Asn His Gly Leu Tyr Leu Ala Asp Gln Tyr Val Lys Gly

```
145                 150                 155                 160
Ile Ala Lys Ser Arg Lys Ser
                165

<210> SEQ ID NO 27
<211> LENGTH: 4
<212> TYPE: PRT
<213> ORGANISM: Artificial sequence
<220> FEATURE:
<223> OTHER INFORMATION: Synthetic sequence

<400> SEQUENCE: 27

Asn Ala Asn Pro
1
```